(12) United States Patent
Wang et al.

(10) Patent No.: US 7,342,006 B2
(45) Date of Patent: Mar. 11, 2008

(54) SUBSTITUTED 8-HETEROARYL XANTHINES

(75) Inventors: Guoquan Wang, Charlottesville, VA (US); Jayson M. Rieger, Charlottesville, VA (US); Robert D. Thompson, Charlottesville, VA (US)

(73) Assignee: Adenosine Therapeutics, LLC, Charlottesville, VA (US)

( * ) Notice: Subject to any disclaimer, the term of this patent is extended or adjusted under 35 U.S.C. 154(b) by 444 days.

(21) Appl. No.: 10/923,592

(22) Filed: Aug. 20, 2004

(65) Prior Publication Data

US 2005/0065341 A1 Mar. 24, 2005

Related U.S. Application Data

(60) Provisional application No. 60/497,875, filed on Aug. 25, 2003.

(51) Int. Cl.
*C07D 473/08* (2006.01)
*C07D 473/12* (2006.01)
*C07D 473/06* (2006.01)
*A61K 31/522* (2006.01)
*A61P 11/06* (2006.01)

(52) U.S. Cl. ............... 514/211.08; 544/268; 544/269; 544/270; 544/118; 544/310; 540/575; 514/263.2; 514/263.21; 514/263.22; 514/234.2

(58) Field of Classification Search ............... 544/118, 544/268, 269, 270; 514/234.2, 211, 263.21, 514/26, 263.2; 540/575
See application file for complete search history.

(56) References Cited

U.S. PATENT DOCUMENTS 6,770,267 B2 * 8/2004 Daluge et al. ................ 424/54
2007/0219221 A1 * 9/2007 Zeng et al. ............... 514/263.2

FOREIGN PATENT DOCUMENTS

WO WO 03/042214 A2 5/2003
WO WO 03/063800 A2 8/2003

OTHER PUBLICATIONS

Sekine et al., Chemical and pharmaceutical bulletin 1989, vol. 37, No. 8, pp. 1987-1989.*
Scammells, Journal of Medicinal Chemistry (1994), 37(17), 2704-12.*

* cited by examiner

*Primary Examiner*—Mark L. Berch
(74) *Attorney, Agent, or Firm*—Kelly Hallowell; Williams Mullen

(57) ABSTRACT

Selective antagonists of $A_{2B}$ adenosine receptors like those of formula I are provide.

The compounds and compositions are useful as pharmaceutical agents.

55 Claims, No Drawings

SUBSTITUTED 8-HETEROARYL XANTHINES

CROSS-REFERENCE TO RELATED APPLICATIONS

This application claims the benefit of U.S. Provisional Application No. 60/497,875 filed Aug. 25, 2003.

FIELD OF THE INVENTION

The present invention relates to compounds and pharmaceutical compositions that are selective antagonists of $A_{2B}$ adenosine receptors (ARs). These compounds and compositions are useful as pharmaceutical agents.

BACKGROUND OF THE INVENTION

The alkylxanthine theophylline (compound A) a weak non-selective

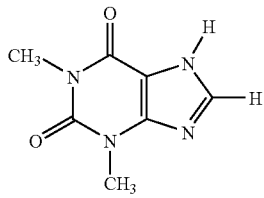

A adenosine antagonist (See Linden, J., et al., *Cardiovascular Biology of Purines*, eds. G. Burnstock, et al., 1998, pp 1-20) is useful therapeutically for the treatment of asthma. However, its use is associated with unpleasant side effects, such as insomnia and diuresis. In recent years, the use of theophylline as a bronchodilator, for relief of asthma, has been supplanted by drugs of other classes, i.e., selective $\beta_2$-adrenergic agonists, corticosteroids, and recently leukotriene antagonists. These compounds also have limitations, thus, the development of a theophylline-like drug with reduced side effects is still desirable.

It has been recognized that theophylline and its closely related analogue caffeine block endogenous adenosine acting as a local modulator of adenosine receptors in the brain and other organs at therapeutically useful doses. Adenosine activates four subtypes of G protein-coupled adenosine receptors (ARs), $A_1/A_{2A}/A_{2B}/A_3$. Enprofylline, (compound B), is another example of a xanthine

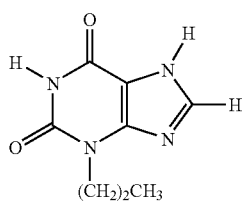

B that has been reported to block $A_{2B}$ adenosine receptors and is used to treat asthma. However, this compound only weakly blocks $A_1$, $A_{2A}$ and $A_3$ adenosine receptors. It has also been shown by LaNoue et al (U.S. Pat. No. 6,060,481) that selective adenosine $A_{2B}$ antagonists are useful for improving insulin sensitivity in a patient.

It has been reported that therapeutic concentrations of theophylline or enprofylline block human $A_{2B}$ receptors, and it has been proposed that antagonists selective for this subtype may have potential use as antiasthmatic agents. (See Feoktistov, I., et al., *Pharmacol. Rev.* 1997, 49, 381-402; and Robeva, A. S., et al., *Drug Dev. Res.* 1996, 39, 243-252). Enprofylline has a reported $K_i$ value of 7 µM and is somewhat selective in binding to human $A_{2B}$ ARs. (See Robeva, A. S., et al., *Drug Dev. Res.* 1996, 39, 243-252 and Linden, J., et al., *Mol. Pharmacol.* 1999, 56, 705-713). $A_{2B}$ ARs are expressed in some mast cells, such as the BR line of canine mastocytoma cells, which appear to be responsible for triggering acute $Ca^{2+}$ mobilization and degranulation. (See Auchampach, J. A., et al., *Mol. Pharmacol.* 1997, 52, 846-860 and Forsyth, P., et al., *Inflamm. Res.* 1999, 48, 301-307). $A_{2B}$ ARs also trigger $Ca^{2+}$ mobilization, and participate in a delayed IL8 release from human HMC-1 mast cells. Other functions associated with the $A_{2B}$ AR are the control of cell growth and gene expression, (See Neary, J., et al., *Trends Neurosci.* 1996, 19, 13-18) endothelial-dependent vasodilation (See Martin, P. L., et al., *J. Pharmacol. Exp. Ther.* 1993, 265, 248-253), and fluid secretion from intestinal epithelia. (See Strohmeier, G. R., et al., *J. Biol. Chem.* 1995, 270, 2387-2394). Adenosine acting through $A_{2B}$ ARs has also been reported to stimulate chloride permeability in cells expressing the cystic fibrosis transport regulator. (See Clancy, J. P., et al., *Am. J. Physiol.* 1999, 276, C361-C369.)

Recently Linden et al (U.S. Pat. No. 6,545,002) have described a new group of compounds and pharmaceutical compositions that are selective antagonists of $A_{2B}$ adenosine receptors (ARs).

Although adenosine receptor subtype-selective probes are available for the $A_1$, $A_{2A}$, and $A_3$ ARs, only few selective antagonists and no selective agonists are known for the $A_{2B}$ receptor. Therefore, a continuing need exists for compounds that are selective $A_{2B}$ receptor antagonists.

SUMMARY OF THE INVENTION

The present invention provides compounds that act as antagonists of $A_{2B}$ adenosine receptors. Accordingly, the present invention provides a compound of formula I:

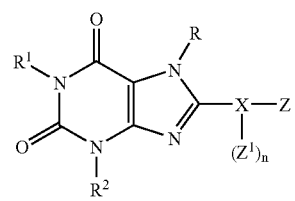

I wherein:
R is hydrogen, $(C_1-C_5)$alkyl, halo$(C_1-C_8)$alkyl, $(C_3-C_5)$alkenyl, or $(C_3-C_5)$alkynyl;

$R^1$ and $R^2$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_4-C_{10})$heterocycle, $(C_4-C_{10})$heterocycle$(C_1-C_8)$alkyl-, $(C_6-C_{10})$aryl, $(C_6-C_{10})$aryl$(C_1-C_8)$alkyl-, $(C_5-C_{10})$heteroaryl, or $(C_5-C_{10})$heteroaryl$(C_1-C_8)$alkyl-;

X is a 5-10 member heteroaryl ring having one nitrogen atom and optionally interrupted by 1, 2, or 3 non-peroxide oxy (—O—), thio (—S—), sulfinyl (—SO—), sulfonyl (—S(O)$_2$—) or amine —N(R$^9$)— groups;

Z is —OR$^3$, —SR$^3$, halo, —S(O)$_m$—NR$^4$R$^5$, —NR$^4$R$^5$, or (C$_4$-C$_{10}$)heterocycle wherein the heterocycle is optionally substituted with 1, 2, 3, or 4 substituents independently selected from halo, cyano, nitro, —OR$^a$, —SR$^a$, (C$_1$-C$_8$)alkyl, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$;

each Z$^1$ is independently (C$_1$-C$_8$)alkyl, (C$_2$-C$_8$)alkenyl, (C$_2$-C$_8$)alkynyl, —OR$^6$, —SR$^6$, halo, R$^6$O(C$_1$-C$_8$)alkyl, R$^7$R$^8$N(C$_1$-C$_8$)alkyl, halo(C$_1$-C$_8$)alkyl, —NR$^7$R$^8$, R$^7$R$^8$N(C$_1$-C$_8$)alkyl, —C(O)R$^6$, —COOR$^6$, and —C(O)NR$^7$R$^8$;

R$^3$ is (C$_1$-C$_8$)alkyl, (C$_3$-C$_8$)alkenyl, (C$_3$-C$_8$)alkynyl, (C$_6$-C$_{10}$)aryl, (C$_6$-C$_{10}$)aryl(C$_1$-C$_8$)alkyl-, (C$_5$-C$_{10}$)heteroaryl, (C$_5$-C$_{10}$)heteroaryl(C$_1$-C$_8$)alkyl-, —C(O)R$^6$, or —C(O)NR$^7$R$^8$;

R$^4$ and R$^5$ are independently hydrogen, (C$_1$-C$_8$)alkyl, (C$_3$-C$_8$)alkenyl, (C$_3$-C$_8$)alkynyl, (C$_1$-C$_8$)alkoxy, (C$_3$-C$_8$)cycloalkyl, (C$_3$-C$_8$)cycloalkyl(C$_1$-C$_8$)alkyl-, (C$_6$-C$_{18}$)polycycloalkyl, (C$_6$-C$_{18}$)polycycloalkyl(C$_1$-C$_8$)alkyl-, (C$_3$-C$_{10}$)heterocycle, (C$_3$-C$_{10}$)heterocycle(C$_1$-C$_8$)alkyl —NR$^7$R$^8$, (C$_6$-C$_{10}$)aryl, (C$_6$-C$_{10}$)aryl(C$_1$-C$_8$)alkyl-, (C$_5$-C$_{10}$)heteroaryl, (C$_5$-C$_{10}$)heteroaryl(C$_1$-C$_8$)alkyl-, —(C$_2$-C$_4$—Y)$_q$—(CH$_2$)$_{2-4}$—X$^1$, —C(O)R$^6$, —CO$_2$R$^6$, —C(O)NR$^7$R$^8$, or —S(O)$_2$—NR$^7$R$^8$; or R$^4$ and R$^5$ together with the atoms to which they are attached form a saturated or partially unsaturated, mono-, bicyclic- or aromatic ring having 3, 4, 5, 6, 7, or 8, ring atoms and optionally comprising 1, 2, 3, or 4 heteroatoms selected from non-peroxide oxy (—O—), thio (—S—), sulfinyl (—SO—), sulfonyl (—S(O)$_2$—) and amine —N(R$^9$)— in the ring, wherein the ring is optionally substituted with 1, 2, 3, or 4 substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$;

X$^1$ is —OR$^6$, —C(O)R$^6$, —CO$_2$R$^6$, or —NR$^7$R$^8$; and Y is oxy (—O—), thio (—S—), sulfinyl (—SO—), sulfonyl (—S(O)$_2$—) and amine —N(R$^9$)—;

wherein the alkyl, alkenyl, cycloalkyl, alkynyl, aryl, heterocycle, or heteroaryl groups of R$^1$, R$^2$, R$^3$, R$^4$ and R$^5$ groups are optionally substituted with one or more substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$;

wherein R$^6$ is hydrogen, (C$_1$-C$_8$)alkyl, R$^a$O(C$_1$-C$_8$)alkyl, R$^b$R$^c$N(C$_1$-C$_8$)alkyl, halo(C$_1$-C$_8$)alkyl, (C$_3$-C$_{10}$)heterocycle, (C$_3$-C$_{10}$)heterocycle(C$_1$-C$_8$)alkyl-, (C$_6$-C$_{10}$)aryl, (C$_6$-C$_{10}$)aryl(C$_1$-C$_8$)alkyl-, (C$_4$-C$_{10}$)heteroaryl, (C$_4$-C$_{10}$)heteroaryl(C$_1$-C$_8$)alkyl-; wherein the heterocycle, heteroaryl or aryl are optionally substituted with 1, 2, 3, or 4 substituents independently selected from halo, cyano, nitro, —OR$^a$, SR$^a$, (C$_6$-C$_{10}$)aryl —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$;

wherein R$^7$, R$^8$ and R$^9$ are independently hydrogen, (C$_1$-C$_8$)alkyl, R$^a$O(C$_1$-C$_8$)alkyl, R$^b$R$^c$N(C$_1$-C$_8$)alkyl, halo(C$_1$-C$_8$)alkyl, (C$_3$-C$_{10}$)heterocycle, (C$_6$-C$_{10}$)aryl, (C$_6$-C$_{10}$)aryl(C$_1$-C$_8$)alkyl-, (C$_4$-C$_{10}$)heteroaryl; —COOR$^a$, —C(O)R$^a$, or —C(O)NR$^b$R$^c$ wherein the heterocycle, heteroaryl or aryl are optionally substituted with 1, 2, 3, or 4 substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and C(O)NR$^b$R$^c$; or R$^7$ and R$^8$ together with the atoms to which they are attached form a saturated or partially unsaturated, mono-, bicyclic- or aromatic ring having 3, 4, 5, 6, 7, or 8, ring atoms optionally ring having from 4 to eight ring atoms and optionally comprising 1, 2, 3, or 4 heteroatoms selected from non-peroxide oxy (—O—), thio (—S—), sulfinyl (—SO—), sulfonyl (—S(O)$_2$—) or amine —N(R$^b$)— in the ring;

R$^a$ is hydrogen, or (C$_1$-C$_6$)alkyl; R$^b$ and R$^c$ are each independently hydrogen, (C$_1$-C$_6$)alkyl, (C$_1$-C$_6$)alkoxy, (C$_3$-C$_8$)cycloalkyl, (C$_1$-C$_6$)alkylthio, (C$_6$-C$_{10}$)aryl, (C$_6$-C$_{10}$)aryl(C$_1$-C$_6$)alkyl-, heteroaryl, or heteroaryl (C$_1$-C$_6$)alkyl-; or R$^b$ and R$^c$ together with the nitrogen to which they are attached, form a pyrrolidyl, piperidyl, piperazinyl, azepinyl, diazepinyl, morpholinyl, or thiomorpholinyl ring;

where n is 0, 1, 2, 3, 4, 5, 6, 7, or 8; m is 1, or 2; and q is 1, 2, 3, or 4; or a pharmaceutically acceptable salt thereof.

The invention also provides pharmaceutically acceptable salts of a compound of formula (I). The invention also provides a pharmaceutical composition comprising a compound of formula I, or a pharmaceutically acceptable salt thereof, in combination with a pharmaceutically acceptable diluent or carrier.

Additionally, the invention provides a therapeutic method for preventing or treating a pathological condition or symptom in a mammal, such as a human, wherein the activity, i.e., over-activity, of adenosine A$_{2B}$ receptors is implicated in one or more symptoms of the pathology and antagonism (i.e., blocking) of their activity is desired to ameliorate said symptoms. Such diseases or conditions include, but are not limited to, asthma, allergies, allergic diseases (e.g. allergic rhinitis and-sinusitis), autoimmune diseases (e.g. lupus), diarrheal diseases, insulin resistance, diabetes, prevention of mast cell degranulation associated with ischemia/reperfusion injuries, heart attack, inhibition of angiogenesis in neoplastic tissues, and inhibition of angiogenesis in diabetic retinopathy or hyperbaric oxygen-induced retinopathy. The invention also includes a method for treating asthma, diarrheal diseases, insulin resistance, diabetes, inhibition of angiogenesis in neoplastic tissues, and inhibition of angiogenesis in diabetic retinopathy or hyperbaric oxygen-induced retinopathy in a mammal, (e.g., a human) comprising administering to the mammal in need of such therapy, an effective amount of at least one compound of formula I or pharmaceutically acceptable salt(s) thereof.

The invention provides a compound of formula I for use in medical therapy, preferably for use in treating diseases or conditions associated with deleterious A$_{2B}$ receptor activation or activity, including asthma, diarrheal diseases, insulin resistance, diabetes, ischemic/reperfusion injury, inhibition of angiogenesis in neoplastic tissues, and inhibition of angiogenesis in diabetic retinopathy or hyperbaric oxygen-induced retinopathy.

The invention also provides the use of a compound of formula I for the manufacture of a medicament for the treatment of a pathological condition or symptom in a mammal, such as a human, which is associated with deleterious $A_{2B}$ receptor activation or activity, including the above-referenced diseases or pathologies.

The invention also includes a method comprising contacting a compound of formula I, optionally having a radioactive isotope (radionuclide), such as, for example, tritium, radioactive iodine (for example, $^{125}I$ for binding assays or $^{123}I$ for Spectral Imaging) and the like, with target $A_{2B}$ adenosine receptor sites comprising said receptors, in vivo or in vitro, so as to bind to said receptors. Cell membranes comprising bound $A_{2B}$ adenosine receptor sites can be used to measure the selectivity of test compounds for adenosine receptor subtypes or can be used as a tool to identify potential therapeutic agents for the treatment of diseases or conditions associated with $A_{2B}$-receptor mediation, by contacting said agents with said radioligands and receptors, and measuring the extent of displacement of the radioligand and/or binding of the agent.

DETAILED DESCRIPTION OF THE INVENTION

Applicants have discovered that compounds of the invention having formula I, can be useful for the treatment diseases or conditions associated with deleterious $A_{2B}$ receptor activation or activity.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

"Aryl" denotes a phenyl radical or an ortho-fused bicyclic carbocyclic radical having about nine to ten ring atoms in which at least one ring is aromatic.

"Arylalkyl" or "$(C_6-C_{10})aryl(C_1-C_8)alkyl$-" refer to a group of the formula aryl($C_1-C_8$)alkyl-, where aryl and ($C_1-C_8$)alkyl are as defined herein.

"Heterocycle" encompasses a cyclic radical attached or linked via a nitrogen or carbon ring atom of a monocyclic, fused-bicyclic, or bridged-bicyclic, saturated or unsaturated, ring system containing 5-10 ring atoms and preferably from 5-6 ring atoms, consisting of carbon and one, two, three or four heteroatoms each selected from the group consisting of non-peroxide oxy (—O—), thio (—S—), sulfinyl (—SO—), sulfonyl (—S(O)$_2$—), amine —N(R$^9$)—, or —N= groups, wherein R$^9$ is as defined herein, and optionally containing 1-3 double bonds (e.g., —CH=CH— or —CH=N—). Heterocycle includes, for example, tetrahydrofuryl, dihydrofuryl, tetrahydroimidazolyl, azanorbornyl, pyrrolidyl, piperidyl, piperizyl, morpholinyl, azepinyl, 1,3-diazepinyl, 1,3-benzodiazepinyl, 1,4-diazepinyl, 1,4-benzodiazepinyl, 1,5-diazepinyl, 1,5-benzodiazepino and the like.

"Heteroaryl" encompasses a radical attached via a ring atom of a monocyclic aromatic ring containing 5-10 ring atoms, and preferably from 5-6 ring atoms, consisting of carbon and one, two, three or four heteroatoms each selected from the group consisting of non-peroxide oxy (—O—), thio (—S—), sulfinyl (—SO—), sulfonyl (—S(O)$_2$—) or amine (—N(R$^9$)—) groups, wherein R$^9$ is as defined herein. Preferred heteroaryl groups include imidazolyl, triazolyl, triazinyl, oxazoyl, isoxazoyl, thiazolyl, isothiazoyl, thiodiazolyl, pyrrolyl, pyrazinyl, tetrazolyl, pyridinyl, pyrimidinyl, indolyl, isoquinolyl, quinolyl and the like.

As is recognized by one of ordinary skill in the art, the imidazole ring of the compounds of the present invention may exist in tautomeric forms or as tautomers, and thus are also included within the scope of the invention. The tautomeric isomers are represented as the structures (Ia) and (Ib):

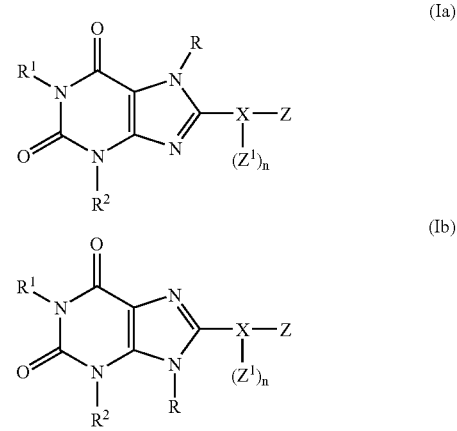

By naming or referring to one compound (I), for example, it is understood for the purposes of the present application that the tautomers (Ia) and (Ib) are also intended. Similarly, by referring to compound (Ia), it is understood for the purposes of the present application that the tautomers (I) and (Ib) are also intended. The same holds true for references to tautomer (Ib).

"Optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

It will be appreciated by those skilled in the art that compounds of the invention having a chiral center may exist in and be isolated in optically active, and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine, for example, anti-tumor activity, herbicidal activity, or other therapeutic activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_8)$alkyl can be methyl, ethyl, n-propyl, isopropyl, n-butyl, iso-butyl, sec-butyl, tert-butyl, n-pentyl, isopentyl, 3-pentyl, n-hexyl, n-heptyl, n-octyl or the branched $(C_3-C_8)$alkyl; $(C_2-C_8)$alkenyl can be vinyl, 1-propenyl, 2-propenyl (allyl), 1-butenyl, 2-butenyl, 3-butenyl, 1-pentenyl, 2-pentenyl, 3-pentenyl, 1-hexenyl, 2-hexenyl, 3-hexenyl, 1-heptenyl, 2-heptenyl, 3-heptenyl, 1-octenyl, 2-octenyl, 3-octenyl, 4-octenyl or the branched $(C_3-C_8)$ alkenyl; $(C_3-C_8)$alkenyl can be 2-propenyl(allyl), 2-butenyl, 3-butenyl, 2-pentenyl, 3-pentenyl, 1-hexenyl, 2-hexenyl, 3-hexenyl, 2-heptenyl, 3-heptenyl, 2-octenyl, 3-octenyl, 4-octenyl, or the branched $(C_3-C_8)$alkenyl; $(C_2-C_8)$alkynyl can be ethynyl, 1-propynyl, 2-propynyl(propargyl), 1-butynyl, 2-butynyl, 3-butynyl, 1-pentynyl, 2-pentynyl, 3-pentynyl, 1-hexynyl, 2-hexynyl, 3-hexynyl, 1-heptynyl, 2-heptynyl, 3-heptynyl, 1-octynyl, 2-octynyl, 3-octynyl, 4-octynyl, or the branched $(C_3-C_8)$alkynyl; $(C_3-C_8)$alkynyl can be 2-propynyl(propargyl), 2-butynyl, 3-butynyl, 1-pentynyl, 2-pentynyl, 3-pentynyl, 1-hexynyl, 2-hexynyl, 3-hexynyl, 1-heptynyl, 2-heptynyl, 3-heptynyl, 1-octynyl, 2-octynyl, 3-octynyl, 4-octynyl, or the branched $(C_3-C_8)$alkynyl; $(C_1-C_8)$alkoxy can be methoxy, ethoxy, n-propoxy, isopropoxy, n-butoxy, iso-butoxy, sec-butoxy, tert-butoxy, pentoxy, 3-pentoxy, n-hexyloxy, n-heptyloxy, n-octyloxy, or the branched $(C_3-C_8)$alkoxy; halo$(C_1-C_8)$alkyl can be iodomethyl, bromomethyl, chloromethyl, fluoromethyl, trifluoromethyl, 2-chloroethyl, 2-bromoethyl, 2-fluoroethyl, 3-fluoropropyl, 2,2,2-trifluoroethyl, pentafluoroethyl, or the branched halo$(C_3-C_8)$alkyl; $(C_3-C_8)$cycloalkyl can be cyclopropyl, cyclobutyl, cyclopentyl, cyclohexyl, cycloheptyl or cyclooctyl; $(C_3-C_8)$ cycloalkyl$(C_1-C_8)$alkyl- can be cyclopropylmethyl, cyclobutylmethyl, cyclopentylmethyl, cyclohexylmethyl, 2-cyclopropylethyl, 2-cyclobutylethyl, 2-cyclopentylethyl or 2-cyclohexylethyl; $(C_6-C_{10})$aryl can be phenyl, indenyl or naphthyl; Heterocycle can be tetrahydrofuryl, dihydrofuryl, tetrahydroimidazolyl, azanorbornyl, pyrrolidyl, piperidyl, piperizyl, morpholinyl, azepinyl, 1,3-diazepinyl, 1,3-benzodiazepinyl, 1,4-diazepinyl 1,4-benzodiazepinyl, 1,5-diazepinyl, or 1,5-benzodiazepino.

Arylalkyl can be phenylethyl, benzyl, 2-phenylpropyl, 3-phenylpropyl, 2-naphthylmethyl or 3-naphthylmethyl; and heteroaryl can be imidazolyl, triazolyl, triazinyl, oxazoyl, isoxazoyl, thiazolyl, isothiazoyl, pyrrolyl, pyrazinyl, tetrazolyl, pyridyl, pyrimidinyl, indolyl, isoquinolyl, quinolyl, or an oxide thereof.

The $(C_1-C_8)$alkyl groups can be methyl, ethyl, propyl, butyl, pentyl, hexyl, heptyl, and octyl; alkenyl groups are ethenyl, propenyl, butenyl, pentenyl, and hexenyl.

Specific cycloalkyl groups are cyclopropyl, cyclobutyl, cyclopentyl, and cyclohexyl.

Specific cycloalkylalkyl groups are cyclopropylmethyl, cyclobutylmethyl, cyclopropylethyl, cyclopentylmethyl, cyclohexylmethyl, 2-cyclopentylethyl, and 2-cyclohexylethyl.

Specific aryl groups are phenyl, indenyl or naphthyl.

Specific arylalkyl groups are benzyl and 2-phenylethyl.

Specific haloalkyl groups are bromoethyl, chloroethyl, fluoroethyl, trifluoromethyl, 2,2,2-trifluoroethyl or 3-fluoropropyl.

A specific value for R is hydrogen, methyl, ethyl, allyl, propargyl, i-propyl, n-propyl, n-butyl, i-butyl or halo$(C_1-C_4)$alkyl.

Another specific value for R is hydrogen, methyl, ethyl, $-CH_2-CH_2-Cl$, $-CH_2-CH_2-Br$, or $-CH_2-CH_2-CH_2-F$.

Another specific value for R is hydrogen.

A specific value for $R^1$ is hydrogen, $(C_1-C_4)$alkyl, $(C_3-C_4)$alkenyl, $(C_3-C_4)$alkynyl, phenyl, or phenyl$(C_1-C_4)$alkyl.

Another specific value for $R^1$ is $(C_3-C_6)$cycloalkyl and $(C_3-C_6)$cycloalkyl$(C_1-C_4)$alkyl.

Another specific value for $R^1$ is cyclopropyl or cyclopropylmethyl.

Another specific value for $R^1$ is hydrogen, methyl, ethyl, allyl, propargyl, i-propyl, n-propyl, n-butyl, i-butyl, phenyl, phenethyl, or benzyl.

Another specific value for $R^1$ is hydrogen, methyl, ethyl, allyl, propargyl, i-propyl, n-propyl, or (methoxyphenyl)ethyl.

Another specific value for $R^1$ is ethyl, n-propyl or allyl.

A specific value for $R^2$ is hydrogen, $(C_1-C_4)$alkyl, $(C_3-C_4)$alkenyl, $(C_3-C_4)$alkynyl, phenyl, or phenyl$(C_1-C_4)$alkyl.

Another specific value for $R^2$ is $(C_3-C_6)$cycloalkyl and $(C_3-C_6)$cycloalkyl$(C_1-C_4)$alkyl-.

Another specific value for $R^2$ is cyclopropyl or cyclopropylmethyl.

Another specific value for $R^2$ is hydrogen, methyl, ethyl, allyl, propargyl, i-propyl, n-propyl, n-butyl, i-butyl, phenyl, phenethyl, or benzyl.

Another specific value for $R^2$ is hydrogen, methyl, ethyl, allyl, propargyl, i-propyl, n-propyl, or (methoxyphenyl)ethyl.

Another specific value for $R^2$ is ethyl, n-propyl or allyl.

A specific value for X is imidazolyl, triazolyl, triazinyl, oxazoyl, isoxazoyl, thiazolyl, isothiazoyl, thiodiazolyl, pyrrolyl, pyrazinyl, tetrazolyl, pyridinyl, pyrimidinyl, indolyl, isoquinolyl, or quinolyl, each optionally substituted with 1, 2, or 3 substituents independently selected from halo, cyano, nitro, $(C_1-C_8)$alkyl, $-OR^a$, $-SR^a$, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $C(O)NR^bR^c$.

Another specific value for X is 2-pyridinyl, 3-pyridinyl, or 4-pyridinyl, each optionally substituted with 1, 2, or 3 substituents independently selected from halo, cyano, nitro, $(C_1-C_8)$alkyl, $OR^a$, $-SR^a$, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $-C(O)NR^bR^c$.

A specific value for $-X(Z^1)_n-Z$ is a group having the formula

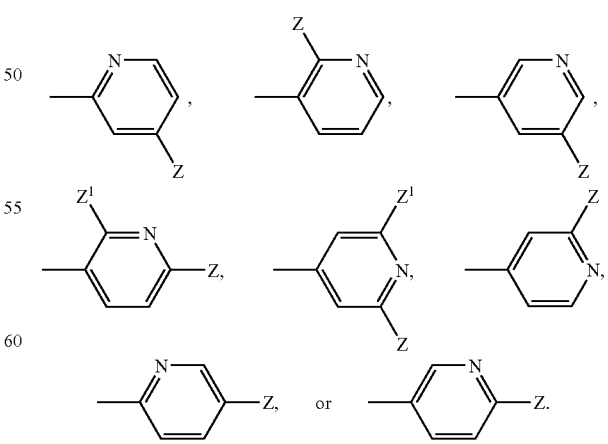

Another specific value for $-X(Z^1)_n-Z$ is a group having the formula:

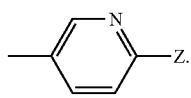
Another specific value for —X(Z$^1$)$_n$-Z is a group of the formula:
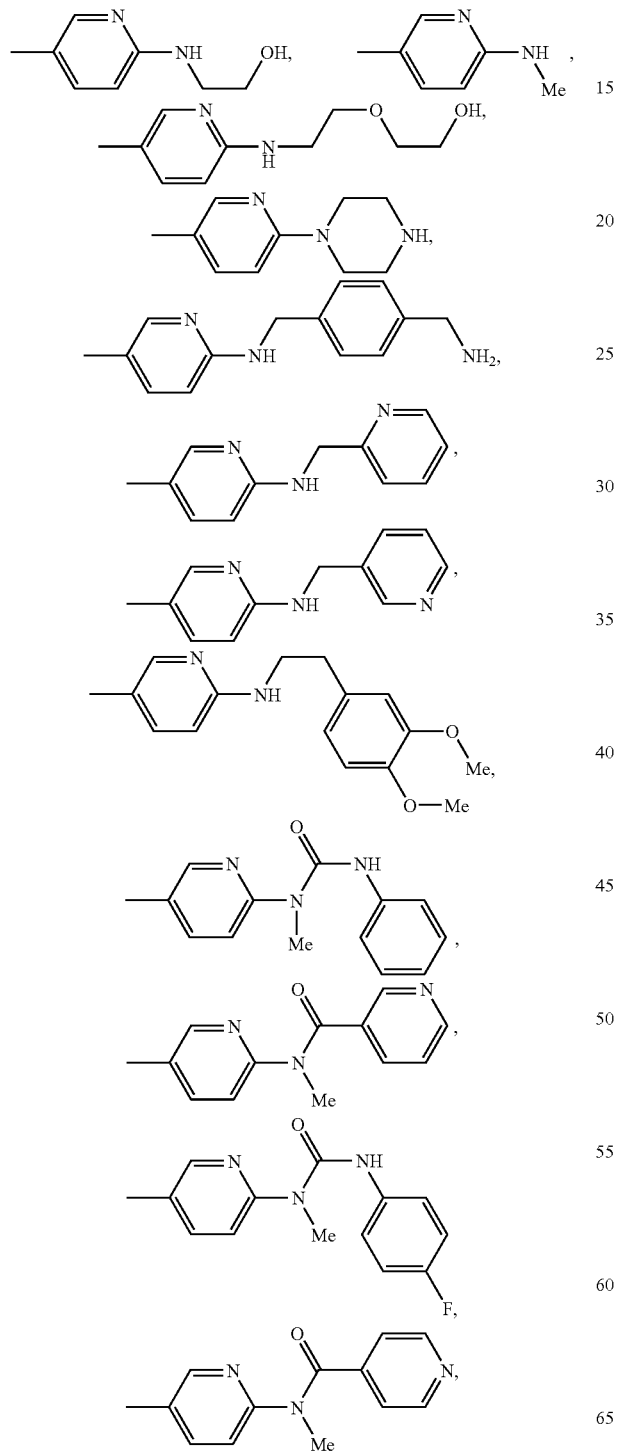
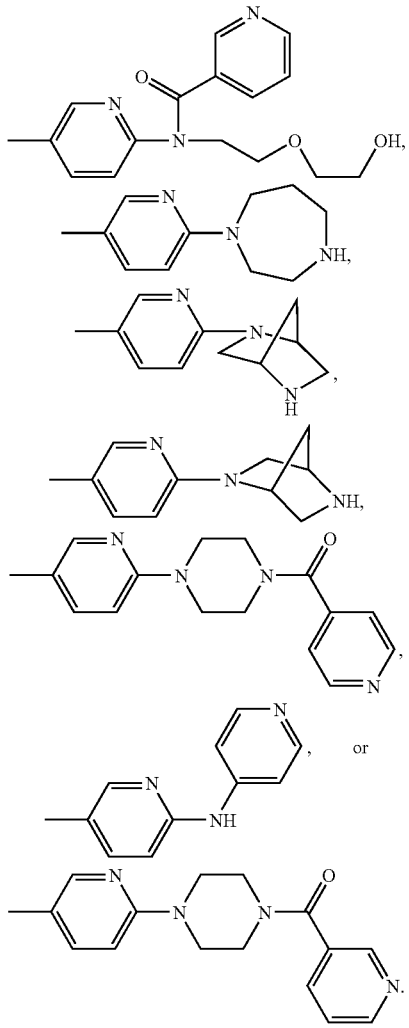
Another specific value for —X(Z$^1$)$_n$-Z is a group of the formula:
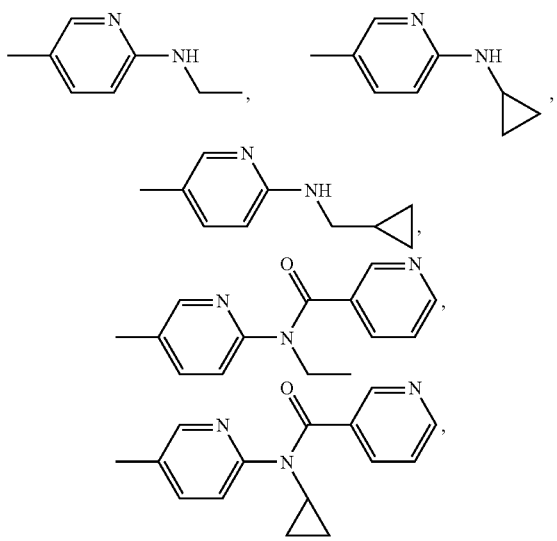

-continued
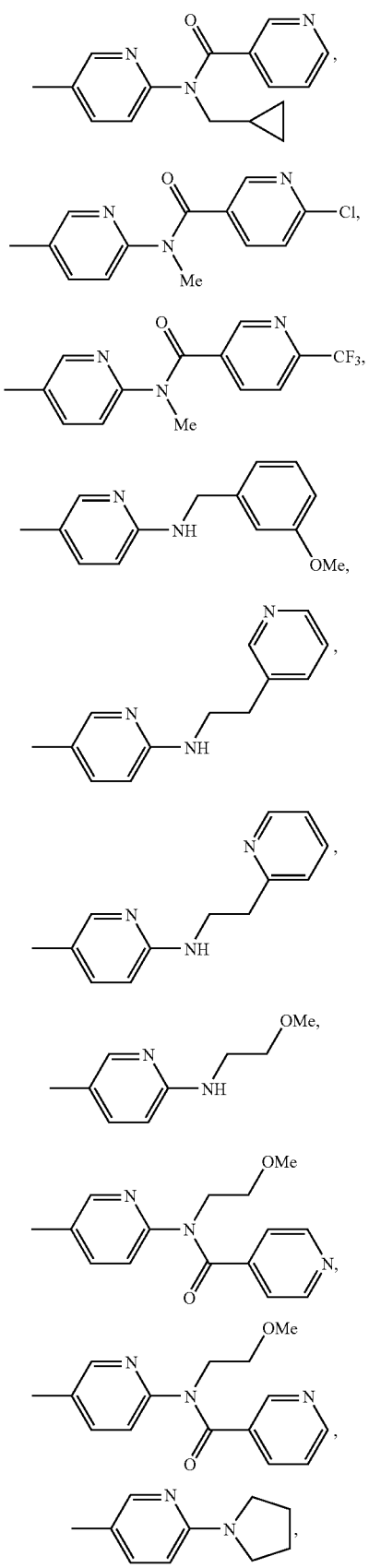
-continued
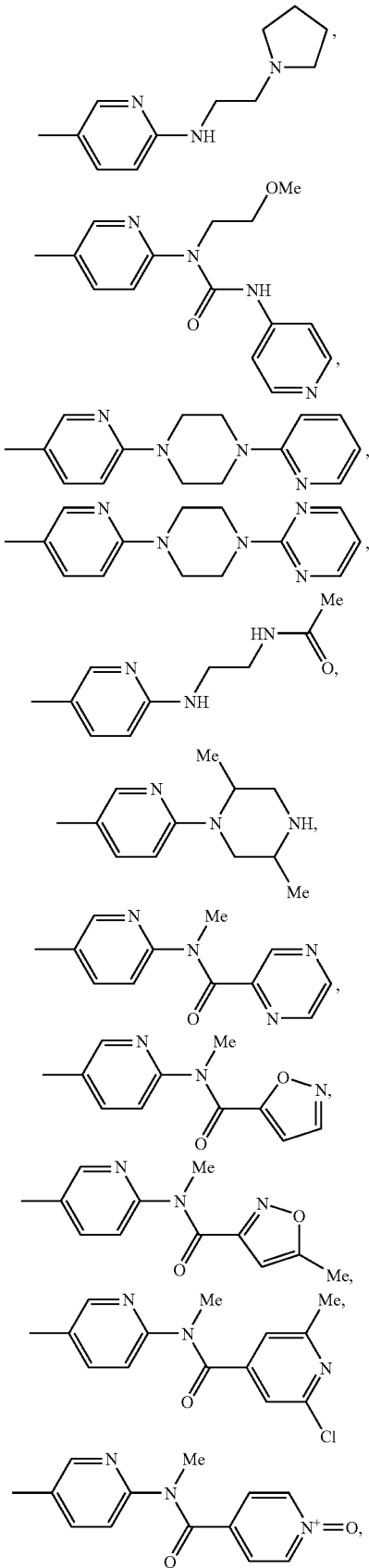

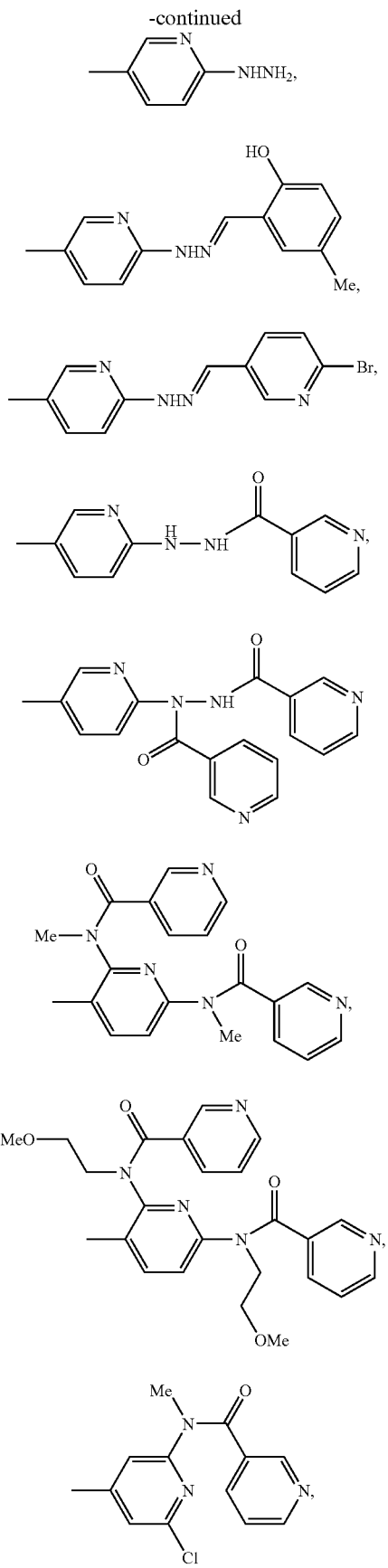

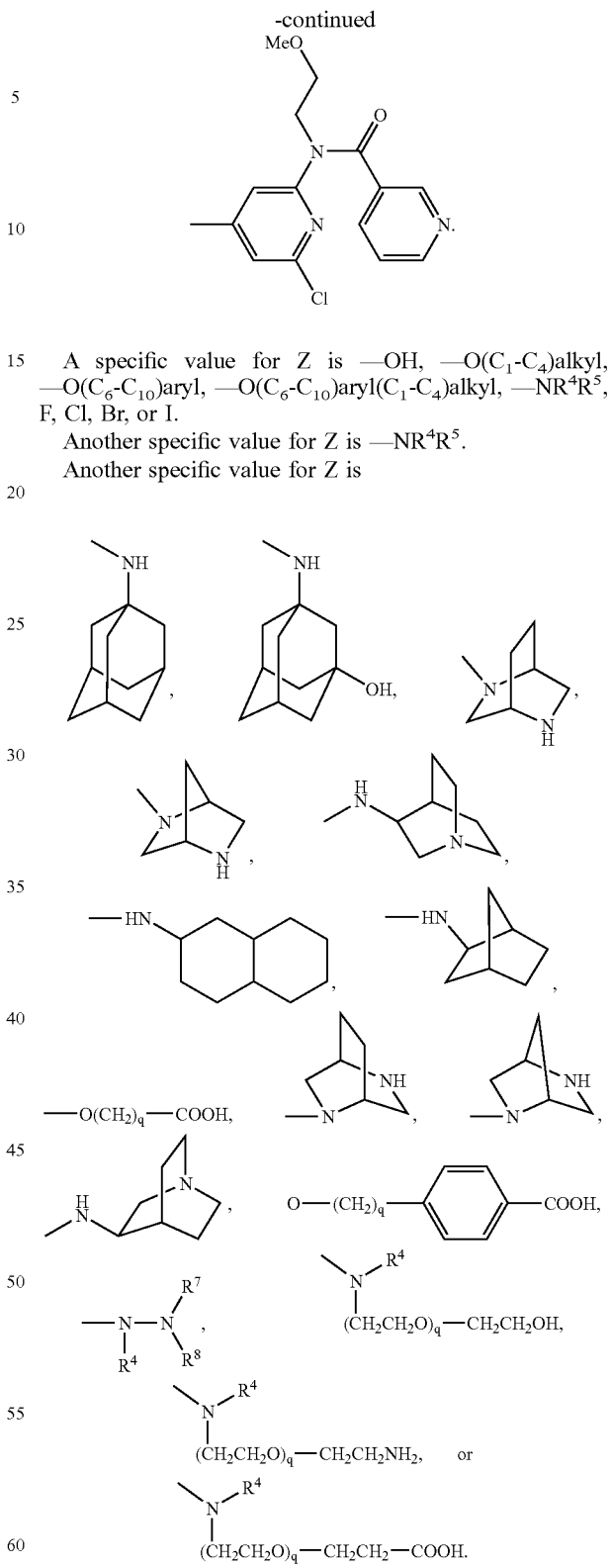

A specific value for Z is —OH, —O(C$_1$-C$_4$)alkyl, —O(C$_6$-C$_{10}$)aryl, —O(C$_6$-C$_{10}$)aryl(C$_1$-C$_4$)alkyl, —NR$^4$R$^5$, F, Cl, Br, or I.

Another specific value for Z is —NR$^4$R$^5$.

Another specific value for Z is

A specific value for R$^4$ is hydrogen, (C$_1$-C$_6$)alkyl, (C$_3$-C$_6$)cycloalkyl, (C$_3$-C$_6$)cycloalkyl(C$_1$-C$_4$)alkyl-, (C$_3$-C$_6$)heterocycle, (C$_6$-C$_{10}$)aryl, (C$_6$-C$_{10}$)aryl(C$_1$-C$_4$)alkyl-, (C$_5$-C$_6$)heteroaryl, or (C$_5$-C$_6$)heteroaryl(C$_1$-C$_4$)alkyl-, —S(O$_2$)NH$_2$, —C(O)R$^6$, —CO$_2$R$^6$, or C(O)NR$^6$R$^7$.

Another specific value for R⁴ is hydrogen, (C₁-C₄)alkyl, hydroxy(C₂-C₄)alkyl, (C₃-C₆)cycloalkyl, (C₆-C₁₀)aryl, (C₇-C₁₀)aralkyl, (C₅-C₆)heteroaryl, —(CH₂—CH₂—O)$_q$—(CH₂CH₂)—OR$^a$, —(CH₂—CH₂—O)$_q$—(CH₂—CH₂)—COOR$^a$, —(CH₂—CH₂—O)$_q$—(CH₂—CH₂)—NR$^a$R$^b$, —NR⁷R⁸, —C(O)R⁶, —CO₂R⁶, or —C(O)NR⁷R⁸.

Another specific value for R⁴ is hydrogen, methyl, ethyl, propyl, pentyl, hydroxyethyl, hydroxypropyl, ethoxyethyl, diethoxyethyl, methylbenzyl, aminomethylbenzyl, methoxybenzyl, methoxyphenethyl, furylmethyl, cyclopropyl, cyclopropylmethyl, cyclopentyl, cyclohexyl, thiophenyl, —C(O)R⁶, —CO₂R⁶, or —C(O)NHR⁷.

Another specific value for R⁴ is methyl, ethyl, cyclopropyl, cyclopropylmethyl, —C(O)R⁶, —CO₂R⁶, or —C(O)NHR⁷.

A specific value for R⁵ is hydrogen, (C₁-C₆)alkyl, (C₃-C₆)cycloalkyl, (C₃-C₆)cycloalkyl(C₁-C₄)alkyl-, (C₃-C₆)heterocycle, (C₆-C₁₀)aryl, (C₆-C₁₀)aryl(C₁-C₄)alkyl-, (C₅-C₆)heteroaryl, or (C₅-C₆)heteroaryl(C₁-C₄)alkyl-, —S(O₂)NH₂, —C(O)R⁶, —CO₂R⁶, or —C(O)NR⁶R⁷.

Another specific value for R⁵ is hydrogen, (C₁-C₄)alkyl, hydroxy(C₂-C₄)alkyl, (C₃-C₆)cycloalkyl, (C₆-C₁₀)aryl, (C₇-C₁₀)aralkyl, (C₅-C₆)heteroaryl, —(CH₂—CH₂—O)$_q$—(CH₂—CH₂)—OR$^a$, —(CH₂—CH₂—O)$_q$—(CH₂—CH₂)—COOR$^a$, —(CH₂—CH₂—O)$_q$—(CH₂—CH₂)—NR$^a$R$^b$, —NR⁷R⁸, —C(O)R⁶, —CO₂R⁶, or —C(O)NR⁷R⁸.

Another specific value for R⁵ is hydrogen, methyl, ethyl, propyl, pentyl, hydroxyethyl, hydroxypropyl, ethoxyethyl, diethoxyethyl, methylbenzyl, aminomethylbenzyl, methoxybenzyl, methoxyphenethyl, furylmethyl, cyclopropyl, cyclopropylmethyl, cyclopentyl, cyclohexyl, thiophenyl, —C(O)R⁶, —CO₂R⁶, or —C(O)NHR⁷.

Another specific value for R⁵ is methyl, ethyl, cyclopropyl, cyclopropylmethyl, —C(O)R⁶, —CO₂R⁶, or —C(O)NHR⁷.

A specific value for R⁴ and R⁵ taken together with the nitrogen to which they are attached, is a pyrrolidyl, piperidyl, piperazinyl, azepinyl, diazepinyl, morpholinyl, or thiomorpholinyl ring, each optionally substituted with 1, 2, 3, or 4 substituents independently selected from halo, cyano, nitro, —OR$^a$, —SR$^a$, (C₆-C₁₀)aryl, —O(C₆-C₁₀)aryl, hydroxy(C₁-C₈)alkyl, R$^b$R$^c$N(C₁-C₈)alkyl, halo(C₁-C₈)alkyl, —NR$^b$R$^c$, —C(O)R$^a$, —COOR$^a$, and —C(O)NR$^b$R$^c$.

A specific value for R⁶ is (C₁-C₆)alkyl, (C₃-C₆)cycloalkyl, (C₃-C₆)cycloalky(C₁-C₄)alkyl-, (C₃-C₆)heterocycle, (C₆-C₁₀)aryl, (C₆-C₁₀)aryl(C₁-C₄)alkyl-, (C₅-C₆)heteroaryl, or (C₅-C₆)heteroaryl(C₁-C₄)-alkyl-, each optionally substituted with 1, 2, or 3 substituents independently selected from halo, cyano, nitro, (C₁-C₈)alkyl, —OR$^a$, —SR$^a$, (C₆-C₁₀)aryl, —O(C₆-C₁₀)aryl, hydroxy(C₁-C₈)alkyl, R$^b$R$^c$N(C₁-C₈)alkyl, halo(C₁-C₈)alkyl, —NR$^b$R$^c$, —C(O)R$^a$, —COOR$^a$, and —C(O)NR$^b$R$^c$.

A specific value for R⁶ is (C₆-C₁₀)aryl, (C₅-C₆)heteroaryl, each optionally substituted with 1, 2, or 3 substituents independently selected from halo, cyano, nitro, (C₁-C₈)alkyl, halo(C₁-C₈)alkyl, —COOR$^a$, and —C(O)NR$^b$R$^c$.

A specific value for R⁶ is pyridyl, optionally substituted with F, Cl, Br, I, CF₃, cyano, nitro, —COOR$^a$, or —CONHR$^a$.

Another specific value for the compound is where R is hydrogen, methyl, or ethyl; R¹ and R² are independently methyl, ethyl, allyl, propargyl, i-propyl, n-propyl, cyclopropyl, cyclopropylmethyl, n-butyl; X is 3-pyridyl substituted in the 6 position with Z, wherein Z is (C₄-C₁₀)heterocycle or —NR⁴R⁵; R⁴ is methyl, ethyl, cyclopropyl, cyclopropylmethyl and R⁵ is —C(O)R⁶, wherein R⁶ is heteroaryl optionally substituted with 1, 2 or 3 substituents independently selected from halo, cyano, nitro, halo(C₁-C₈)alkyl, —C(O)R$^a$, —COOR$^a$, and —C(O)NR$^b$R$^c$, and wherein R$^a$, R$^b$ and R$^c$ are independently hydrogen, methyl, ethyl, propyl, isopropyl, or cyclopropyl.

The compounds of the invention can have the formula:

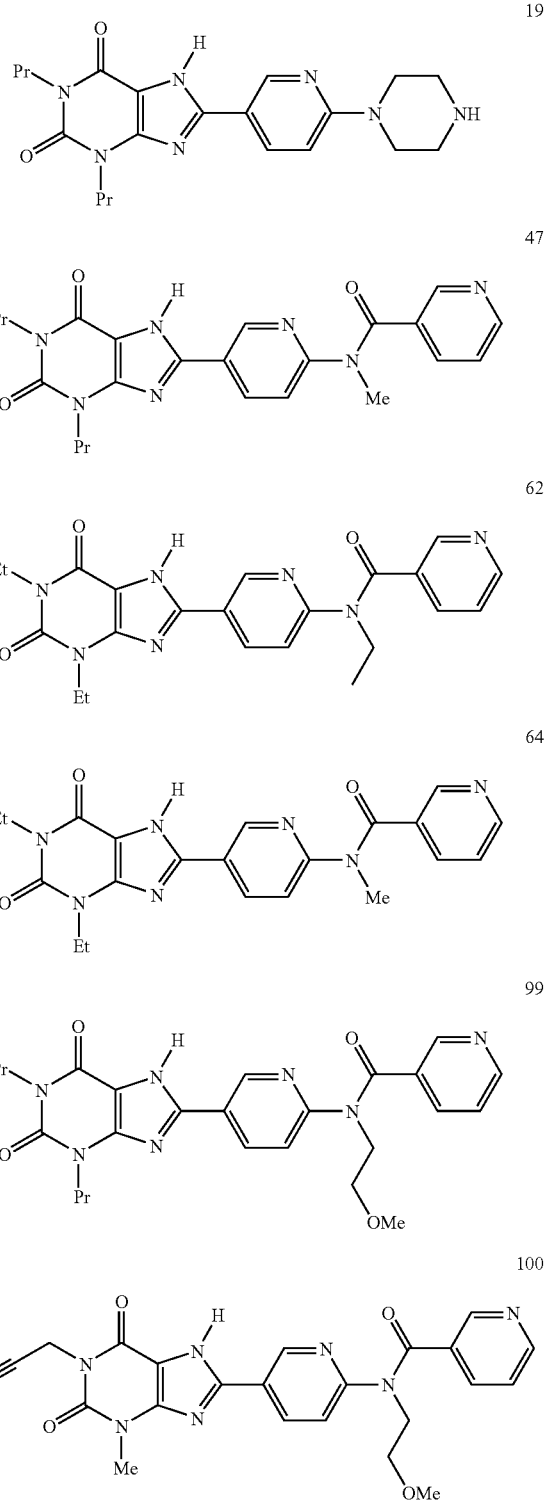

Aspects of the Invention:

The present invention provides a compound of formula I:

wherein:

R is hydrogen, $(C_1-C_5)$alkyl, halo$(C_1-C_8)$alkyl, $(C_3-C_5)$alkenyl, or $(C_3-C_5)$alkynyl;

$R^1$ and $R^2$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_4-C_{10})$heterocycle, $(C_4-C_{10})$heterocycle$(C_1-C_8)$alkyl-, $(C_6-C_{10})$aryl, $(C_6-C_{10})$aryl$(C_1-C_8)$alkyl-, $(C_5-C_{10})$heteroaryl, or $(C_5-C_{10})$heteroaryl$(C_1-C_8)$alkyl-;

X is a 5-10 member heteroaryl ring having one nitrogen atom and optionally interrupted by 1, 2, or 3 non-peroxide oxy (—O—), thio (—S—), sulfinyl (—SO—), sulfonyl (—S(O)$_2$—) or amine —N($R^9$)— groups;

Z is —OR$^3$, —SR$^3$, halo, —S(O)$_m$—NR$^4$R$^5$, —NR$^4$R$^5$, or $(C_4-C_{10})$heterocycle wherein the heterocycle is optionally substituted with 1, 2, 3, or 4 substituents independently selected from halo, cyano, nitro, —OR$^a$, —SR$^a$, $(C_1-C_8)$alkyl, $(C_6-C_{10})$aryl, —O($C_6-C_{10}$)aryl, hydroxy$(C_1-C_8)$alkyl, R$^b$R$^c$N$(C_1-C_8)$alkyl, halo$(C_1-C_8)$alkyl, —NR$^b$R$^c$, —C(O)R$^a$, —COOR$^a$, and —C(O)NR$^b$R$^c$;

each $Z^1$ is independently $(C_1-C_8)$alkyl, $(C_2-C_8)$alkenyl, $(C_2-C_8)$alkynyl, —OR$^6$, —SR$^6$, halo, R$^6$O($C_1-C_8$)alkyl, R$^7$R$^8$N($C_1-C_8$)alkyl, halo$(C_1-C_8)$alkyl, —NR$^7$R$^8$, R$^7$R$^8$N($C_1-C_8$)alkyl, —C(O)R$^6$, —COOR$^6$, and —C(O)NR$^7$R$^8$;

$R^3$ is $(C_1-C_8)$alkyl, $(C_3-C_8)$alkenyl, $(C_3-C_8)$alkynyl, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, —C(O)R$^6$, or —C(O)NR$^7$R$^8$;

$R^4$ and $R^5$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_6-C_{18})$polycycloalkyl, $(C_6-C_{18})$polycycloalkyl$(C_1-C_8)$alkyl-, $(C_3-C_{10})$heterocycle, $(C_3-C_{10})$heterocycle$(C_1-C_8)$alkyl-, —NR$^7$R$^8$, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, —$(C_2-C_4-Y)_q$—$(CH_2)_{2-4}$—$X^1$, —C(O)R$^6$, —CO$_2$R$^6$, —C(O)NR$^7$R$^8$, or —S(O)$_2$—NR$^7$R$^8$; or $R^4$ and $R^5$ together with the atoms to which they are attached form a saturated or partially unsaturated, mono-, bicyclic- or aromatic ring having 3, 4, 5, 6, 7, or 8, ring atoms and optionally comprising 1, 2, 3, or 4 heteroatoms selected from non-peroxide oxy (—O—), thio (—S—), sulfinyl (—SO—), sulfonyl (—S(O)$_2$—) and amine —N(R$^9$)— in the ring, and wherein the ring is optionally substituted with 1, 2, 3, or 4 substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$;

X$^1$ is —OR$^6$, —C(O)R$^6$, —CO$_2$R$^6$, or —NR$^7$R$^8$; and Y is oxy (—O—), thio (—S—), sulfinyl (—SO—), sulfonyl (—S(O)$_2$—) and amine —N(R$^9$)—;

wherein the alkyl, alkenyl, cycloalkyl, alkynyl, aryl, heterocycle, or heteroaryl groups of R$^1$, R$^2$, R$^3$, R$^4$ and R$^5$ groups are optionally substituted with one or more substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$;

wherein R$^6$ is hydrogen, (C$_1$-C$_8$)alkyl, R$^a$O(C$_1$-C$_8$)alkyl, R$^b$R$^c$N(C$_1$-C$_8$)alkyl, halo(C$_1$-C$_8$)alkyl, (C$_3$-C$_{10}$)heterocycle, (C$_3$-C$_{10}$)heterocycle(C$_1$-C$_8$)alkyl-, (C$_6$-C$_{10}$)aryl, (C$_6$-C$_{10}$)aryl(C$_1$-C$_8$)alkyl-, (C$_4$-C$_{10}$)heteroaryl, (C$_4$-C$_{10}$)heteroaryl(C$_1$-C$_8$)alkyl-; wherein the heterocycle, heteroaryl or aryl are optionally substituted with 1, 2, 3, or 4 substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$;

wherein R$^7$, R$^8$ and R$^9$ are independently hydrogen, (C$_1$-C$_8$)alkyl, R$^a$O(C$_1$-C$_8$)alkyl, R$^b$R$^c$N(C$_1$-C$_8$)alkyl, halo(C$_1$-C$_8$)alkyl, (C$_3$-C$_{10}$)heterocycle, (C$_6$-C$_{10}$)aryl, (C$_6$-C$_{10}$)aryl(C$_1$-C$_8$)alkyl-, (C$_4$-C$_{10}$)heteroaryl; —COOR$^a$, —C(O)R$^a$, or —C(O)NR$^b$R$^c$ wherein the heterocycle, heteroaryl or aryl are optionally substituted with 1, 2, 3, or 4 substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$; or R$^7$ and R$^8$ together with the atoms to which they are attached form a saturated or partially unsaturated, mono-, bicyclic- or aromatic ring having 3, 4, 5, 6, 7, or 8, ring atoms optionally ring having from 4 to eight ring atoms and optionally comprising 1, 2, 3, or 4 heteroatoms selected from non-peroxide oxy (—O—), thio (—S—), sulfinyl (—SO—), sulfonyl (—S(O)$_2$—) or amine —N(R$^b$)— in the ring;

R$^a$ is hydrogen, or (C$_1$-C$_6$)alkyl; R$^b$ and R$^c$ are each independently hydrogen, (C$_1$-C$_6$)alkyl, (C$_1$-C$_6$)alkoxy, (C$_3$-C$_8$)cycloalkyl, (C$_1$-C$_6$)alkylthio, (C$_6$-C$_{10}$)aryl, (C$_6$-C$_{10}$)aryl(C$_1$-C$_6$)alkyl-, heteroaryl, or heteroaryl (C$_1$-C$_6$)alkyl-; or R$^b$ and R$^c$ together with the nitrogen to which they are attached, form a pyrrolidyl, piperidyl, piperazinyl, azepinyl, diazepinyl, morpholinyl, or thiomorpholinyl ring; and where n is 0, 1, 2, 3, 4, 5, 6, 7, or 8; m is 1, or 2; and q is 1, 2, 3, or 4; or a pharmaceutically acceptable salt thereof.

In one aspect of the invention, R is hydrogen, methyl, ethyl, allyl, propargyl, i-propyl, n-propyl, n-butyl, i-butyl or halo(C$_1$-C$_4$)alkyl. In another aspect, R is hydrogen, methyl, ethyl, —CH$_2$—CH$_2$—Cl, —CH$_2$—CH$_2$—Br, or —CH$_2$—CH$_2$—CH$_2$—F. In one variation, R is hydrogen.

In one aspect of the invention, there is provided the above compound wherein R$^1$ is hydrogen, (C$_1$-C$_4$)alkyl, (C$_3$-C$_4$) alkenyl, (C$_3$-C$_4$)alkynyl, phenyl, or phenyl(C$_1$-C$_4$)alkyl. In another aspect, R$^1$ is (C$_3$-C$_6$)cycloalkyl and (C$_3$-C$_6$)cycloalkyl(C$_1$-C$_4$)alkyl-. In one variation, R$^1$ is cyclopropyl or cyclopropylmethyl. In another variation, R$^1$ is hydrogen, methyl, ethyl, allyl, propargyl, i-propyl, n-propyl, n-butyl, i-butyl, phenyl, phenethyl, benzyl, or (methoxyphenyl)ethyl. In yet another variation, R$^1$ is ethyl, n-propyl or allyl.

In one aspect of the invention, there is provided the above compound wherein R$^2$ is hydrogen, (C$_1$-C$_4$)alkyl, (C$_3$-C$_4$) alkenyl, (C$_3$-C$_4$)alkynyl, phenyl, phenyl(C$_1$-C$_4$)alkyl, or (methoxyphenyl)ethyl. In one variation, R$^2$ is (C$_3$-C$_6$)cycloalkyl or (C$_3$-C$_6$)cycloalkyl(C$_1$-C$_4$)alkyl-. In another variation, R$^2$ is cyclopropyl or cyclopropylmethyl. In another variation, R$^2$ is hydrogen, methyl, ethyl, allyl, propargyl, i-propyl, n-propyl, n-butyl, i-butyl, phenyl, phenethyl, or benzyl. In yet another variation, R$^2$ is ethyl, n-propyl or allyl.

In one aspect of the invention, there is provided the above compound wherein Z is —OH, —O(C$_1$-C$_4$)alkyl, —O(C$_6$-C$_{10}$)aryl, —O(C$_6$-C$_{10}$)aryl(C$_1$-C$_4$)alkyl, —NR$^4$R$^5$, F, Cl, Br, or I.

In another aspect of the invention, there is provided the above compound wherein R$^4$ is hydrogen, (C$_1$-C$_6$)alkyl, (C$_3$-C$_6$)cycloalkyl, (C$_3$-C$_6$)cycloalkyl(C$_1$-C$_4$)alkyl-, (C$_3$-C$_6$) heterocycle, (C$_6$-C$_{10}$)aryl, (C$_6$-C$_{10}$)aryl(C$_1$-C$_4$)alkyl-, (C$_5$-C$_6$)heteroaryl, or (C$_5$-C$_6$)heteroaryl(C$_1$-C$_4$)alkyl-, —S(O$_2$)NH$_2$, —C(O)R$^6$, —CO$_2$R$^6$, or —C(O)NR$^6$R$^7$. In one variation, R$^4$ is hydrogen, (C$_1$-C$_4$)alkyl, hydroxy(C$_2$-C$_4$) alkyl, (C$_3$-C$_6$)cycloalkyl, (C$_6$-C$_{10}$)aryl, (C$_7$-C$_{10}$)aralkyl, (C$_5$-C$_6$)heteroaryl, —(CH$_2$—CH$_2$—O)$_q$—(CH$_2$—CH$_2$)—OR$^a$, —(CH$_2$—CH$_2$—O)$_q$—(CH$_2$—CH$_2$)—COOR$^a$, —(CH$_2$—CH$_2$—O)$_q$—(CH$_2$—CH$_2$)—NR$^a$R$^b$, —NR$^7$R$^8$, —C(O)R$^6$, —CO$_2$R$^6$, or —C(O)NR$^7$R$^8$. In another variation, R$^4$ is hydrogen, methyl, ethyl, propyl, pentyl, hydroxyethyl, hydroxypropyl, ethoxyethyl, diethoxyethyl, methylbenzyl, aminomethylbenzyl, methoxybenzyl, methoxyphenethyl, furylmethyl, cyclopropyl, cyclopropylmethyl, cyclopentyl, cyclohexyl, thiophenyl, —C(O)R$^6$, —CO$_2$R$^6$, or —C(O)NHR$^7$. In yet another variation, R$^4$ is methyl, ethyl, cyclopropyl, cyclopropylmethyl, —C(O)R$^6$, —CO$_2$R$^6$, or —C(O)NHR$^7$.

In one aspect of the invention, there is provided the above compound wherein R$^5$ is hydrogen, (C$_1$-C$_6$)alkyl, (C$_3$-C$_6$) cycloalkyl, (C$_3$-C$_6$)cycloalkyl(C$_1$-C$_4$)alkyl-, (C$_3$-C$_6$)heterocycle, (C$_6$-C$_{10}$)aryl, (C$_6$-C$_{10}$)aryl(C$_1$-C$_4$)alkyl-, (C$_5$-C$_6$)heteroaryl, or (C$_5$-C$_6$)heteroaryl(C$_1$-C$_4$)alkyl-, —S(O$_2$)NH$_2$, —C(O)R$^6$, —CO$_2$R$^6$, or —C(O)NR$^6$R$^7$. In one variation, R$^5$ is hydrogen, (C$_1$-C$_4$)alkyl, hydroxy(C$_2$-C$_4$)alkyl, (C$_3$-C$_6$) cycloalkyl, (C$_6$-C$_{10}$)aryl, (C$_7$-C$_{10}$)aralkyl, (C$_5$-C$_6$)heteroaryl, —(CH$_2$—CH$_2$—O)$_q$—(CH$_2$—CH$_2$)—OR$^a$, —(CH$_2$—CH$_2$—O)$_q$—(CH$_2$—CH$_2$)—COOR$^a$, —(CH$_2$—CH$_2$—O)$_q$—(CH$_2$—CH$_2$)—NR$^a$R$^b$, —NR$^7$R$^8$, —C(O)R$^6$, —CO$_2$R$^6$, or —C(O)NR$^7$R$^8$. In another variation, R$^5$ is hydrogen, methyl, ethyl, propyl, pentyl, hydroxyethyl, hydroxypropyl, ethoxyethyl, diethoxyethyl, methylbenzyl, aminomethylbenzyl, methoxybenzyl, methoxyphenethyl, furylmethyl, cyclopropyl, cyclopropylmethyl, cyclopentyl, cyclohexyl, thiophenyl, —C(O)R$^6$, —CO$_2$R$^6$, or —C(O)NHR$^7$. In yet another variation, R$^5$ is methyl, ethyl, cyclopropyl, cyclopropylmethyl, —C(O)R$^6$, —CO$_2$R$^6$, or —C(O)NHR$^7$.

In one aspect of the invention, there is provided the above compound wherein R$^4$ and R$^5$ taken together with the nitrogen to which they are attached, is a pyrrolidyl, piperidyl, piperazinyl, azepinyl, diazepinyl, morpholinyl, or thiomorpholinyl ring, each optionally substituted with 1, 2, 3, or 4 substituents independently selected from halo, cyano, nitro, —OR$^a$, —SR$^a$, aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$.

In another aspect of the invention, there is provided the above compound wherein R$^6$ is (C$_1$-C$_6$)alkyl, (C$_3$-C$_6$)cycloalkyl, (C$_3$-C$_6$)cycloalky(C$_1$-C$_4$)alkyl-, (C$_3$-C$_6$)heterocycle, (C$_6$-C$_{10}$)aryl, (C$_6$-C$_{10}$)aryl(C$_1$-C$_4$)alkyl-, (C$_5$-C$_6$)heteroaryl, or (C$_5$-C$_6$)heteroaryl(C$_1$-C$_4$)-alkyl-, each optionally substituted with 1, 2, or 3 substituents independently selected from halo, cyano, nitro, (C$_1$-C$_8$)alkyl, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$. In one variation, R$^6$ is (C$_6$-C$_{10}$)aryl, (C$_5$-C$_6$)heteroaryl, each optionally substituted with 1, 2, or 3 substituents independently selected from halo, cyano, nitro, (C$_1$-C$_8$)alkyl, halo(C$_1$-C$_8$)alkyl, —COOR$^a$, and —C(O)NR$^b$R$^c$. In another variation, R$^6$ is pyridyl, optionally substituted with F, Cl, Br, I, CF$_3$, cyano, nitro, —COOR$^a$, or —CONHR$^a$.

Another specific value for the compound is where R is hydrogen, methyl, or ethyl; R$^1$ and R$^2$ are independently methyl, ethyl, allyl, propargyl, i-propyl, n-propyl, cyclopropyl, cyclopropylmethyl, or n-butyl; X is 3-pyridyl substituted in the 6 position with Z, wherein Z is (C$_4$-C$_{10}$) heterocycle or —NR$^4$R$^5$; R$^4$ is methyl, ethyl, cyclopropyl, cyclopropylmethyl and R$^5$ is —C(O)R$^6$, wherein R$^6$ is heteroaryl optionally substituted with 1, 2 or 3 substituents independently selected from halo, cyano, nitro, halo(C$_1$-C$_8$)alkyl, —C(O)R$^a$, —COOR$^a$, and —C(O)NR$^b$R$^c$, and wherein R$^a$, R$^b$ and R$^c$ are independently hydrogen, methyl, ethyl, propyl, isopropyl, or cyclopropyl.

In another aspect of the invention, there is provided the above compound wherein R is hydrogen, methyl, ethyl, allyl, propargyl, i-propyl, n-propyl, n-butyl, i-butyl or halo (C$_1$-C$_4$)alkyl; and R$^1$ and R$^2$ are independently hydrogen, methyl, ethyl, allyl, propargyl, i-propyl, n-propyl, cyclopropyl, cyclopropylmethyl, n-butyl, i-butyl, phenyl, phenethyl, or benzyl. In one variation, R is hydrogen, methyl, ethyl, —CH$_2$—CH$_2$—Cl, —CH$_2$—CH$_2$—Br, or —CH$_2$—CH$_2$—CH$_2$—F; and R$^1$ and R$^2$ are independently hydrogen, methyl, ethyl, allyl, propargyl, i-propyl, n-propyl, cyclopropyl, cyclopropylmethyl, or (methoxyphenyl)ethyl.

In one aspect of the invention, there is provided the above compound wherein X is imidazolyl, triazolyl, triazinyl, oxazoyl, isoxazoyl, thiazolyl, isothiazoyl, thiodiazolyl, pyrrolyl, pyrazinyl, tetrazolyl, pyridinyl, pyrimidinyl, indolyl, isoquinolyl, or quinolyl, each optionally substituted with 1, 2, or 3 substituents independently selected from halo, cyano, nitro, (C$_1$-C$_8$)alkyl, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo (C$_1$-C$_8$)alkyl, —NR$^b$R$^c$, —C(O)R$^a$, —COOR$^a$, and —C(O)NR$^b$R$^c$. In one variation of the above, X is 2-pyridinyl, 3-pyridinyl, or 4-pyridinyl, each optionally substituted with 1, 2, or 3 substituents independently selected from the group consisting of halo, cyano, nitro, (C$_1$-C$_8$)alkyl, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$. In another variation, —X(Z$^1$)$_n$-Z has the formula:

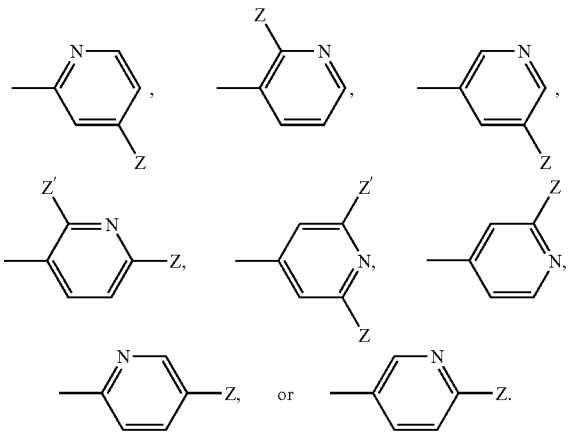

In another variation, —X(Z$^1$)$_n$-Z has the formula

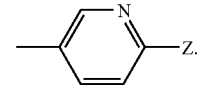

In one aspect of the invention, there is provided the above compound wherein Z is —OH, —O(C$_1$-C$_4$)alkyl, —OC(O)NR$^4$R$^8$, (C$_1$-C$_4$)alkyl, —NR$^4$R$^5$, F, Cl, Br, or I, wherein R$^4$ and R$^5$ are independently hydrogen, (C$_1$-C$_6$)alkyl, (C$_3$-C$_6$)cycloalkyl, (C$_3$-C$_6$)heterocycle, (C$_6$-C$_{10}$)aryl, (C$_7$-C$_{12}$)aralkyl, (C$_5$-C$_6$)heteroaryl, or (C$_5$-C$_6$)heteroaryl(C$_1$-C$_4$)alkyl, —S(O$_2$)NH$_2$, —C(O)R$^6$, —CO$_2$R$^6$, or —C(O)NR$^6$R$^7$. In one variation, Z is —NR$^4$R$^5$.

In one aspect of the invention, there is provided the above compound wherein R$^4$ and R$^5$ together with the nitrogen to which they are attached, form a pyrrolidyl, piperidyl, piperazinyl, azepinyl, diazepinyl, morpholinyl, or thiomorpholinyl ring, wherein the ring is optionally substituted with 1, 2, 3, or 4 substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)alkyl, R$^b$R$^c$N(C$_1$-C$_8$)alkyl, halo(C$_1$-C$_8$)alkyl, —NR$^b$R$^c$, —C(O)R$^a$, —COOR$^a$, and —C(O)NR$^b$R$^c$. In one variation of the above, R$^4$ and R$^5$ are independently hydrogen, (C$_1$-C$_4$)alkyl, hydroxy(C$_2$-C$_4$)alkyl, (C$_3$-C$_6$)cycloalkyl, (C$_6$-C$_{10}$)aryl, (C$_7$-C$_{10}$)aralkyl, (C$_5$-C$_6$)heteroaryl, —(CH$_2$—CH$_2$—O)$_q$—(CH$_2$—CH$_2$)—OR$^a$, —(CH$_2$—CH$_2$—O)$_q$—(CH$_2$—CH$_2$)—COOR$^a$, —(CH$_2$—CH$_2$—O)$_q$—(CH$_2$—CH$_2$)—NR$^a$R$^b$, —NR$^7$R$^8$, —C(O)R$^6$, —CO$_2$R$^6$, or —C(O)NR$^7$R$^8$. In another variation, R$^4$ and R$^5$ are independently hydrogen, methyl, ethyl, propyl, pentyl, hydroxyethyl, hydroxypropyl, ethoxyethyl, diethoxyethyl, methylbenzyl, aminomethylbenzyl, methoxybenzyl, methoxyphenethyl, furylmethyl, cyclopentyl, cyclohexyl, thiophenyl, —C(O)R$^6$, —CO$_2$R$^6$, or —C(O)NHR$^7$. In yet another variation, R$^6$ is methyl, methoxy, or pyridyl, and R$^7$ is phenyl, fluorophenyl, or methoxyphenyl.

In one aspect of the invention, there is provided the above compound wherein R is hydrogen, methyl, or ethyl; R$^1$ and R$^2$ are independently methyl, ethyl, allyl, propargyl, i-propyl, n-propyl, cyclopropyl, cyclopropylmethyl, n-butyl, i-butyl; and Z is (C$_4$-C$_{10}$)heterocycle wherein the heterocycle is optionally substituted with 1, 2, 3, or 4 substituents independently selected from halo, cyano, nitro, —OR$^a$, —SR$^a$, (C$_6$-C$_{10}$)aryl, —O(C$_6$-C$_{10}$)aryl, hydroxy(C$_1$-C$_8$)

alkyl, $R^bR^cN(C_1$-$C_8)$alkyl, halo$(C_1$-$C_8)$alkyl, —$NR^bR^c$, —$C(O)R^a$, —$COOR^a$, and —$C(O)NR^bR^c$.
In one aspect of the invention, there is provided the above compound wherein Z is selected from the group consisting of:
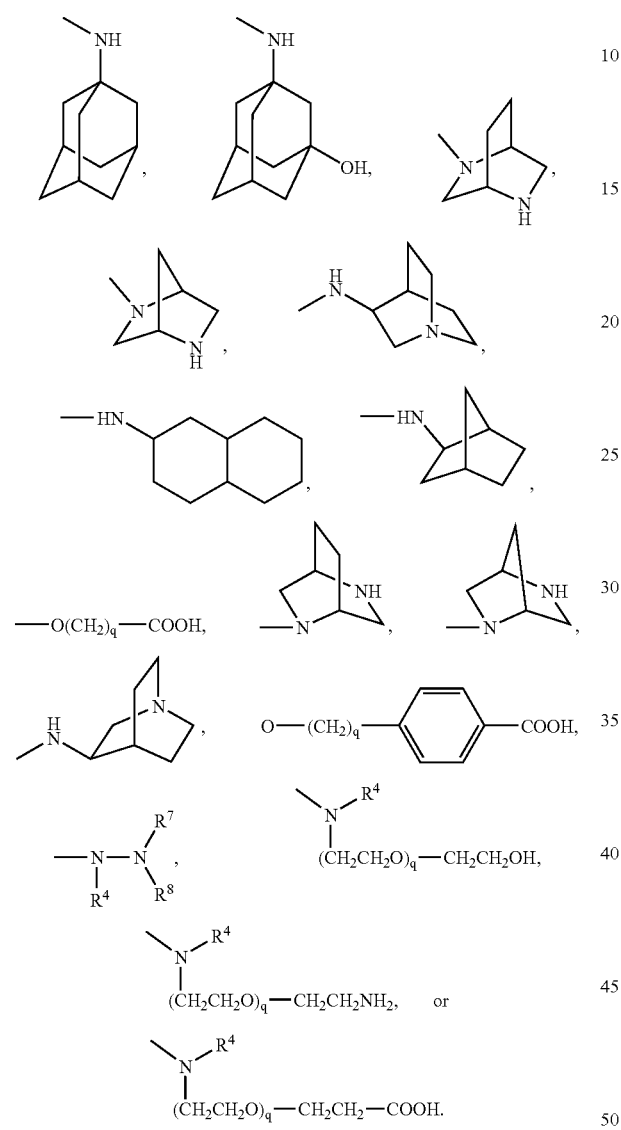
In one variation of the above, —$X(Z^1)_n$-Z is selected from the group consisting of:
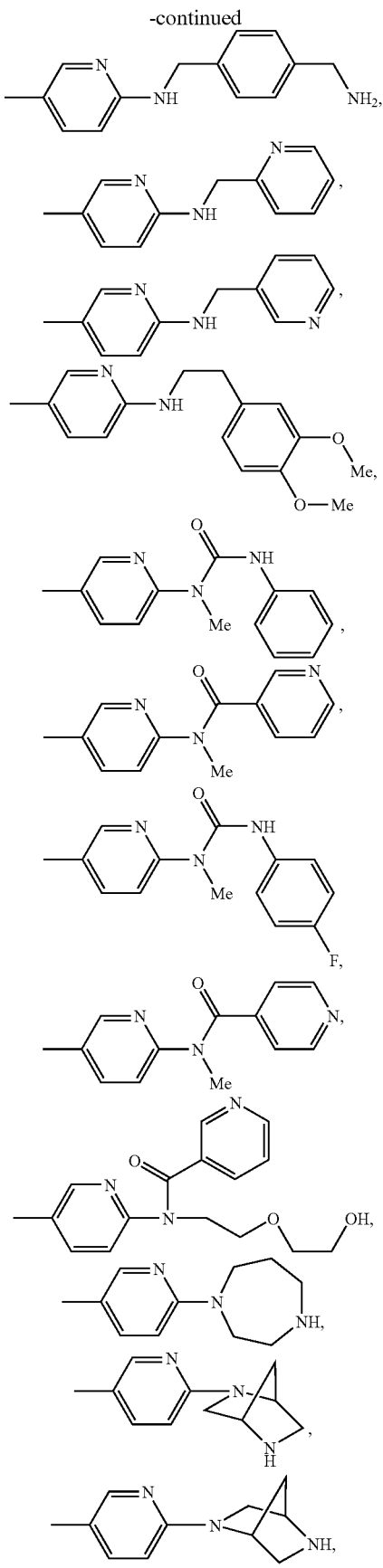

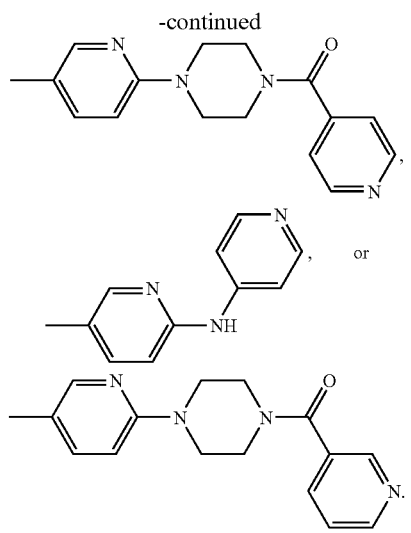
In another variation, $R^1$ and $R^2$ are n-propyl; R is hydrogen and n is zero.
In one aspect of the invention, there is provided the above compound wherein $-X(Z^1)_n-Z$ is selected from the group consisting of:
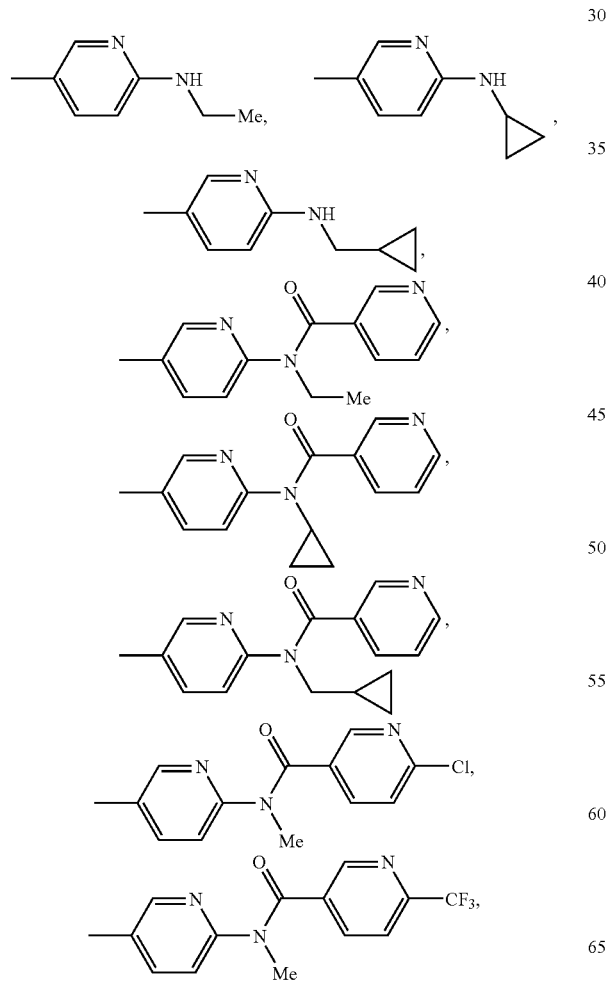
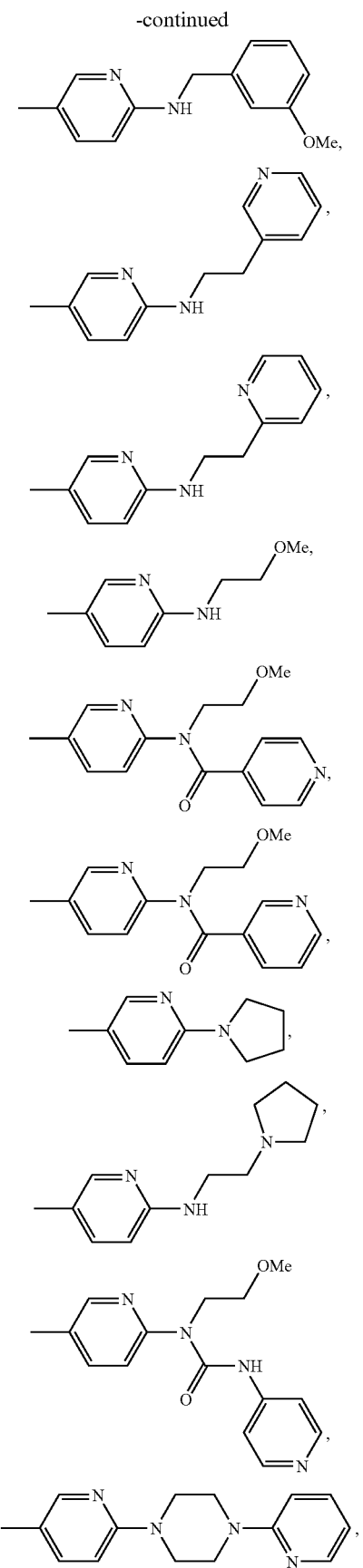

-continued

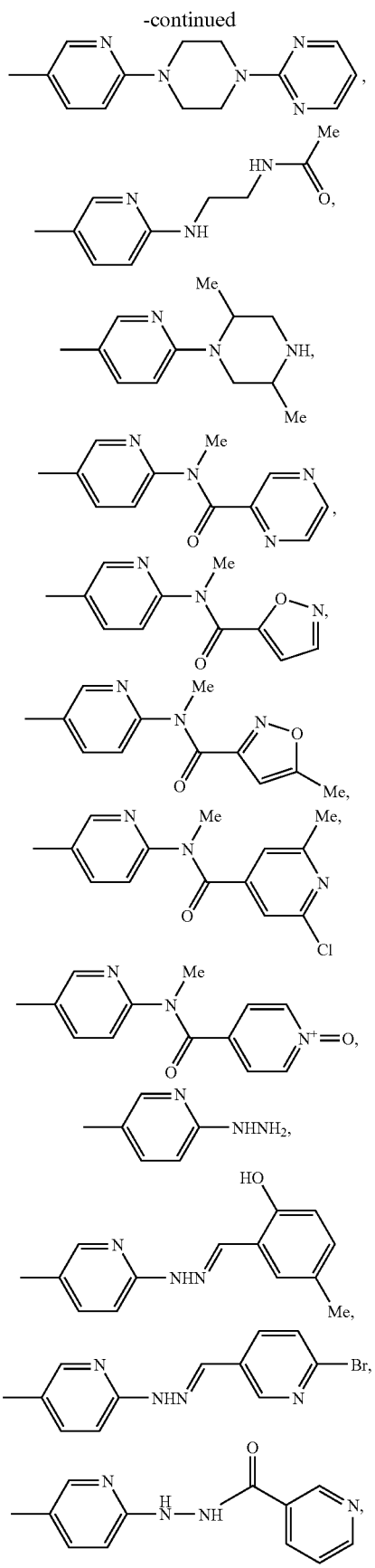

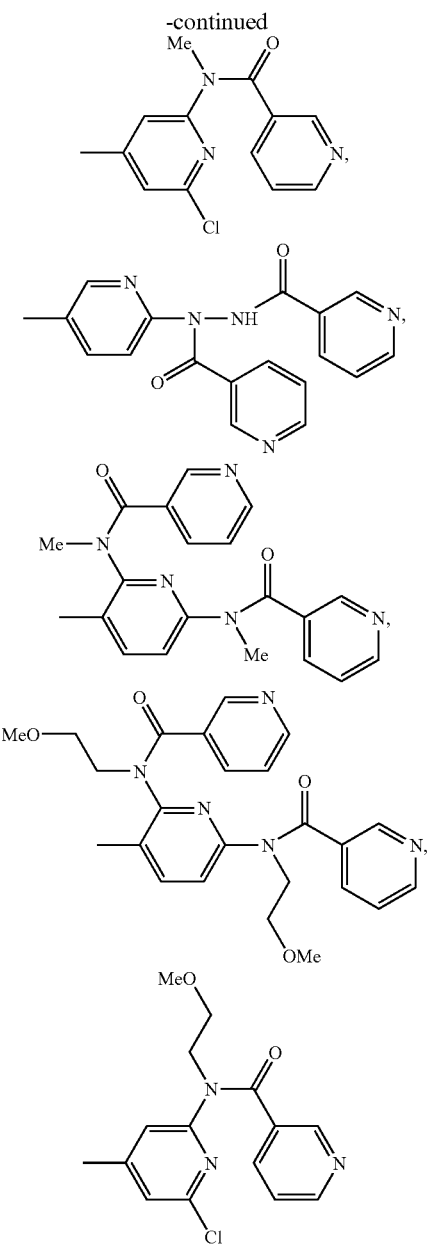

In one aspect of the invention, there is provided the compound selected from the group consisting of:
1,3-Dipropyl-8-(6-chloro-3-pyridyl)xanthine;
1-Propyl-3-propargyl-8-(6-chloro-3-pyridyl)xanthine;
1,3-Dipropyl-8-(6-ethylamino-3-pyridyl)xanthine;
1,3-Dipropyl-8-(6-(2-hydroxyethyl)amino-3-pyridyl)xanthine;
1,3-Dipropyl-8-[6-(4-acetylpiperazinyl)-3-pyridyl]xanthine;
1,3-Dipropyl-8-[6-(benzylamino)-3-pyridyl]xanthine;
1,3-Dipropyl-8-[6-(1-piperidinyl)-3-pyridyl]xanthine;
1,3-Dipropyl-8-(6-pyrrolidinylpyrid-3-yl)xanthine;
1,3-Dipropyl-8-{6-[4-methyl(perhydro-1,4-diazaepin-1-yl)]-3-pyridyl}xanthine;
1,3-Dipropyl-8-(6-methylamino-3-pyridyl)xanthine;
1,3-Dipropyl-8-[6-(4-methoxybenzylamino)-3-pyridyl]xanthine;

1,3-Dipropyl-8-[6-(3-methylpiperidino)-3-pyridyl]xanthine;
1,3-Dipropyl-8-[6-(2-hydroxypropyl)amino-3-pyridyl]xanthine;
1,3-Dipropyl-8-[6-(2,2-dimethoxyethyl)amino-3-pyridyl]xanthine;
1,3-Dipropyl-8-[6-(1-hydroxy-2-propyl)amino-3-pyridyl]xanthine;
1,3-Dipropyl-8-(6-morpholino-3-pyridyl)xanthine;
1,3-Dipropyl-8-(6-dimethylamino-3-pyridyl)xanthine;
1,3-Dipropyl-8-[[6-(2-hydroxyethoxy)ethylamino]-3-pyridy]xanthine;
1,3-Dipropyl-8-(6-piperazino-3-pyridyl)xanthine;
1,3-Dipropyl-8-[6-(2-hydroxy-2-phenylethyl)amino-3-pyridyl]xanthine;
1,3-Dipropyl-8-[6-(4-aminomethylbenzylamino)-3-pyridyl]xanthine;
1,3-Dipropyl-8-(6-phenylamino-3-pyridyl]xanthine;
1,3-Dipropyl-8-(6-cyclopropylamino-3-pyridyl]xanthine;
1,3-Dipropyl-8-[6-(6-pyridylmethylamino)-3-pyridyl]xanthine;
1,3-Dipropyl-8-(6-(4-methylpiperazino)-3-pyridyl)xanthine;
1,3-Dipropyl-8-[6-(3-pyridylmethylamino)-3-pyridyl]xanthine;
1,3-Dipropyl-8-[6-(2-methylbenzylamino)-3-pyridyl]xanthine;
1,3-Dipropyl-8-[6-[2-(3,4-dimethoxyphenyl)ethylamino]-3-pyridyl]xanthine;
1,3-Dipropyl-8-[6-[(N-propylcarbamoyl), methylamino]-3-pyridyl)xanthine;
1,3-Dipropyl-8-[6-(3-pentylamino)-3-pyridyl]xanthine;
1,3-Dipropyl-8-[6-(2,2-diphenylethylamino)-3-pyridyl]xanthine;
1,3-Dipropyl-8-[6-[2-(1-ethylpyrrolidinomethylamino)]-3-pyridyl]xanthine;
1,3-Dipropyl-8-[6-(3-methoxybenzylamino)-3-pyridyl]xanthine;
1,3-Dipropyl-8-[6-[(N-phenylcarbamoyl)methylamino]-3-pyridyl)xanthine;
1,3-Dipropyl-8-[6-(furfurylamino)-3-pyridyl]xanthine;
1,3-Dipropyl-8-[6-[2-(4-methoxyphenyl)ethylamino]-3-pyridyl]xanthine;
1,3-Dipropyl-8-[6-(2-methoxybenzylamino)-3-pyridyl]xanthine;
1,3-Dipropyl-8-[6-(propylamino)-3-pyridyl]xanthine;
1,3-Dipropyl-8-[6-(cyclopentylamino)-3-pyridyl]xanthine;
1,3-Dipropyl-8-[6-(cyclohexylamino)-3-pyridyl]xanthine;
1,3-Dipropyl-7-ethyl-8-(6-chloro-3-pyridyl)xanthine;
1,3-Dipropyl-7-(3-fluoropropyl-8-(6-chloro-3-pyridyl)xanthine;
1,3-Dipropyl-7-methyl-8-(6-chloro-3-pyridyl)xanthine;
1,3-Dipropyl-7-(2-bromoethyl)-8-(6-chloro-3-pyridyl)xanthine;
1,3-Dipropyl-8-[6-(2-thiophenemethylamino)-3-pyridyl]xanthine;
1,3-Dipropyl-8-[6-[(N-(4-methoxyphenylcarbamoyl)methylamino]-3-pyridyl)xanthine;
1,3-Dipropyl-8-[6-[N-nicotinoylmethylamino]-3-pyridyl)xanthine;
1,3-Dipropyl-8-[6-[(N-(4-fluorophenylcarbamoyl)methylamino]-3-pyridyl)xanthine;
1,3-Dipropyl-8-[6-[N-isonicotinoylmethylamino]-3-pyridyl)xanthine;
1,3-Dipropyl-8-[6-[N-methoxycarbonylmethylamino]-3-pyridyl)xanthine;
1,3-Dipropyl-8-[6-[N-phenylcarbamoyl, N-(2 phenylcarbamoyloxyethyl)amino]-3-pyridyl)xanthine;
1,3-Dipropyl-8-{6-[4-(N-phenylcarbamoyl)]piperazino-3-pyridyl}xanthine;
1,3-Dipropyl-8-{6-[4-(N-isonicotinoyl)]piperazino-3-pyridyl}xanthine;
1-propyl-3-(4-methoxyphenyl)ethyl-8-(6-chloro-3-pyridyl)xanthine;
1-Propyl-3-(methoxyphenylethyl)-8-(6-piperazino-3-pyridyl)xanthine;
1,3-Dipropyl-8-[6-(4-pyridylamino)-3-pyridyl]xanthine;
1,3-Dipropyl-8-{6-[4-(N-nicotinoyl)]piperazino-3-pyridyl}xanthine;
1,3-Dipropyl-8-[6-(hexahydro-1,4-diazaepin-1-yl)-3-pyridyl]xanthine;
1,3-Diethyl-8-(6-chloro-3-pyridyl)xanthine;
1,3-Diethyl-8-(6-piperazino-3-pyridyl)xanthine;
1,3-Diethyl-8-[6-[(N-phenylcarbamoyl)methylamino-3-pyridyl)xanthine;
1,3-Diethyl-8-[6-[N-nicotinoylethylamino]-3-pyridyl)xanthine;
1,3-Diethyl-8-(6-methylamino-3-pyridyl)xanthine;
1,3-Diethyl-8-[6-[N-nicotinoylmethylamino]-3-pyridyl)xanthine;
1,3-Diethyl-8-[6-[N-nicotinoylcyclopropylamino]-3-pyridyl)xanthine;
1,3-Dicyclopropylmethyl-8-(6-methylaminopyridin-3-yl)xanthine;
1-Propargyl-3-methyl-8-(6-methylamino-3-pyridyl)xanthine;
8-[6-(2,5-diaza-bicyclo[2.2.2]oct-2-yl)-pyridin-3-yl}-1,3-dipropyl-3,7-dihydro-purine-2,6-dione;
1,3-Dicylopropylmethyl-8-[6-[N-nicotinoylmethylamino]-3-pyridyl)xanthine;
1,3-Dicylopropylmethyl-8-[6-[N-nicotinoylethylamino]-3-pyridyl)xanthine;
1,3-Diallyl-8-(6-methylamino-3-pyridyl)xanthine;
1-Clopropylmethyl-3-ethyl-8-(6-methylaminopyridin-3-yl)xanthine;
1,3-Diethyl-8-[6-(2-pyridylmethylamino)-3-pyridyl]xanthine;
1,3-Diethyl-8-[6-(3-pyridylmethylamino)-3-pyridyl]xanthine;
1,3-Diethyl-8-[6-(3-methoxybenzylamino)-3-pyridyl]xanthine;
1,3-Dipropyl-8-[6-[2-(3-pyridyl)-ethylamino-3-pyridyl]xanthine;
1,3-Diethyl-8-[6-[2-(3-pyridyl)-ethylamino)-3-pyridyl]xanthine;
1,3-Dipropyl-8-[6-[2-(2-pyridyl)-ethylamino]-3-pyridyl]xanthine;
1,3-Diethyl-8-[6-[2-(2-pyridyl)-ethylamino)-3-pyridyl]xanthine;
1,3-Diethyl-8-(6-pyrrolidinylpyrid-3-yl)xanthine;
1,3-Diethyl-8-[6-[2-(1-pyrrolidinyl)-ethylamino)-3-pyridyl]xanthine;
1,3-Dipropyl-8-(6-(2-methoxyethyl)amino-3-pyridyl)xanthine;
1,3-Dipropyl-8-(6-(2-acetylaminoethyl)amino-3-pyridyl)xanthine;
1,3-Diethyl-8-(6-bromo-3-pyridyl)xanthine;
1,3-Dipropyl-8-{6-[4-(2-pyridyl)-piperazino]-3-pyridyl}xanthine;
1,3-Diethyl-8-{6-[4-(2-pyridyl)-piperazino]-3-pyridyl}xanthine;
1,3-Diethyl-8-[6-(trans-2,5-dimethylpiperazino)-3-pyridyl]xanthine;

1,3-Dipropyl-8-{6-[4-(2-pyrimidinyl)-piperazino]-3-pyridyl}xanthine;
1,3-Diethyl-8-{6-[4-(2-pyrimidinyl)-piperazino]-3-pyridyl)xanthine;
1,3-Diethyl-8-(6-(2-methoxyethyl)amino-3-pyridyl)xanthine;
1-Propargyl, 3-methyl-8-(6-Bromo-3-pyridyl)xanthine;
1,3-Diethyl-8-[6-[N-nicotinoyl, N-(2-methoxyethyl)amino]-3-pyridyl)xanthine;
1-Propargyl, 3-methyl-8-(6-(2-methoxyethyl)-3-pyridyl)xanthine;
1,3-Diethyl-8-[6-[N-isonicotinoyl, N-(2-methoxyethyl)amino]-3-pyridyl)xanthine;
1-(5-(1,3-Diethyl-2,3,6,7-tetrahydro-2,6-dioxo-1H-purin-8-yl)pyridin-2-yl)-1-(2-methoxyethyl)-3-(pyridine-4-yl)urea;
1,3-Dimethyl-8-(6-bromo-3-pyridyl)xanthine;
1,3-Dimethyl-8-(6-methylamino-3-pyridyl)xanthine;
1,3-Dimethyl-8-[6-[N-nicotinoylmethylamino]-3-pyridyl)xanthine;
1,3-Dipropyl-8-[6-[N-nicotinoyl, N-(2-methoxyethyl)amino]-3-pyridyl)xanthine;
1-Propargyl, 3-methyl-8-[6-[N-nicotinoyl, N-(2-methoxyethyl)amino)-3-pyridyl)xanthine;
1-Propargyl, 3-methyl-8-[6-[N-nicotinoylmethylamino]-3-pyridyl)xanthine;
1,3-Dipropyl-8-(2,6-dichloro-3-pyridyl)xanthine;
1,3-Dipropyl-8-(2,6-dimethylamino-3-pyridyl)xanthine;
1,3-Dipropyl-8-(2,6-di(2-methoxyethyl)-3-pyridyl)xanthine;
1,3-Dipropyl-8-[2,6-d][N-nicotinoylmethylamino]-3-pyridyl)xanthine;
1,3-Dipropyl-8-[2,6-d][N-nicotinoyl, N-methoxyethyl]-3-pyridyl)xanthine;
1,3-Diethyl-8-[6-[N-(2-pyrazinecarbonyl)methylamino]-3-pyridyl)xanthine;
1,3-Diethyl-8-[6-[N-(isoxazole-5-carbonyl)methylamino]-3-pyridyl)xanthine;
1,3-Dipropyl-8-[6-[N-(2-pyrazinecarbonyl)methylamino]-3-pyridyl)xanthine;
1,3-Dipropyl-8-[6-[N-(isoxazole-5-carbonyl)methylamino]-3-pyridyl)xanthine;
1,3-Dipropyl-8-[6-[N-(5-methylisoxazol-3-yl-3-carbonyl)methylamino]-3-pyridyl)xanthine;
1,3-Dipropyl-8-[6-[N-(2-chloro-6-methoxypyridinyl-4-carbonyl),N-methylamino]-3-pyridyl)xanthine;
1,3-Dipropyl-8-[6-[N-(Isonicotinoyl N-oxide),N-methylamino]-3-pyridyl)xanthine;
1-propyl-3-(4-methoxyphenyl)ethyl-8-(6-methylamino-3-pyridyl)xanthine;
1,3-Diethyl-8-[6-[N-(Isonicotinoyl N-oxide),N-methylamino]-3-pyridyl)xanthine;
1,3-Diallyl-8-(6-chloro-3-pyridyl)xanthine;
1-propyl-3-(4-methoxyphenyl)ethyl-8-[6-(N-nicotinoylmethylamino)-3-pyridyl]xanthine;
1-propyl-3-(4-methoxyphenyl)ethyl-8-[6-(N-(6-chloronicotinoyl)methylamino)-3-pyridyl]xanthine;
1,3-diallyl-8-[6-(N-nicotinoylmethylamino)-3-pyridyl]xanthine;
1,3-diallyl-8-[6-(N-(6-chloronicotinoyl)methylamino)-3-pyridyl]xanthine;
1,3-dipropyll-8-]-8-[6-(N-[6-(trifluoromethyl)nicotinoyl]methylamino)-3-pyridyl]xanthine;
1,3-diethyl-8-[6-(2-hydroxy-5-methyl)benzaldehydehydrazono]-3-pyridyl]xanthine;
1-Cyclopropyl-3-propyl-8-[6-(N-[6-(trifluoromethyl)nicotinoyl]methylamino)-3-pyridyl]xanthine;
1,3-diethyl-8-[6-(bromopyridine-3-carbaldehydehydrazono]-3-pyridyl]xanthine;
1-Cyclopropyl-3-ethyl-8-(6-methylamino-3-pyridyl)xanthine;
1-Cyclopropyl-3-propyl-8-(6-methylamino-3-pyridyl)xanthine;
1-Propyl-3-cyclopropyl-8-(6-methylamino-3-pyridyl)xanthine;
1-Cyclopropyl-3-propyl-8-(6-(2-methoxyethyl)amino-3-pyridyl)xanthine;
1-Cyclopropyl-3-propyl-8-[6-[N-nicotinoylmethylamino]-3-pyridyl)xanthine;
1,3-Diethyl-8-[6-(N-(6-chloronicotinoyl)methylamino)-3-pyridyl]xanthine;
1,3-Dipropyl-8-(2-chloro-6-methoxyethylamino-4-pyridyl)xanthine;
1,3-Dipropyl-8-(2-chloro-6-methylamino-4-pyridyl)xanthine;
1,3-Dipropyl-8-[2-[N-nicotinoyl, N-(2-methoxyethyl)amino]-6-chloro-4-pyridyl)xanthine;
1,3-Dipropyl-8-[2-[N-nicotinoyl, N-methylamino]-6-chloro-4-pyridyl)xanthine;
1-Cyclopropyl-3-propyl-8-[6-[N-(6-chloronicotinoyl)methylamino]-3-pyridyl)xanthine;
1-Ethyl-3-cyclopropyl-8-(6-methylamino-3-pyridyl)xanthine;
1-Ethyl-3-cyclopropyl-8-(6-(2-methoxyethyl)amino-3-pyridyl)xanthine;
1,3-Diethyl-8-[6-hydrazino-3-pyridyl]xanthine;
1,3-Diethyl-8-[6-(cyclopropylamino)-3-pyridyl]xanthine;
1,3-Diethyl-8-[6-(cyclopropylmethylamino)-3-pyridyl]xanthine;
N'-[5-(1,3-diethyl-2,6-dioxo-2,3,6,7-tetrahydro-1H-purin-8-yl)-pyridin-2-yl]-hydrazide;
N-[5-(1,3-diethyl-2,6-dioxo-2,3,6,7-tetrahydro-1H-purin-8-yl)-pyridin-2-yl]-N'-(pyridine-3-carbonyl)-hydrazide;
1,3-Diethyl-8-[6-(ethylamino)-3-pyridyl]xanthine;
1,3-Diethyl-8-[6-[N-nicotinoylcyclopropylmethylamino]-3-pyridyl)xanthine; and
1-Cyclopropylmethyl-3-ethyl-8-[6-[N-(6-chloronicotinoyl)methylamino]-3-pyridyl)xanthine;

or a pharmaceutical acceptable salt thereof, optionally in the form of a single stereoisomer or mixture of stereoisomers thereof.

In one aspect of the invention, there is provided a pharmaceutical composition comprising: (a) a therapeutically effective amount of a compound described above; and (b) a pharmaceutically acceptable excipient. In another aspect, there is provided a pharmaceutical composition comprising: (a) a therapeutically effective amount of a compound of the above; and (b) a pharmaceutically acceptable excipient.

In one aspect of the invention, there is provided a therapeutic method for preventing or treating a pathological condition or symptom in a mammal, wherein the activity of adenosine $A_{2B}$ receptors is implicated and antagonism of its action is desired comprising administering to the mammal an effective amount of a compound of the present invention. In another aspect of the invention, there is provided a method for treating asthma, allergies, allergic diseases or an autoimmune disease comprising administering an effective amount of a compound of the present invention to a mammal in need of such treatment.

In yet another aspect of the invention, there is provided a method for treating diarrheal diseases, insulin resistance, diabetes, cancer, ischemia/reprefusion injuries, diabetic retinopathy or hyperbaric oxygen-induced retinopathy, comprising administering an effective amount of a compound of the present invention or a pharmaceutically acceptable salt thereof to a mammal in need of such treatment. In yet another aspect, there is provided a therapeutic method for preventing or treating a pathological condition or symptom in a mammal, wherein the activity of adenosine $A_{2B}$ receptors is implicated and antagonism of its action is desired comprising administering to the mammal an effective amount of a compound of the present invention.

In another aspect of the invention, there is provided the compound of the present invention for use in medical therapy. In another aspect, there is provided a use of a compound of the invention, for the manufacture of a medicament useful for the treatment of a disease in a mammal, such as a human.

It is understood that any aspect or feature of the present invention whether characterized as preferred or not characterized as preferred may be combined with any other aspect or feature of the invention, whether such other feature is characterized as preferred or not characterized as preferred. For example, an aspect or feature described as preferred, for example a particular R group, or a specific $R^1$ group for a particular compound of the formula I (for example, where $R^1$ is hydrogen, $(C_1-C_5)$alkyl, halo$(C_1-C_8)$alkyl, $(C_3-C_5)$alkenyl, or $(C_3-C_5)$alkynyl) may be combined with any other groups such as $R^2$, X, Z, $Z^1$ etc . . . to form a compound of the invention having a different combination of substituents without deviating from the present invention.

Additional compounds useful to practice the invention are depicted in the table below:

TABLE 1

Activity of $A_{2B}$ Antagonists

| Cmpd | $R^1$ | $R^2$ | R | —X$(Z^1)_n$—Z | RatA$_{2B}$ $K_i$ (nM) |
|---|---|---|---|---|---|
| 1 | Pr | Pr | H | 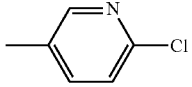 | +++ |
| 2 | Propargyl | Me | H | 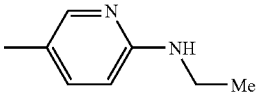 | ++ |
| 3 | Pr | Pr | H | 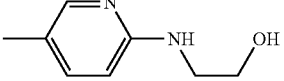 | +++ |
| 4 | Pr | Pr | H | 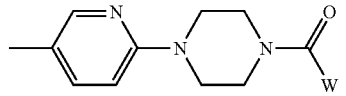 | +++ |
| 5 | Pr | Pr | H | 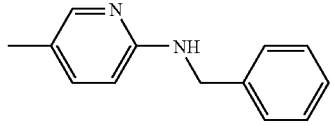 | +++ |
| 6 | Pr | Pr | H | 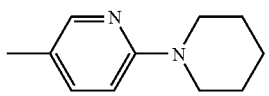 | |
| 7 | Pr | Pr | H | | |
| 8 | Pr | Pr | H | 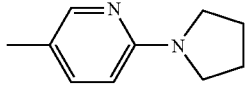 | +++ |

TABLE 1-continued
Activity of A$_{2B}$ Antagonists
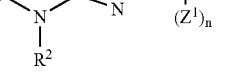
| Cmpd | R$^1$ | R$^2$ | R | —X(Z$^1$)$_n$—Z | RatA$_{2B}$ K$_i$ (nM) |
|---|---|---|---|---|---|
| 9 | Pr | Pr | H | 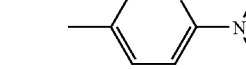 | ++++ |
| 10 | Pr | Pr | H |  | +++ |
| 11 | Pr | Pr | H |  | |
| 12 | Pr | Pr | H |  | |
| 13 | Pr | Pr | H | 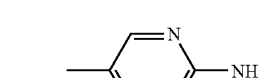 | +++ |
| 14 | Pr | Pr | H | 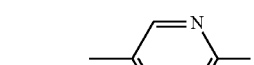 | +++ |
| 15 | Pr | Pr | H | 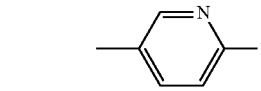 | ++++ |
| 16 | Pr | Pr | H |  | ++++ |
| 17 | Pr | Pr | H |  | |
| 18 | Pr | Pr | H | | +++ |

TABLE 1-continued

Activity of A$_{2B}$ Antagonists

Structure: xanthine core with R$^1$ on N1, R$^2$ on N3, R on N7, and —X(Z$^1$)$_n$—Z substituent on C8.

| Cmpd | R$^1$ | R$^2$ | R | —X(Z$^1$)$_n$—Z | RatA$_{2B}$ K$_i$ (nM) |
|---|---|---|---|---|---|
| 19 | Pr | Pr | H | 5-methylpyridin-2-yl-piperazine | +++ |
| 20 | Pr | Pr | H | 5-methylpyridin-2-yl-NH-CH$_2$-CH(OH)-phenyl |  |
| 21 | Pr | Pr | H | 5-methylpyridin-2-yl-NH-CH$_2$-(1,4-phenylene)-CH$_2$NH$_2$ |  |
| 22 | Pr | Pr | H | 5-methylpyridin-2-yl-NH-phenyl |  |
| 23 | Pr | Pr | H | 5-methylpyridin-2-yl-NH-cyclopropyl | +++ |
| 24 | Pr | Pr | H | 5-methylpyridin-2-yl-NH-CH$_2$-(pyridin-2-yl) |  |
| 25 | Pr | Pr | H | 5-methylpyridin-2-yl-(4-methylpiperazin-1-yl) |  |
| 26 | Pr | Pr | H | 5-methylpyridin-2-yl-NH-CH$_2$-(pyridin-3-yl) |  |
| 27 | Pr | Pr | H | 5-methylpyridin-2-yl-NH-CH$_2$-(2-methylphenyl) |  |

TABLE 1-continued

Activity of A$_{2B}$ Antagonists

| Cmpd | R$^1$ | R$^2$ | R | —X(Z$^1$)$_n$—Z | RatA$_{2B}$ K$_i$ (nM) |
|---|---|---|---|---|---|
| 28 | Pr | Pr | H | 5-methylpyridin-2-yl-NH-CH$_2$CH$_2$-(3,4-dimethoxyphenyl) | |
| 29 | Pr | Pr | H | 5-methylpyridin-2-yl-N(Me)-C(O)-NH-propyl | |
| 30 | Pr | Pr | H | 5-methylpyridin-2-yl-NH-CH(Et)$_2$ | |
| 31 | Pr | Pr | H | 5-methylpyridin-2-yl-NH-CH$_2$-CH(phenyl)$_2$ | |
| 32 | Pr | Pr | H | 5-methylpyridin-2-yl-NH-CH$_2$-(1-ethylpyrrolidin-2-yl) | |
| 33 | Pr | Pr | H | 5-methylpyridin-2-yl-NH-CH$_2$-(3-methoxyphenyl) | |
| 34 | Pr | Pr | H | 5-methylpyridin-2-yl-N(Me)-C(O)-NH-phenyl | |

TABLE 1-continued

Activity of A$_{2B}$ Antagonists

| Cmpd | R$^1$ | R$^2$ | R | —X(Z$^1$)$_n$—Z | RatA$_{2B}$ K$_i$ (nM) |
|---|---|---|---|---|---|
| 35 | Pr | Pr | H | 5-methyl-pyridin-2-yl-NH-CH$_2$-furan-2-yl | |
| 36 | Pr | Pr | H | 5-methyl-pyridin-2-yl-NH-CH$_2$CH$_2$-(4-methoxyphenyl) | |
| 37 | Pr | Pr | H | 5-methyl-pyridin-2-yl-NH-CH$_2$-(2-methoxyphenyl) | |
| 38 | Pr | Pr | H | 5-methyl-pyridin-2-yl-NH-propyl | |
| 39 | Pr | Pr | H | 5-methyl-pyridin-2-yl-NH-cyclopentyl | ++ |
| 40 | Pr | Pr | H | 5-methyl-pyridin-2-yl-NH-cyclohexyl | |
| 41 | Pr | Pr | CH$_3$CH$_2$— | 5-methyl-2-chloro-pyridine | |
| 42 | Pr | Pr | 4-fluorobutyl | 5-methyl-2-chloro-pyridine | |

TABLE 1-continued
Activity of A$_{2B}$ Antagonists
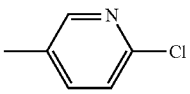
| Cmpd | R$^1$ | R$^2$ | R | —X(Z$^1$)$_n$—Z | RatA$_{2B}$ K$_i$ (nM) |
|------|-------|-------|---|------------------|------------------------|
| 43 | Pr | Pr | CH$_3$— | 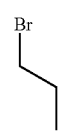 | |
| 44 | Pr | Pr | Br(propyl) | 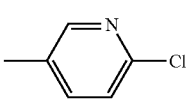 | |
| 45 | Pr | Pr | H | 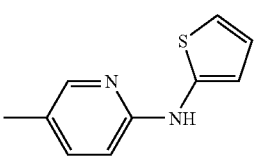 | |
| 46 | Pr | Pr | H | 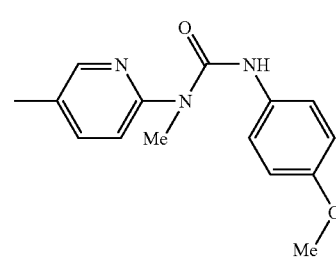 | |
| 47 | Pr | Pr | H | 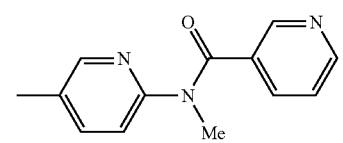 | +++ |
| 48 | Pr | Pr | H | 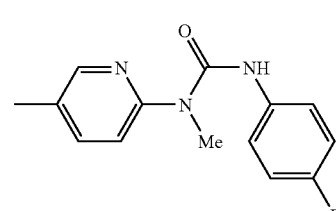 | |
| 49 | Pr | Pr | H | 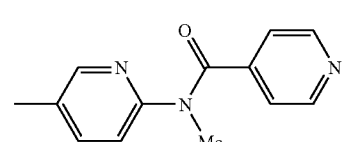 | ++++ |
| 50 | Pr | Pr | H | 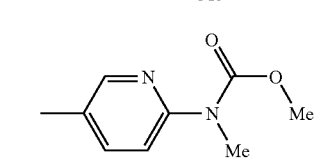 | |

TABLE 1-continued

Activity of A$_{2B}$ Antagonists

| Cmpd | R$^1$ | R$^2$ | R | —X(Z$^1$)$_n$—Z | RatA$_{2B}$ K$_i$ (nM) |
|---|---|---|---|---|---|
| 51 | Pr | Pr | H | | |
| 52 | Pr | Pr | H | | |
| 53 | Pr | Pr | H | | |
| 54 | Pr | 4-MeO-C$_6$H$_4$-CH$_2$CH$_2$- | H | | ++ |
| 55 | Pr | 4-MeO-C$_6$H$_4$-CH$_2$CH$_2$- | H | | |
| 56 | Pr | Pr | H | | |

TABLE 1-continued

Activity of A$_{2B}$ Antagonists

| Cmpd | R$^1$ | R$^2$ | R | —X(Z$^1$)$_n$—Z | RatA$_{2B}$ K$_i$ (nM) |
|---|---|---|---|---|---|
| 57 | Pr | Pr | H | 5-methylpyridin-2-yl-piperazine-N-carbonyl-pyridin-3-yl | |
| 58 | Pr | Pr | H | 5-methylpyridin-2-yl-(1,4-diazepan-1-yl) | ++++ |
| 59 | Et | Et | H | 5-methyl-2-chloropyridine | |
| 60 | Et | Et | H | 5-methylpyridin-2-yl-piperazine | |
| 61 | Et | Et | H | 5-methylpyridin-2-yl-N(Me)-C(O)-NH-phenyl | ++ |
| 62 | Et | Et | H | 5-methylpyridin-2-yl-N(Et)-C(O)-pyridin-3-yl | +++ |
| 63 | Et | Et | H | 5-methylpyridin-2-yl-NH-Me | |
| 64 | Et | Et | H | 5-methylpyridin-2-yl-N(Me)-C(O)-pyridin-3-yl | +++ |
| 65 | Et | Et | H | 5-methylpyridin-2-yl-N(cyclopropyl)-C(O)-pyridin-3-yl | |

TABLE 1-continued
Activity of A$_{2B}$ Antagonists
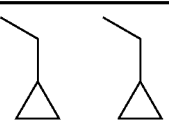
| Cmpd | R$^1$ | R$^2$ | R | —X(Z$^1$)$_n$—Z | RatA$_{2B}$ K$_i$ (nM) |
|---|---|---|---|---|---|
| 66 | 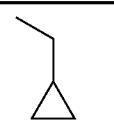 | 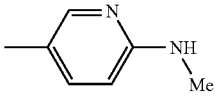 | H | 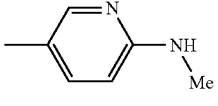 | |
| 67 | Propargyl | Me | H | 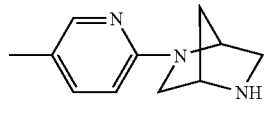 | |
| 68 | Pr | Pr | H | 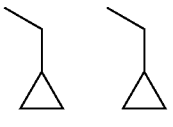 | +++ |
| 69 | 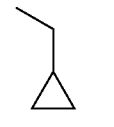 | 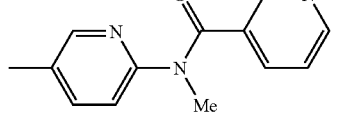 | H | 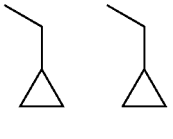 | +++ |
| 70 | 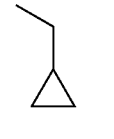 | 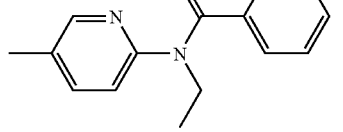 | H | 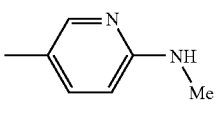 | +++ |
| 71 | Allyl | Allyl | H | 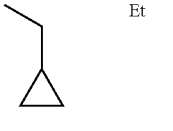 | |
| 72 | 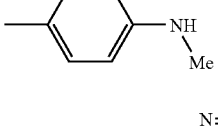 | Et | H | 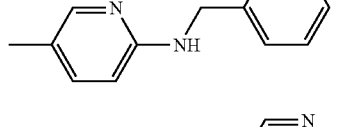 | |
| 73 | Et | Et | H | 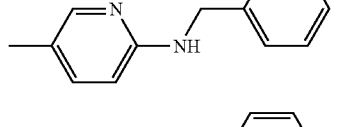 | ++++ |
| 74 | Et | Et | H | 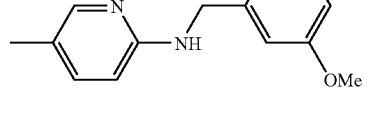 | ++++ |
| 75 | Et | Et | H | | ++++ |

TABLE 1-continued
Activity of A$_{2B}$ Antagonists
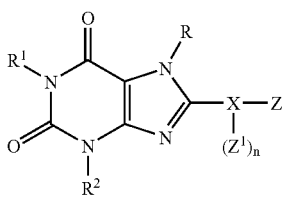
| Cmpd | R$^1$ | R$^2$ | R | —X(Z$^1$)$_n$—Z | RatA$_{2B}$ K$_i$ (nM) |
|---|---|---|---|---|---|
| 76 | Pr | Pr | H | 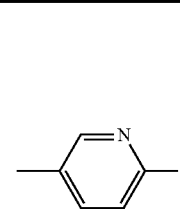 | |
| 77 | Et | Et | H | 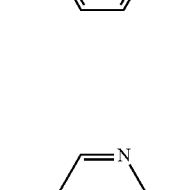 | |
| 78 | Pr | Pr | H | 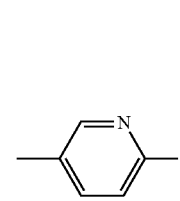 | ++++ |
| 79 | Et | Et | H | 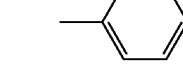 | |
| 80 | Et | Et | H | 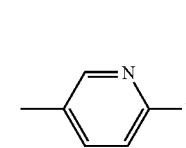 | |
| 81 | Et | Et | H | 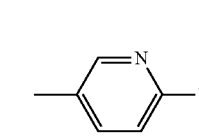 | ++++ |
| 82 | Pr | Pr | H |  | |

TABLE 1-continued
Activity of A$_{2B}$ Antagonists
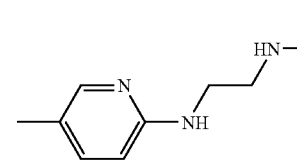
| Cmpd | R$^1$ | R$^2$ | R | —X(Z$^1$)$_n$—Z | RatA$_{2B}$ K$_i$ (nM) |
|---|---|---|---|---|---|
| 83 | Pr | Pr | H | 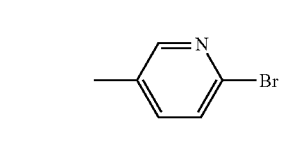 | +++ |
| 84 | Et | Et | H | 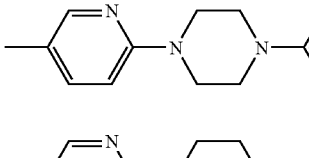 | |
| 85 | Pr | Pr | H | 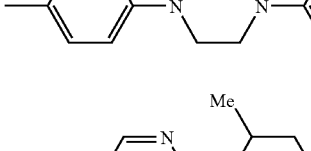 | |
| 86 | Et | Et | H | 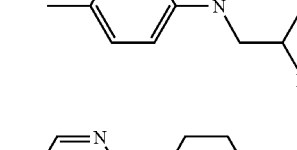 | |
| 87 | Et | Et | H | 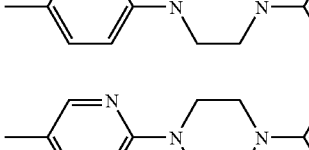 | |
| 88 | Pr | Pr | H | 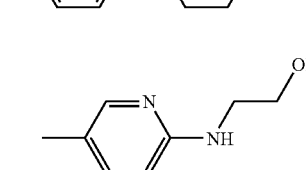 | |
| 89 | Et | Et | H | 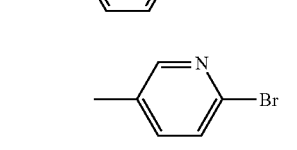 | |
| 90 | Et | Et | H |  | |
| 91 | Propargyl | Me | H | | |

TABLE 1-continued
Activity of A$_{2B}$ Antagonists
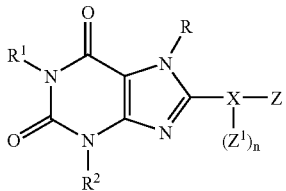
| Cmpd | R$^1$ | R$^2$ | R | —X(Z$^1$)$_n$—Z | RatA$_{2B}$ K$_i$ (nM) |
|---|---|---|---|---|---|
| 92 | Et | Et | H | 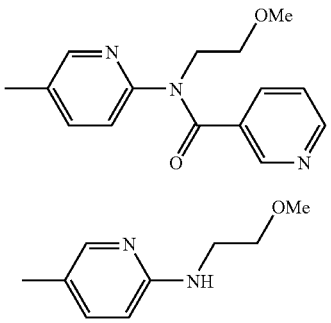 | |
| 93 | Propargyl | Me | H | 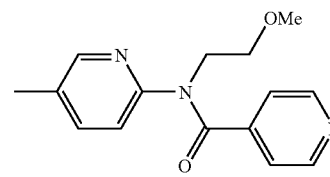 | |
| 94 | Et | Et | H | 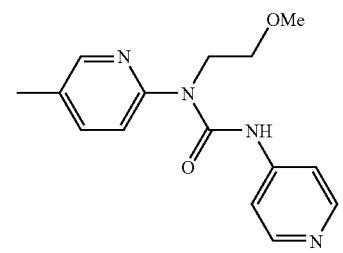 | |
| 95 | Et | Et | H | 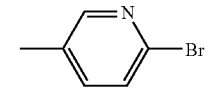 | +++ |
| 96 | Me | Me | H | 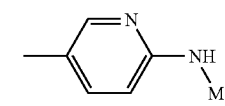 | |
| 97 | Me | Me | H | 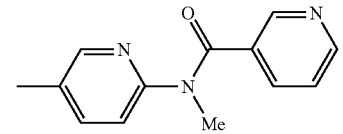 | +++ |
| 98 | Me | Me | H | 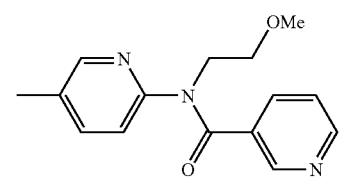 | |
| 99 | Pr | Pr | H | | |

TABLE 1-continued

Activity of A$_{2B}$ Antagonists

| Cmpd | R$^1$ | R$^2$ | R | —X(Z$^1$)$_n$—Z | RatA$_{2B}$ K$_i$ (nM) |
|---|---|---|---|---|---|
| 100 | Propargyl | Me | H | (5-methylpyridin-2-yl)-N-(2-methoxyethyl)nicotinamide | ++ |
| 101 | Propargyl | Me | H | (5-methylpyridin-2-yl)-N-methylnicotinamide | +++ |
| 102 | Pr | Pr | H | 2,6-dichloro-3-methylpyridine | |
| 103 | Pr | Pr | H | 2,6-bis(methylamino)-3-methylpyridine | |
| 104 | Pr | Pr | H | 2,6-bis((2-methoxyethyl)amino)-3-methylpyridine | |
| 105 | Pr | Pr | H | 3-methyl-2,6-bis(N-methylnicotinamido)pyridine | |

TABLE 1-continued

Activity of A$_{2B}$ Antagonists

| Cmpd | R$^1$ | R$^2$ | R | —X(Z$^1$)$_n$—Z | RatA$_{2B}$ K$_i$ (nM) |
|---|---|---|---|---|---|
| 106 | Pr | Pr | H | (structure) | |
| 107 | Et | Et | H | (structure) | |
| 108 | Et | Et | H | (structure) | +++ |
| 109 | Pr | Pr | H | (structure) | +++ |
| 110 | Pr | Pr | H | (structure) | +++ |
| 111 | Pr | Pr | H | (structure) | ++++ |
| 112 | Pr | Pr | H | (structure) | |

TABLE 1-continued

Activity of A$_{2B}$ Antagonists

| Cmpd | R$^1$ | R$^2$ | R | —X(Z$^1$)$_n$—Z | RatA$_{2B}$ K$_i$ (nM) |
|---|---|---|---|---|---|
| 113 | Pr | Pr | H | 5-methyl-pyridin-2-yl-N(Me)-C(O)-pyridin-4-yl N-oxide | |
| 114 | Pr | 4-methoxyphenethyl | H | 5-methyl-pyridin-2-yl-NH-Me | |
| 115 | Et | Et | H | 5-methyl-pyridin-2-yl-N(Me)-C(O)-pyridin-4-yl N-oxide | |
| 116 | Allyl | Allyl | H | 5-methyl-2-chloropyridine | |
| 117 | Pr | 4-methoxyphenethyl | H | 5-methyl-pyridin-2-yl-N(Me)-C(O)-pyridin-3-yl | |
| 118 | Pr | 4-methoxyphenethyl | H | 5-methyl-pyridin-2-yl-N(Me)-C(O)-6-chloropyridin-3-yl | |

TABLE 1-continued

Activity of A$_{2B}$ Antagonists

| Cmpd | R$^1$ | R$^2$ | R | —X(Z$^1$)$_n$—Z | RatA$_{2B}$ K$_i$ (nM) |
|---|---|---|---|---|---|
| 119 | Allyl | Allyl | H | | |
| 120 | Allyl | Allyl | H | | ++++ |
| 121 | Pr | Pr | H | | ++++ |
| 122 | cyclopropyl | Pr | H | | |
| 123 | Et | Et | H | | |
| 124 | Et | Et | H | | |
| 125 | cyclopropyl | Et | H | | |
| 126 | cyclopropyl | Pr | H | | |
| 127 | Pr | cyclopropyl | H | | |

TABLE 1-continued
Activity of A$_{2B}$ Antagonists
| Cmpd | R$^1$ | R$^2$ | R | —X(Z$^1$)$_n$—Z | RatA$_{2B}$ K$_i$ (nM) |
|------|-------|-------|---|-----------------|------------------------|
| 128 | cyclopropyl | Pr | H | 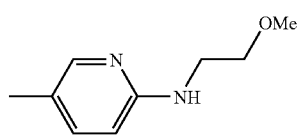 | |
| 129 | cyclopropyl | Pr | H |  | ++++ |
| 130 | Et | Et | H | 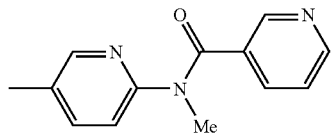 | ++++ |
| 131 | Pr | Pr | H | 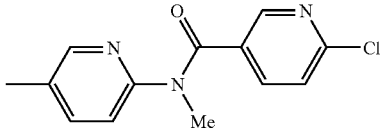 | |
| 132 | Pr | Pr | H | 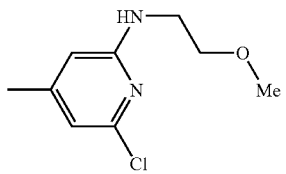 | |
| 133 | Pr | Pr | H | 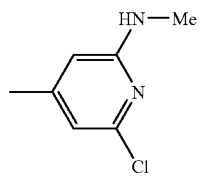 | |

TABLE 1-continued

Activity of A$_{2B}$ Antagonists

| Cmpd | R$^1$ | R$^2$ | R | —X(Z$^1$)$_n$—Z | RatA$_{2B}$ K$_i$ (nM) |
|---|---|---|---|---|---|
| 134 | Pr | Pr | H | N-methyl-N-(4-methyl-6-chloropyridin-2-yl)nicotinamide | |
| 135 | cyclopropyl | Pr | H | N-methyl-N-(5-methylpyridin-2-yl)-6-chloronicotinamide | |
| 136 | Et | cyclopropyl | H | 5-methyl-2-(methylamino)pyridine | |
| 137 | Et | cyclopropyl | H | 5-methyl-2-((2-methoxyethyl)amino)pyridine | |
| 138 | Et | Et | H | 5-methyl-2-hydrazinylpyridine | |
| 139 | Et | Et | H | 5-methyl-2-(cyclopropylamino)pyridine | |
| 140 | Et | Et | H | 5-methyl-2-((cyclopropylmethyl)amino)pyridine | |

TABLE 1-continued

Activity of $A_{2B}$ Antagonists

| Cmpd | $R^1$ | $R^2$ | R | —X(Z$^1$)$_n$—Z | RatA$_{2B}$ K$_i$ (nM) |
|---|---|---|---|---|---|
| 141 | Et | Et | H | 5-methylpyridin-2-yl-NH-NH-C(O)-(pyridin-3-yl) | |
| 142 | Et | Et | H | 5-methylpyridin-2-yl-N(C(O)-pyridin-3-yl)-NH-C(O)-(pyridin-3-yl) | |
| 143 | Et | Et | H | 5-methylpyridin-2-yl-NH-Et | |
| 144 | Et | Et | H | 5-methylpyridin-2-yl-N(CH$_2$-cyclopropyl)-C(O)-(pyridin-3-yl) | +++ |
| 145 | CH$_2$-cyclopropyl | Et | H | 5-methylpyridin-2-yl-N(Me)-C(O)-(6-chloropyridin-3-yl) | ++++ |

Note:
+: Ki < 10000 nM, ++: Ki < 5000 nM, +++: Ki < 500 nM, ++++: Ki < 100 nM.

Synthesis of the Compounds of Formula I

The compounds of Formula IA can be prepared by the methods described in P. J. Scammells, et al., *J. Med. Chem.* 37, 2704-2712 (1994). A diamino-1,3-disubstituted uracil is acylated with 6-chloronicotinoyl chloride in pyridine at 5° C. to provide the compounds of Formula (5a). The resulting amide (5a) is cyclized by refluxing in an aqueous sodium hydroxide solution to provide the compound IA. 6-Chloronicotinoyl chloride is prepared by refluxing 6-hydroxynicotinic acid in thionyl chloride using DMF as the catalyst as shown in Reaction Scheme 1.

Compound IA can be alkylated with alkyl bromide or iodide to provide compounds of Formula IB. Compounds IA or IB reacts with substituted amine at 150-160° C. in a pressure tube to give compounds of Formula IC. Compounds of Formula IC where $R^4$ is hydroden can react with isocyanate or acyl chloride to afford compounds of Formula I where $R^4$ is —C(O)NHR$^7$ (ID) or —C(O)R$^6$ (IE), respectively.

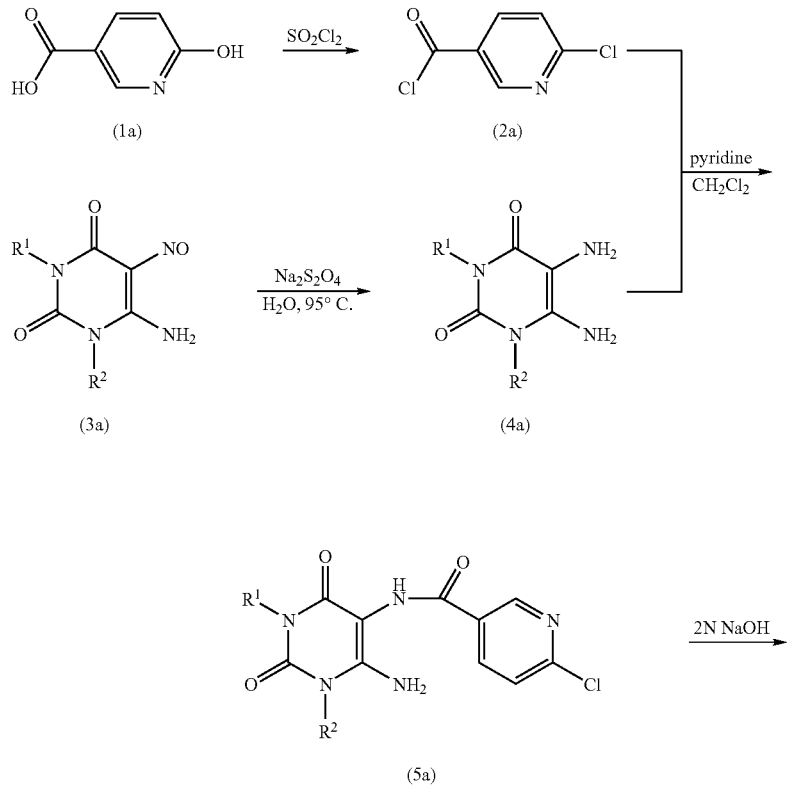
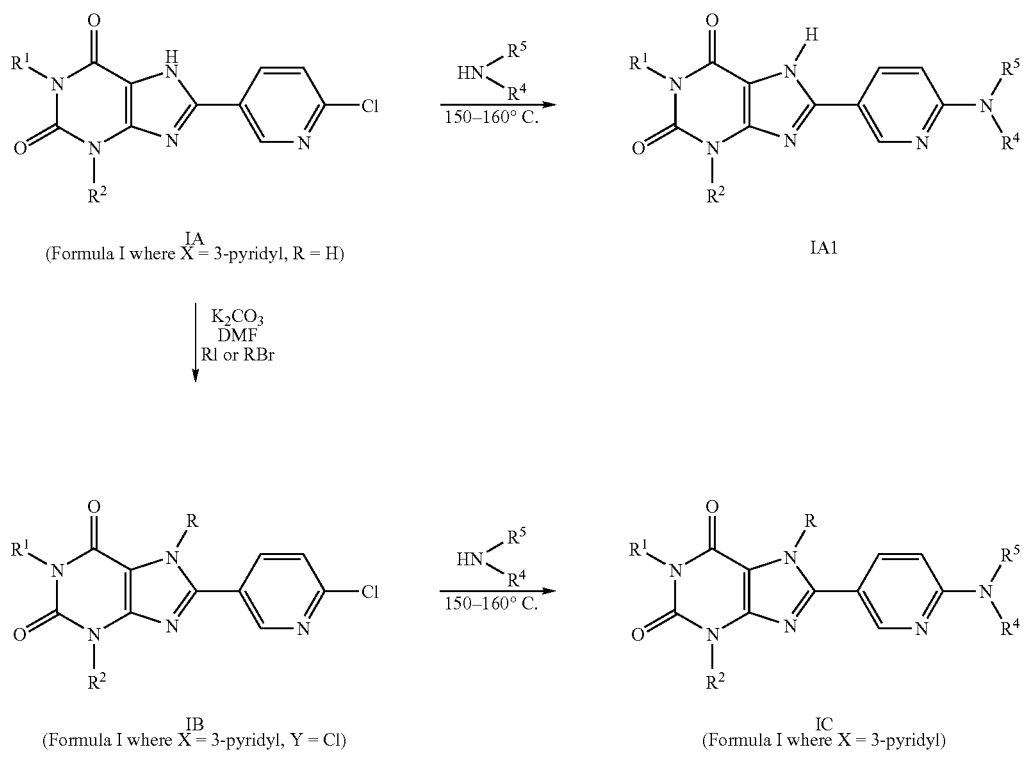

-continued
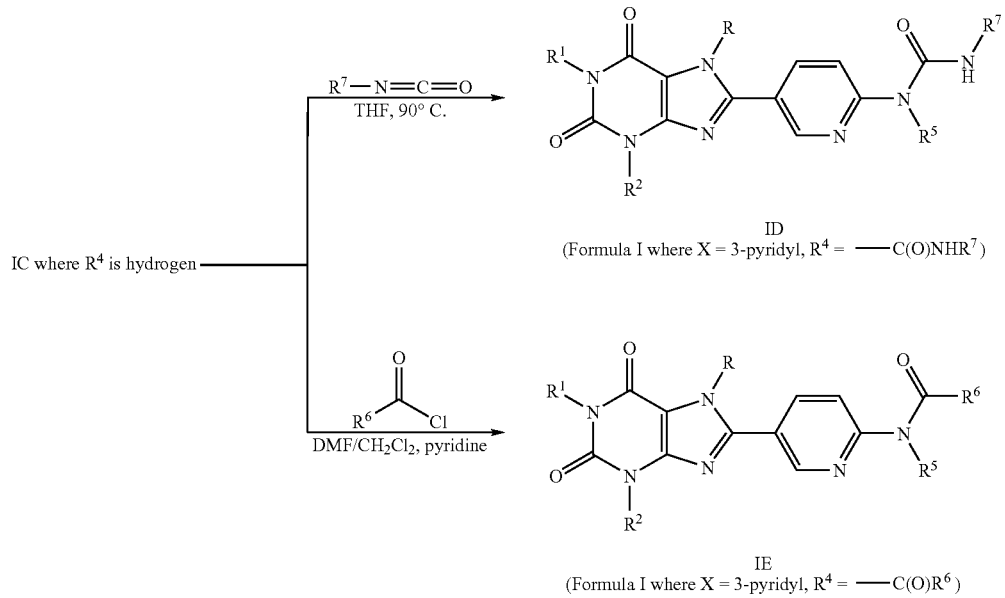
Compounds of the invention where Z is —NR⁴R⁵ and R⁴ and R⁵ together with the atoms to which they are attached form a ring containing a NH group, e.g., IC, or IA1, can be prepared by reacting the compound with an isocyanate or acyl chloride to provide compounds having Formula IF and IG, as shown in SCHEME 2, below:
REACTION SCHEME 2
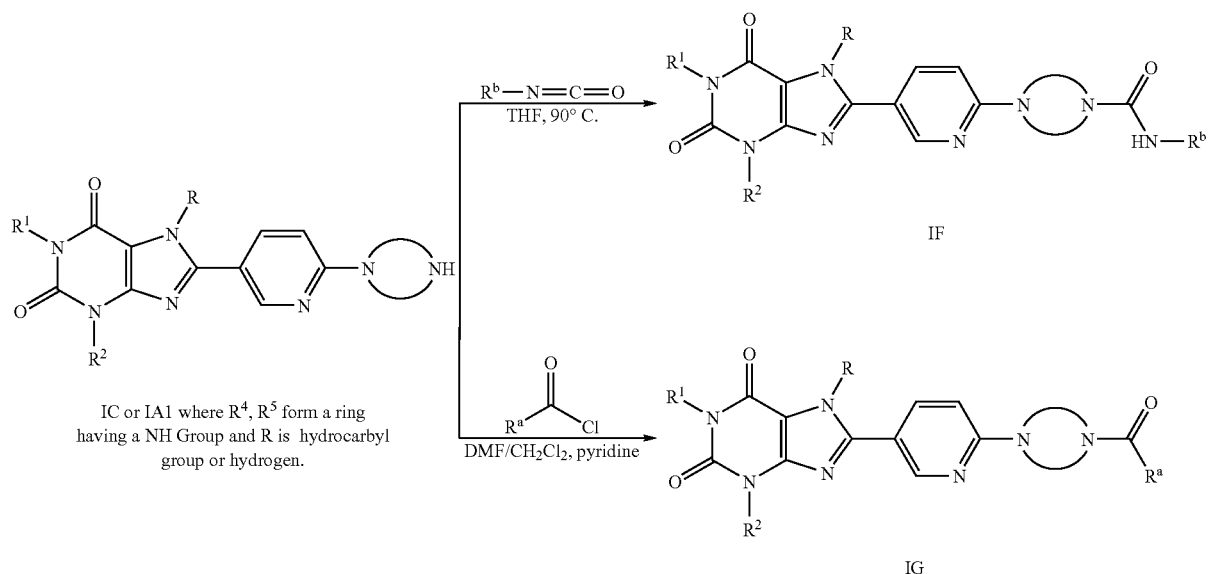

SCHEME 3 shows that Compound IA can react with hydrazine or substituted hydrazine at 100-160° C. to give compounds of Formula IA2. Compounds of Formula IA2 where $R^8$ is hydrogen can react with acyl chloride to afford compounds of Formula IH and IJ. Compound IA can also react with ketone or aldehyde to give compound of Formula IL.

DMEM Dulbecco modified eagle medium
DMF N,N-dimethylformamide
DMSO dimethylsulfoxide
EDTA ethylenediaminetetraacetate
HEK cells human embryonic kidney cells
$K_i$ equilibrium inhibition constant
NECA 5'-(N-ethylcarbamoyl)adenosine

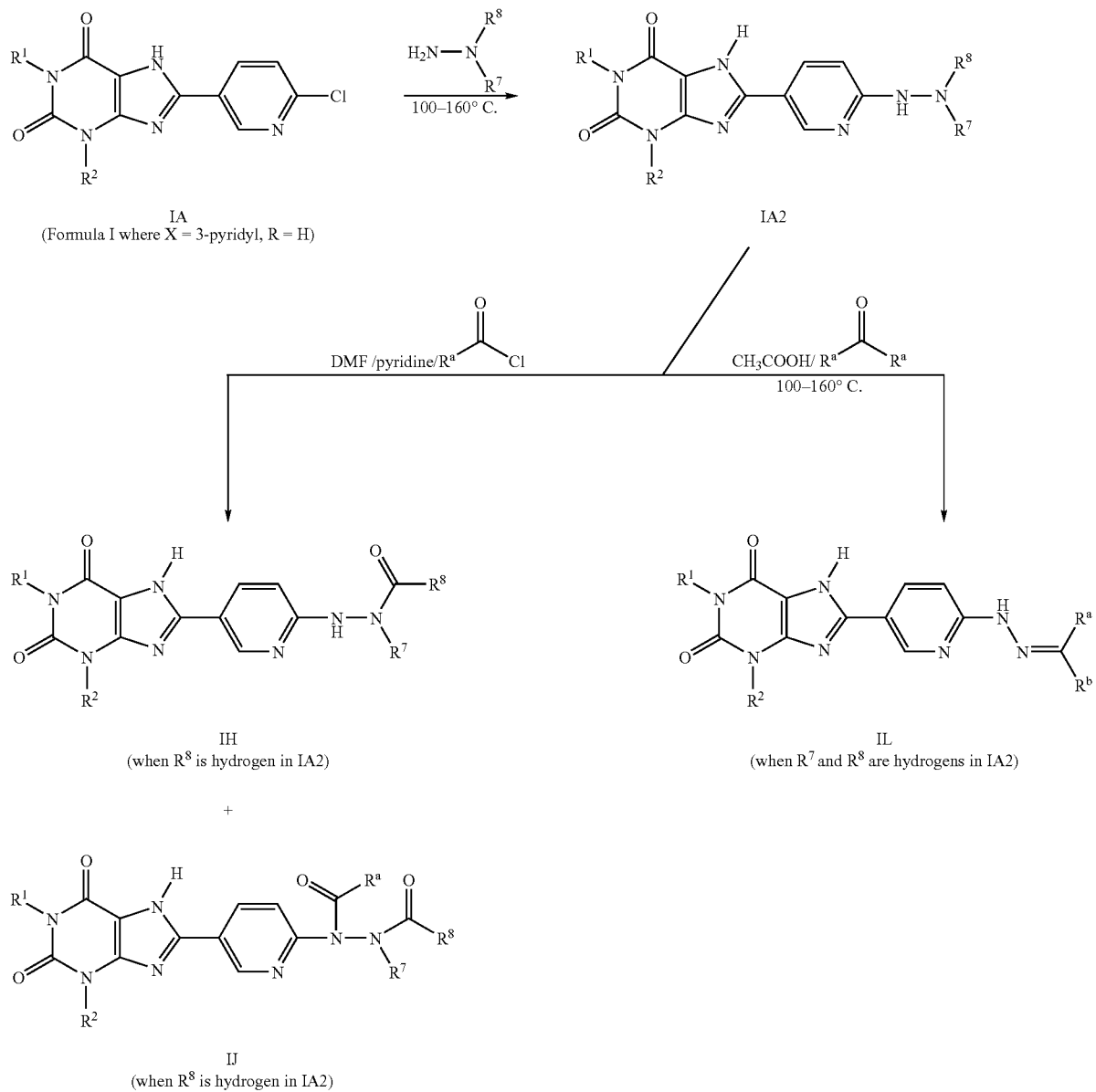

The following abbreviations have been used herein:
[$^{125}$I]ABA [$^{125}$I]N$^6$-(4-aminobenzyl)-adenosine
$^{125}$I-ABOPX $^{125}$I-3-(4-amino-3-iodobenzyl)-8-oxyacetate-1-propyl-xanthine
AR adenosine receptor
CGS 21680 2-[4-[(2-carboxyethyl)phenyl]ethyl-amino]-5N-N-ethylcarbamoyl adenosine
CPX 8-cyclopentyl-1,3-dipropylxanthine
R-PIA R-N$^6$-phenylisopropyladenosine
TEA triethylamine
TLC Thin layer chromatography
ZM 241385 4-(2-[7-amino-2-{furyl}{1,2,4}triazolo{2,3-a}{1,3,5}triazin-5-ylaminoethyl)pheno In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic or stereoisomeric form or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis or by chromatographic separation using a chiral stationary phase). It is also conventional to determine $A_{2B}$ adenosine antagonist activity using the standard tests described herein or using other similar tests which are well known in the art.

The compounds of formula I can be formulated as pharmaceutical compositions and administered to a mammalian host, such as a human patient in a variety of forms adapted to the chosen route of administration, i.e., orally or parenterally, by intravenous, intramuscular, topical, inhalation or subcutaneous routes. Exemplary pharmaceutical compositions are disclosed in "Remington: The Science and Practice of Pharmacy", A. Gennaro, ed., 20th edition, Lippincott, Williams & Wilkins, Philadelphia, Pa.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1.0 to about 100 mg/kg, preferably from about 10 to about 75 mg/kg of body weight per day, more preferably 5 to about 20 mg per kilogram body weight of the recipient per day.

The compound can be conveniently administered in unit dosage form; for example, tablets, caplets, etc., containing 4 to 400 mg, preferably 10 to 200 mg, most preferably, 20 to 100 mg of active ingredient per unit dosage form.

Ideally, the active ingredient should be administered to achieve peak plasma concentrations of the active compound of from about 0.02 to about 20 µM, preferably, about 0.1 to 10 µM, most preferably, about 0.5 to about 5 µM. These concentrations may be achieved, for example, by the intravenous injection of a 0.005 to 0.5% solution of the active ingredient, or orally administered as a bolus containing about 4 to 400 mg of the active ingredient.

The compounds of the invention can be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All patents, patent applications, books and literature cited in the specification are hereby incorporated by reference in their entirety. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

The invention will now be illustrated by the following non-limiting Examples.

EXAMPLES

Pharmacology.

The ability of compounds of the invention to act as an $A_{2B}$ adenosine receptor antagonists may be determined using pharmacological models which are well known to the art or using test procedures described below.

The rat $A_{2B}$ receptor cDNA was subcloned into the expression plasmid pDouble Trouble using techniques described in Robeva, A. et al., *Biochem. Pharmacol.*, 51, 545-555 (1996). The plasmid was amplified in competent JM109 cells and plasmid DNA isolated using Wizard Megaprep columns (Promega Corporation, Madison, Wis.). $A_{2B}$ adenosine receptors were introduced into HEK-293 cells by means of Lipofectin as described in Felgner, P. L. et al., *Proc. Natl. Acad. Sci. USA*, 84, 7413-7417 (1987).

Cell Culture

Transfected HEK cells were grown under 5% $CO_2$/95% $O_2$ humidified atmosphere at a temperature of 37° C. Colonies were selected by growth of cells in 0.6 mg/mL G418. Transfected cells were maintained in DMEM supplemented with Hams F12 nutrient mixture (1/1), 10% newborn calf serum, 2 mM glutamine and containing 50 IU/mL penicillin, 50 mg/mL streptomycin, and 0.2 mg/mL Geneticin (G418, Boehringer Mannheim). Cells were cultured in 10 cm diameter round plates and subcultured when grown confluent (approximately after 72 hours).

Radioligand Binding Studies.

At $A_{2B}$ receptors: Confluent monolayers of HEK-$A_{2B}$ cells were washed with PBS followed by ice cold Buffer A (10 mM HEPES, 10 mM EDTA, pH 7.4) with protease inhibitors (10 µg/mL benzamidine, 100 µM phenylmethanesulfonyl fluoride, and 2 µg/mL of each aprotinin, pepstatin and leupeptin). The cells were homogenized in a Polytron (Brinkmann) for 20 s, centrifuged at 30,000×g, and the pellets washed twice with buffer HE (10 mM HEPES, 1 mM EDTA, pH 7.4 with protease inhibitors). The final pellet was resuspended in buffer HE, supplemented with 10% sucrose and frozen in aliquots at −80° C. For binding assays membranes were thawed and diluted 5-10 fold with HE to a final protein concentration of approximately 1 mg/mL. To determine protein concentrations, membranes, and bovine serum albumin standards were dissolved in 0.2% NaOH/0.01% SDS and protein determined using fluorescamine fluorescence. Stowell, C. P. et al., *Anal. Biochem.*, 85, 572-580 (1978).

Saturation binding assays for rat $A_{2B}$ adenosine receptors were performed with [$^3$H]ZM214,385 (17 Ci/mmol, Tocris Cookson, Bristol UK) (Ji, X. et al., *Drug Design Discov.*, 16, 216-226 (1999)) or $^{125}$I]-ABOPX (2200 Ci/mmol). To prepare $^{125}$I-ABOPX, 10 µL of 1 mM ABOPX in methanol/1 M NaOH (20:1) was added to 50 μL of 100 mM phosphate buffer, pH 7.3. One or 2 mCi of Na$^{125}$I was added, followed by 10 μL of 1 mg/mL chloramine-T in water. After incubation, 20 minutes at room temperature, 50 μL of 10 mg/mL Na-metabisulfite in water was added to quench the reaction. The reaction mixture was applied to a C18 HPLC column, eluting with a mixture of methanol and 5 mM phosphate, pH 6.0. After 5 min at 35% methanol, the methanol concentration was ramped to 100% over 15 min. Unreacted ABOPX eluted in 11-12 minutes; $^{125}$I-ABOPX eluted at 18-19 min in a yield of 50-60% with respect to the initial $^{125}$I.

In equilibrium binding assays the ratio of $^{127}$I/$^{125}$I-ABOPX was 10-20/1. Radioligand binding experiments Were performed in triplicate with 20-25 μg membrane protein in a total volume of 0.1 mL HE buffer supplemented with 1 U/mL adenosine deaminase and 5 mM MgCl$_2$. The incubation time was 3 h at 21° C. Nonspecific binding was measured in the presence of 100 μM NECA. Competition experiments were carried out using 0.6 nM $^{125}$I-ABOPX. Membranes were filtered on Whatman GF/C filters using a Brandel cell harvester (Gaithersburg, Md.) and washed 3 times over 15-20 seconds with ice cold buffer (10 mM Tris, 1 mM MgCl$_2$, pH 7.4). B$_{max}$ and K$_D$ values were calculated by Marquardt's nonlinear least squares interpolation for single a site binding models. Marquardt, D. M., *J. Soc. Indust. Appl. Math.*, 11, 431-441.21 (1963). K$_i$ values for different compounds were derived from IC$_{50}$ values as described. Linden, J., *J. Cycl. Nucl. Res.*, 8 163-172 (1982). Data from replicate experiments are tabulated as means±SEM.

At other Adenosine Receptors: [$^3$H]CPX. Bruns, R. F. et al., *Naunyn-Schmiedeberp's Arch. Pharmacol.*, 335, 59-63 (1987). $^{125}$I-ZM241385 and $^{125}$I-ABA were utilized in radioligand binding assays to membranes derived from HEK-293 cells expressing recombinant rat A$_1$, A$_{2A}$ and A$_3$ ARs, respectively. Binding of [$^3$H]R-N$^6$-phenylisopropyladenosine. Schwabe, U. et al., *Naunyn-Schmiedeberg's Arch. Pharmacol.*, 313, 179-187 (1980). ([$^3$H]R-PIA, Amersham, Chicago, Ill.) to A$_1$ receptors from rat cerebral cortical membranes and of [$^3$H]CGS 21680. Jarvis, M. F. et al., *J. Pharmacol. Exp. Therap.*, 251, 888-893 (1989). (Dupont NEN, Boston, Mass.) to A$_{2A}$ receptors from rat striatal membranes was performed as described. Adenosine deaminase (3 units/mL) was present during the preparation of the brain membranes, in a pre-incubation of 30 min, at 30° C., and during the incubation with the radioligands. All non-radioactive compounds were initially dissolved in DMSO, and diluted with buffer to the final concentration, where the amount of DMSO never exceeded 2%. Incubations were terminated by rapid filtration over Whatman GF/B filters, using a Brandell cell harvester (Brandell, Gaithersburg, Md.). The tubes were rinsed three times with 3 mL buffer each.

At least six different concentrations of competitor, spanning 3 orders of magnitude adjusted appropriately for the IC$_{50}$ of each compound, were used. IC$_{50}$ values, calculated with the nonlinear regression method implemented in (Graph-Pad Prism, San Diego, Calif.), were converted to apparent K$_i$ values as described. Linden, J., *J. Cyci. Nucl. Res.*, 8:163-172 (1982). Hill coefficients of the tested compounds were in the range of 0.8 to 1.1.

Functional Assay:

HEK-A$_{2B}$ cells from one confluent T75 flask were rinsed with Ca$^{2+}$ and Mg$^{2+}$-free Dulbecco's phosphate buffered saline (PBS) and then incubated in Ca$^{2+}$ and Mg$^{2+}$-free HBSS with 0.05% trypsin and 0.53 mM EDTA until the cells detached. The cells were rinsed twice by centrifugation at 250×g in PBS and resuspended in 10 mL of HBSS composed of 137 mM NaCl, 5 mM KCl, 0.9 mM MgSO$_4$, 1.4 mM CaCl$_2$, 3 mM NaHCO$_3$, 0.6 mM Na$_2$HPO$_4$, 0.4 mM KH$_3$PO$_4$, 5.6 mM glucose, and 10 mM HEPES, pH 7.4 and the Ca$^{2+}$-sensitive fluorescent dye indo-1-AM (5 μM) 37° C. for 60 min. The cells were rinsed once and resuspended in 25 mL dye-free HBSS supplemented with 1 U/ml adenosine deaminase and held at room temperature. Adenosine receptor antagonists prepared as 100× stocks in DMSO or vehicle was added and the cells and transferred to a 37° C. bath for 2 minutes. Then the cells (1 million in 2 ml) were transferred to a stirred cuvette maintained at 37° C. within an Aminco SLM 8000 spectrofluorometer (SML instruments, Urbana Ill.). The ratios of indo-1 fluorescence obtained at 400 and 485 nm (excitation, 332 nm) was recorded using a slit width of 4 nm. NECA was added after a 100 s equilibration period.

Cyclic AMP Accumulation

Cyclic AMP generation was performed in DMEM/HEPES buffer (DMEM containing 50 mM HEPES, pH 7.4, 37° C.). Each well of cells was washed twice with DMEM/HEPES buffer, and then 100 μL adenosine deaminase (final concentration 10 IU/mL) and 100 μL of solutions of rolipram and cilostamide (each at a final concentration of 10 μM) were added, followed by 50 μL of the test compound (appropriate concentration) or buffer. After 15 minutes, incubation at 37° C. was terminated by removing the medium and adding 200 μL of 0.1 M HCl. Acid extracts were stored at −20° C. until assay. The amounts of cyclic AMP were determined following a protocol which utilized a cAMP binding protein (PKA) [van der Wenden et al., 1995], with the following minor modifications. The assay buffer consisted of 150 mM K$_2$HPO$_4$/10 mM EDTA/0.2% BSA FV at pH 7.5. Samples (20 mL) were incubated for 90 minutes at 0° C. Incubates were filtered over GF/C glass microfiber filters in a Brandel M-24 Cell Harvester. The filters were additionally rinsed with 4 times 2 mL 150 mM K$_2$HPO$_4$/10 mM EDTA (pH 7.5, 4° C.). Punched filters were counted in Packard Emulsifier Safe scintillation fluid after 2 hours of extraction.

Available data from the affinity testing for the compounds of the invention are reported in Table 1. The data reported for the A$_{2B}$ term is the level of displacement of specific [$^{125}$I] ABOPX binding at rat A$_{2B}$ receptors (rA$_{2B}$) expressed in HEK-293 cells.

Synthesis and Characterization

Proton nuclear magnetic resonance spectroscopy was performed on a Varian-300 MHz spectrometer and spectra were taken in DMSO-d$_6$ or CDCl$_3$. Unless noted, chemical shifts are expressed as ppm downfield from tetramethylsilane or relative ppm from DMSO (2.5 ppm). Electro-spray-ionization (ESI) mass spectrometry was performed with a ThermoFinnigan LCQ mass spectrometer.

All xanthine derivatives were homogeneous as judged using TLC (Silica gel 60 F$_{254}$, 0.25 mm, aluminium backed, EM Science, Gibbstown, N.J.) and HPLC (Shimadzu) using Varian C18 5 micron analytical column (4.6 mm×150 mm) in linear gradient or isocratic solvent system, at a flow rate of 1 ml/min. The solvent system used was MeOH (0.1% formic acid):H$_2$O (0.1% formic acid). Peaks were detected by UV absorption at 232 nm and 254 nm. NMR and mass spectra were shown to be consistent with the assigned structure.

EXAMPLE 1

General Procedure

Preparation of 6-chloronicotinoyl chloride

6-Hydroxynicotinic acid (1.444 g, 10.4 mmol) was suspended in thionyl chloride (8 ml). DMF (0.50 ml) was added. The mixture was refluxed for 2 h. After allowing the reaction to cool, thionyl chloride was removed by nitrogen stream and the residue was dried under vacuum overnight and used directly in the next step.

Preparation of 1,3-dipropyl-8-(6-chloro-3-pyridyl)xanthine (1)

6-Chloronicotinoyl chloride, prepared from 6-hydroxynicotinic acid (1.44 g, 10.4 mmol), in $CH_2Cl_2$ (20 ml) was added dropwise to a solution of 5,6-diamino-1,3-dipropyluracil (1.81 g, 8 mmol) in dry pyridine (8.2 ml) maintained at 5° C. The reaction was warmed to room temperature and stirred for an additional 3 hours. Water (50 ml) was added to quench the reaction. The solvent was evaporated to afford a dark colored oil. The oil was refluxed for 2 h in 2N NaOH (20 ml). After cooling, the pH was carefully adjusted to 7 with concentrated HCl. A solid formed and was collected and washed with water (20 ml), ether (20 ml) and chloroform (20 ml) to provide an off-white solid (1.9 g). The product was used in the next step without further purification.

General Procedures for the Reaction of 1,3-dipropyl-8-(6-chloro-3-pyridyl)xanthine (1) with Substituted Amines.

Compound 1 (40 mg, 0.115 mmol) and the corresponding substituted amine (0.5 ml or 0.5 g) were put in a pressure tube. (Ethanol, 4 ml, was added as the solvent if the melting point of the amine is above 80° C.) The pressure tube was flushed with argon, sealed and stirred at 160° C. for 48-60 h. After cooling, ether (10 ml) was added. The resulting solid was collected and purified by silica gel column or preparative TLC (Solvent A: $CH_2Cl_2$:MeOH=20:1 to 10:1 or Solvent B:$CH_2Cl_2$:MeOH:TEA=20:1:0.1 to 4:1:0.1).

General Procedures for the Preparation of Urea Compounds:

The amino substituted pyridyl compound (IC) (10 mg) was suspended in dry THF (5 ml) in a pressure tube. The isocyanate (0.25 ml) was added. The mixture was stirred at 90° C. for 48 h. After cooling, the solvent was evaporated. The residue was purified by preparative TLC ($CH_2Cl_2$: MeOH=11:1).

General Procedures for the Preparation of Amide Compounds:

The amino substituted pyridyl compound (15 mg) and the desired acid chloride (4-6 equivalents) were suspended in dry DMF (2 ml). Pyridine (0.1-0.15 ml) was added to the mixture. The mixture was stirred at room temperature for 24 h. The solvent was removed and the residue was purified by silica gel column or preparative TLC ($CH_2Cl_2$:MeOH=11:1 or Ethyl Acetate:Hexane:MeOH=15:85:5).

Preparation of 1,3-Diethyl-8-[6-hydrazino-3-pyridyl]xanthine (138)

Compound 1 (500 mg, 1.44 mmol) and hydrazine (4 ml) were put in a pressure tube. Ethanol (30 ml) was added. The pressure tube was flushed with argon, sealed and stirred at 100-160° C. for 10-16 h. After cooling, the resulting solid was collected and washed with methanol and ether to give compound 138 (40 mg). The product was used in the next step without further purification.

General Procedures for the Preparation of Compounds of Formula IL:

Compound 138 (31.5 mg, 0.1 mmol) was suspended in acetic acid (5 ml) in a pressure tube. The aldehyde or ketone (0.12 mmol) was added. The pressure tube was flushed with argon, sealed and stirred at 100-160° C. for 2-10 h. After cooling, the resulting solid was collected and purified by silica gel column or preparative TLC ($CH_2Cl_2$:MeOH=20:1 to 10:1) to give compound of Formula IL.

EXAMPLES

The following compounds of the invention were prepared using the procedures described herein-above.

Compound 1:
1,3-Dipropyl-8-(6-chloro-3-pyridyl)xanthine $^1$H NMR (DMSO, $d_6$): δ 0.89(m, 6H), 1.59(m, 2H), 1.73(m, 2H), 3.88(t, 2H, J=7.2 Hz), 4.00(t, 2H, J=7.2 Hz), 7.68(d, 1H, J=8.4 Hz), 8.50(dd, 1H, $J_1$=2.4 Hz, $J_2$=8.4 Hz), 9.07(d, 1H, J=2.4 Hz). MS: m/z 348 (M+H)$^+$.

Compound 2: 1-Propyl-3-propargyl-8-(6-chloro-3-pyridyl)xanthine

MS: m/z 316 (M+H)$^+$.

Compound 3:
1,3-Dipropyl-8-(6-ethylamino-3-pyridyl)xanthine $^1$H NMR (DMSO, d6): δ 0.89(m, 6H), 1.14(t, 3H, J=7.2 Hz), 1.56(m, 2H), 1.72(m, 2H), 3.33(m, 2H), 3.84(t, 2H, J=7.2 Hz), 3.99(t, 2H, J=7.2 Hz), 6.52(d, 1H, J=8.7 Hz), 7.09(t, 1H), 8.00(dd, 1H, $J_1$=2.4 Hz, $J_2$=8.7 Hz), 8.72(d, 1H, J=2.4 Hz). MS: m/z 357 (M+H)$^+$.

Compound 4: 1,3-Dipropyl-8-(6-(2-hydroxyethyl)amino-3-pyridyl)xanthine $^1$H NMR (DMSO, $d_6$): δ 0.88(m, 6H), 1.57(m, 2H), 1.71(m, 2H), 3.36(m, 2H), 3.53(m, 2H), 3.85(t, 2H, J=7.2 Hz), 3.99(t, 2H, J=7.2 Hz), 4.73(t, 1H, J=5.4 Hz), 6.57(d, 1H, J=8.7 Hz), 7.11(t, 1H), 7.99(dd, 1H, J=2.4 Hz, $J_2$=8.7 Hz), 8.70(d, 1H, J=2.4 Hz). MS: m/z 373 (M+H)$^+$.

Compound 5: 1,3-Dipropyl-8-[6-(4-acetylpiperazinyl)-3-pyridyl]xanthine $^1$H NMR (DMSO, $d_6$): δ 0.84(m, 6H), 1.52(m, 2H), 1.68(m, 2H), 2.00(s, 3H), 3.52(m, 8H), 3.81(t, 2H, J=7.2 Hz), 3.96(t, 2H, J=7.2 Hz), 6.92(d, 1H, J=8.7 Hz), 8.14(dd, 1H, $J_1$=2.4 Hz, $J_2$=8.7 Hz), 8.79(d, 1H, J=2.4 Hz). MS: m/z 440 (M+H)$^+$.

Compound 6:
1,3-Dipropyl-8-[6-(benzylamino)-3-pyridyl]xanthine $^1$H NMR (DMSO, $d_6$): δ 0.87(m, 6H), 1.54(m, 2H), 1.71(m, 2H), 3.84(t, 2H, J=7.2 Hz), 3.98(t, 2H, J=7.2 Hz), 4.54(d, 2H, J=6.5 Hz), 6.61(d, 1H, J=8.7 Hz), 7.22(m, 1H), 7.31(m, 4H), 7.66(t, 1H, J=6.0 Hz), 8.02(dd, 1H, $J_1$=2.4 Hz, $J_2$=8.7 Hz), 8.71(d, 1H, J=2.4 Hz). MS: m/z 419 (M+H)$^+$.

Compound 7: 1,3-Dipropyl-8-[6-(1-piperidinyl)-3-pyridyl]xanthine $^1$H NMR (DMSO, d$_6$): δ 0.88(m, 6H), 1.63(m, 10H), 3.61(t, 4H, J=5.7 Hz), 3.85(t, 2H, J=7.2 Hz), 4.00(t, 2H, J=7.2 Hz), 6.91(d, 1H, J=9.0 Hz), 8.12(dd, 1H, J$_1$=2.4 Hz, J$_2$=9.0 Hz), 8.79(d, 1H, J=2.4 Hz). MS: m/z 397 (M+H)$^+$.

Compound 8: 1,3-Dipropyl-8-(6-pyrrolidinylpyrid-3-yl)xanthine $^1$H NMR (DMSO, d$_6$): δ 0.88(m, 6H), 1.55(m, 2H), 1.73(m, 2H), 1.95(m, 4H), 3.43(m, 4H), 3.85(t, 2H, J=7.5 Hz), 4.00(t, 2H, J=7.5 Hz), 6.54(d, 1H, J=9.0 Hz), 8.12(dd, 1H, J$_1$=2.4 Hz, J$_2$=9.0 Hz), 8.79(d, 1H, J=2.4 Hz). MS: m/z 383 (M+H)$^+$.

Compound 9: 1,3-Dipropyl-8-{6-[4-methyl(perhydro-1,4-diazaepin-1-yl)]-3 pyridyl}xanthine $^1$H NMR (DMSO, d$_6$): δ 0.88(m, 6H), 1.56(m, 2H), 1.72(m, 2H), 1.88(m, 2H), 2.47(m, 5H), 2.60(m, 2H), 3.64(t, 2H. J=6.0 Hz), 3.77(m, 2H), 3.85(t, 2H, J=7.2 Hz), 3.99(t, 2H, J=7.2 Hz), 6.73(d, 1H, J=9.0 Hz), 8.12(dd, 1H, J$_1$=2.4 Hz, J$_2$=9.0 Hz), 8.78(d, 1H, J=2.4 Hz). MS: m/z 426 (M+2).

Compound 10: 1,3-Dipropyl-8-(6-methylamino-3-pyridyl)xanthine $^1$H NMR (DMSO, d$_6$): δ 0.88(m, 6H), 1.56(m, 2H), 1.72(m, 2H), 2.81(d, 3H, J=4.5 Hz), 3.85(t, 2H, J=7.5 Hz), 3.99(t, 2H, J=7.5 Hz), 6.52(d, 1H, J=8.7 Hz), 7.08(q, 1H, J=4.5 Hz), 8.01(dd, 1H, J$_1$=2.4 Hz, J$_2$=8.7 Hz), 8.73(d, 1H, J=2.4 Hz). MS: m/z 343 (M+H)$^+$.

Compound 11: 1,3-Dipropyl-8-[6-(4-methoxybenzylamino)-3-pyridyl]xanthine $^1$H NMR (DMSO, d$_6$): δ 0.87(m, 6H), 1.59(m, 2H), 1.71(m, 2H), 3.71(s, 3H), 3.87(t, 2H, J=7.2 Hz), 3.98(t, 2H, J=7.2 Hz), 4.45(d, 2H, J=6.3 Hz), 6.58(d, 1H, J=9.0 Hz), 6.87(d, 2H, J=8.7 Hz), 7.25(d, 2H, J=8.7 Hz), 7.60(t, 1H), 8.01(dd, 1H, J$_1$=2.4 Hz, J$_2$=9.0 Hz), 8.71(d, 1H, J=2.4 Hz). MS: m/z 449 (M+H)$^+$.

Compound 12: 1,3-Dipropyl-8-16-(3-methylpiperidino)-3-pyridyl]xanthine $^1$H NMR (DMSO, d$_6$): δ 0.88(m, 9H), 1.14(m, 1H), 1.40-1.80(m, 8H), 2.55(dt, 1H, J=2.1 Hz, J$_2$=10.5 Hz), 2.86(dt, 1H, J=2.1 Hz, J$_2$=10.5 Hz), 3.85(t, 2H, J=7.5 Hz), 4.00(t, 2H, J=7.5 Hz), 4.30(d, 2H, J=13.5 Hz), 6.92(d, 1H, J=9.0 Hz), 8.10(dd, 1H, J$_1$=2.4 Hz, J$_2$=9.0 Hz), 8.79(d, 1H, J=2.4 Hz). MS: m/z 411 (M+H)$^+$.

Compound, 13: 1,3-Dipropyl-8-[6-(2-hydroxypropyl)amino-3-pyridyl]xanthine $^1$H NMR (DMSO, d$_6$): δ 0.87(m, 6H), 1.08(d, 3H, J=6.0 Hz), 1.56(m, 2H), 1.72(m, 2H), 3.26(m, 2H), 3.77(m, 1H), 3.85(t, 2H, J=7.5 Hz), 3.99(t, 2H, J=7.5 Hz), 4.76(d, 1H, J=4.5 Hz), 6.60(d, 1H, J=9.0 Hz), 7.10(t, 1H, J=6.0 Hz), 7.99(dd, 1H, J$_1$=2.4 Hz, J$_2$=9.0 Hz), 8.69(d, 1H, J=2.4 Hz). MS: m/z 387 (M+H)$^+$.

Compound 14: 1,3-Dipropyl-8-[6-(2,2-dimethoxyethyl)amino-3-pyridyl]xanthine $^1$H NMR (DMSO, d$_6$): δ 0.88(m, 6H), 1.56(m, 2H), 1.72(m, 2H), 3.29(s, 6H), 3.45(t, 2H, J=5.7 Hz), 3.85(t, 2H, J=7.5 Hz), 3.99(t, 2H, J=7.5 Hz), 4.49(t, 1H, J=5.4 Hz), 6.62(d, 1H, J=9.0 Hz), 7.19(t, 1H, J=5.7 Hz), 8.00(dd, 1H, J$_1$=2.4 Hz, J$_2$=9.0 Hz), 8.71(d, 1H, J=2.4 Hz). MS: m/z 417 (M+H)$^+$.

Compound 15: 1,3-Dipropyl-8-[6-(1-hydroxy-2-propyl)amino-3-pyridyl]xanthine $^1$H NMR (DMSO, d$_6$): δ 0.88(m, 6H), 1.12(d, 3H, J=6.6 Hz), 1.56(m, 2H), 1.74(m, 2H), 3.27(m, 2H), 3.46(m, 1H), 3.85(t, 2H, J=7.2 Hz), 3.98(t, 2H, J=7.2 Hz), 4.74(t, 1H, J=5.4 Hz), 6.56(d, 1H, J=9.0 Hz), 6.90(d, 1H, J=7.5 Hz), 7.98(dd, 1H, J$_1$=2.4 Hz, J$_2$=9.0 Hz), 8.69(d, 1H, J=2.4 Hz). MS: m/z 387 (M+H)$^+$.

Compound 16: 1,3-Dipropyl-8-(6-morpholino-3-pyridyl)xanthine $^1$H NMR (DMSO, d$_6$): δ 0.87(m, 6H), 1.57(m, 2H), 1.73(m, 2H), 3.55(m, 4H), 3.69(m, 4H), 3.85(t, 2H, J=7.2 Hz), 3.99(t, 2H, J=7.2 Hz), 6.94(d, 1H, J=9.0 Hz), 8.17(dd, 1H, J$_1$=2.4 Hz, J$_2$=9.0 Hz), 8.83(d, 1H, J=2.4 Hz). MS: m/z 399 (M+H)$^+$.

Compound 17: 1,3-Dipropyl-8-(6-dimethylamino-3-pyridyl)xanthine $^1$H NMR (DMSO, d$_6$): δ 0.88(m, 6H), 1.55(m, 2H), 1.75(m, 2H), 3.09(s, 6H), 3.85(t, 2H, J=7.2 Hz), 3.99(t, 2H, J=7.2 Hz), 6.73(d, 1H, J=9.0 Hz), 8.13(dd, 1H, J$_1$=2.4 Hz, J$_2$=9.0 Hz), 8.80(d, 1H, J=2.4 Hz). MS: m/z 357 (M+H)$^+$.

Compound 18: 1,3-Dipropyl-8-[[6-(2-hydroxyethoxy)ethylamino]-3-pyridy]xanthine $^1$H NMR (DMSO, d$_6$): δ 0.88(m, 6H), 1.57(m, 2H), 1.72(m, 2H), 3.49(m, 8H), 3.85(t, 2H, J=7.5 Hz), 3.99(t, 2H, J=7.5 Hz), 4.59(t, 1H, J=5.4 Hz), 6.58(d, 1H, J=9.0 Hz), 7.15(t, 1H), 8.00(dd, 1H, J$_1$=2.4 Hz, J$_2$=9.0 Hz), 8.71(d, 1H, J=2.4 Hz), 13.42(s, 1H). MS: m/z 417 (M+H)$^+$.

Compound 19: 1,3-Dipropyl-8-(6-piperazino-3-pyridyl)xanthine $^1$H NMR (DMSO, d$_6$): δ 0.87(m, 6H), 1.56(m, 2H), 1.72(m, 2H), 2.78(m, 4H), 3.52(m, 4H), 3.85(t, 2H, J=7.5 Hz), 3.99(t, 2H, J=7.5 Hz), 6.88(d, 1H, J=9.0 Hz), 8.13(dd, 1H, J$_1$=2.4 Hz, J$_2$=9.0 Hz), 8.80(d, 1H, J=2.4 Hz). MS: m/z 398 (M+H)$^+$.

Compound 20: 1,3-Dipropyl-8-[6-(2-hydroxy-2-phenylethyl)amino-3-pyridyl]xanthine $^1$H NMR (DMSO, d$_6$): δ 0.87(m, 6H), 1.56(m, 2H), 1.72(m, 2H), 3.32(m, 1H), 3.55(m, 4H), 3.85(t, 2H, J=7.2 Hz), 3.99(t, 2H, J=7.2 Hz), 4.76(m, 1H), 5.55(d, 1H, J=4.5 Hz), 6.63(d, 1H, J=8.7 Hz), 7.20-7.40(m, 6H), 8.00(dd, 1H, J$_1$=2.4 Hz, J$_2$=8.7 Hz), 8.72(d, 1H, J=2.4 Hz), 13.42(s, 1H). MS: m/z 449 (M+H)$^+$.

Compound 21: 1,3-Dipropyl-8-[6-(4-aminomethyl-benzylamino)-3-pyridyl]xanthine $^1$H NMR (DMSO, d$_6$): δ 0.86(m, 6H), 1.55(m, 2H), 1.71(m, 2H), 3.72(s, 2H), 3.84(t, 2H, J=7.2 Hz), 3.97(t, 2H, J=7.2 Hz), 4.50(d, 1H, J=6.0 Hz), 6.57(d, 1H, J=9.0 Hz), 7.27(s, 4H), 7.54(t, 1H, J=6.0 Hz), 8.00(dd, 1H, J$_1$=2.4 Hz, J$_2$=9.0 Hz), 8.68(d, 11H, J=2.4 Hz). MS: m/z 448 (M+H)$^+$.

Compound 22: 1,3-Dipropyl-8-(6-phenylamino-3-pyridyl]xanthine $^1$H NMR (DMSO, d$_6$): δ 0.88(m, 6H), 1.55(m, 2H), 1.76(m, 2H), 3.86(t, 2H, J=7.5 Hz), 4.01(t, 2H, J=7.5 Hz), 6.93(m, 2H), 7.29(t, 2H, J=7.8 Hz), 7.68(d, 2H, J=7.8 Hz), 8.19(dd, 1H, J$_1$=2.4 Hz, J$_2$=9.0 Hz), 8.87(d, 1H, J=2.4 Hz), 9.45(s, 1H). MS: m/z 405 (M+H)$^+$.

Compound 23: 1,3-Dipropyl-8-(6-cyclopropylamino-3-pyridyl]xanthine $^1$H NMR (DMSO, d$_6$): δ 0.44(m, 2H), 0.72(m, 2H), 0.87(m, 6H), 1.56(m, 2H), 1.72(m, 2H), 2.58(m, 1H), 3.85(t, 2H, J=7.5 Hz), 3.99(t, 2H, J=7.5 Hz), 6.66(d, 1H, J=9.0 Hz), 7.36(d, 1H, J=2.7 Hz), 8.10(dd, 1H, J$_1$=2.4 Hz, J$_2$=9.0 Hz), 8.74(d, 1H, J=2.4 Hz). MS: m/z 369 (M+H)$^+$.

Compound 24: 1,3-Dipropyl-8-[6-(6-pyridylmethylamino)-3-pyridyl]xanthine $^1$H NMR (DMSO, d$_6$): δ 0.88(m, 6H), 1.56(m, 2H), 1.72(m, 2H), 3.84(t, 2H, J=7.2 Hz), 3.98(t, 2H, J=7.2 Hz), 4.62(d, 2H, J=6.0 Hz), 6.67(d, 1H, J=8.7 Hz), 7.25(m, 2H), 7.73(m, 2H0, 8.04(dd, 1H, J$_1$=2.4 Hz, J$_2$=8.7 Hz), 8.51(d, 1H, J=4.8 Hz), 8.69(d, 1H, J=2.4 Hz). MS: m/z 420 (M+H)$^+$.

Compound 25: 1,3-Dipropyl-8-(6-(4-methylpiperazino)-3-pyridyl]xanthine $^1$H NMR (DMSO, d$_6$): δ 0.87(m, 6H), 1.56(m, 2H), 1.72(m, 2H), 2.21(s, 3H), 2.38(t, 4H, J=4.8 Hz), 3.59(t, 4H, J=4.8 Hz), 3.85(t, 2H, J=7.5 Hz), 4.00(t, 2H, J=7.5 Hz), 6.93(d, 1H, J=9.0 Hz), 8.15(dd, 1H, J$_1$=2.4 Hz, J$_2$=9.0 Hz), 8.81(d, 1H, J=2.4 Hz). MS: m/z 412 (M+H)$^+$.

Compound 26: 1,3-Dipropyl-8-[6-(3-pyridylmethylamino)-3-pyridyl]xanthine $^1$H NMR (DMSO, d$_6$): δ 0.87(m, 6H), 1.56(m, 2H), 1.71(m, 2H), 3.84(t, 2H, J=7.5 Hz), 3.98(t, 2H, J=7.5 Hz), 4.56(d, 2H, J=5.7 Hz), 6.63(d, 1H, J=8.7 Hz), 7.33(dd, 1H, J$_1$=4.5 Hz, J$_2$=7.8 Hz), 7.71(m, 2H), 8.04(dd, 1H, J$_1$=2.4 Hz, J$_2$=8.7 Hz), 8.43(dd, 1H, J]=1.8 Hz, J$_2$=4.5 Hz), 8.55(d, 1H, J=1.8 Hz), 8.71(d, 1H, J=2.4 Hz). MS: m/z 420 (M+H)$^+$.

Compound 27: 1,3-Dipropyl-8-[6-(2-methylbenzylamino)-3-pyridyl]xanthine $^1$H NMR (DMSO, d$_6$): δ 0.87(m, 6H), 1.56(m, 2H), 1.72(m, 2H), 2.31(s, 3H), 3.85(t, 2H, J=7.2 Hz), 3.99(t, 2H, J=7.2 Hz), 4.50(d, 2H, J=5.4 Hz), 6.62(d, 1H, J=8.7 Hz), 7.10-7.25(m, 4H) 7.51(t, 1H, J=5.4 Hz), 8.01(dd, 1H, J$_1$=2.4 Hz, J$_2$=8.7 Hz), 8.72(d, 1H, J=2.4 Hz). MS: m/z 433 (M+H)$^+$.

Compound 28: 1,3-Dipropyl-8-[6-[2-(3,4-dimethoxyphenyl)ethylamino]-3-pyridyl]xanthine $^1$H NMR (DMSO, d$_6$): δ 0.87(m, 6H), 1.56(m, 2H), 1.72(m, 2H), 2.77(t, 2H, J=7.5 Hz), 3.49(m, 2H), 3.70(s, 3H), 3.73(s, 3H), 3.85(t, 2H, J=7.5 Hz), 3.99(t, 2H, J=7.5 Hz), 6.55(d, 1H, J=9.0 Hz), 6.74(dd, 1H, J$_1$=1.8 Hz, J$_2$=8.4 Hz), 6.85 (m, 2H), 7.17(t, 1H, J=5.4 Hz). 8.01(dd, 1H, J$_1$=2.4 Hz, J$_2$=9.0 Hz), 8.73(d, 1H, J=2.4 Hz). MS: m/z 493 (M+H)$^+$.

Compound 29: 1,3-Dipropyl-8-16-[(N-propylcarbamoyl),methylamino]-3-pyridyl)xanthine $^1$H NMR (DMSO, d$_6$): δ 0.88(m, 9H), 1.54(m, 4H), 1.72(m, 2H), 3.17(m, 2H), 3.30(d, 3H, J=5.4 Hz), 3.86(t, 2H, J=7.5 Hz), 4.01(t, 2H, J=7.5 Hz), 7.43(d, 1H, J=9.0 Hz), 8.01(dd, 1H, J$_1$=2.4 Hz, J$_2$=9.0 Hz), 8.99(d, 1H, J=2.4 Hz), 9.29(t, 1H, 5.4 Hz). MS: m/z 428 (M+H)$^+$.

Compound 30: 1,3-Dipropyl-8-[6-(3-pentylamino)-3-pyridyl]xanthine $^1$H NMR (DMSO, d$_6$): δ 0.88(m, 12H), 1.37-1.65(m, 6H), 1.72(m, 2H), 3.84(m, 3H), 3.98(t, 2H, J=7.2 Hz), 6.54(d, 1H, J=8.7 Hz), 6.90(d, 1H, J=8.4 Hz), 7.96(dd, 1H, J$_1$=2.4 Hz, J$_2$=8.7 Hz), 8.67(d, 1H, J=2.4 Hz). MS: m/z 399 (M+H)$^+$.

Compound 31: 1,3-Dipropyl-8-16-(2,2-diphenylethylamino)-3-pyridyl]xanthine $^1$H NMR (DMSO, d$_6$): δ 0.86(m, 6H), 1.54(m, 2H), 1.72(m, 2H), 3.82-4.00(m, 6H), 4.36(t, 1H, J=7.5 Hz), 6.53(d, 1H, J=9.0 Hz), 7.15-7.34(m, 11H), 7.97(dd, 1H, J$_1$=2.4 Hz, J$_2$=9.0 Hz), 8.75(d, 1H, J=2.4 Hz). MS: m/z 509 (M+H)$^+$.

Compound 32: 1,3-Dipropyl-8-[6-[2-(1-ethylpyrrolidinomethylamino)]-3-pyridyl]xanthine $^1$H NMR (DMSO, d$_6$): δ 0.88(m, 6H), 1.04(t, 2H, J=7.2 Hz), 1.50-1.86(m, 8H), 2.12(m, 1H), 2.25(m, 1H), 2.58(m, 1H), 2.86(m, 1H), 3.09(m, 2H), 3.51(m, 1H), 3.84(t, 2H, J=7.5 Hz), 3.99(t, 2H, J=7.5 Hz), 6.60(d, 1H, J=9.0 Hz), 6.98(br, 1H), 7.99(dd, 1H, J$_1$=2.4 Hz, J$_2$=9.0 Hz), 8.70(d, 1H, J=2.4 Hz). MS: m/z 440 (M+H)$^+$.

Compound 33: 1,3-Dipropyl-8-[6-(3-methoxybenzylamino)-3-pyridyl]xanthine $^1$H NMR (DMSO, d$_6$): δ 0.87(m, 6H), 1.54(m, 2H), 1.72(m, 2H), 3.71(s, 3H), 3.85(t, 2H, J=7.8 Hz), 3.99(t, 2H, J=7.8 Hz), 4.51(d, 2H, J=6.0 Hz), 6.61(d, 1H, J=9.0 Hz), 6.70-6.91(m, 3H), 7.22(t, 1H, J=7.5 Hz), 7.64(t, 1H, J=6.0 Hz), 8.02(dd, 1H, J$_1$=2.4 Hz, J$_2$=9.0 Hz), 8.71(d, 1H, J=2.4 Hz). MS: m/z 449 (M+H)$^+$.

Compound 34: 1,3-Dipropyl-8-[6-[(N-phenylcarbamoyl)methylamino]-3-pyridyl]xanthine $^1$H NMR(DMSO, d$_6$): δ 0.88(m, 6H), 1.57(m, 2H), 1.75 (m, 2H), 3.44(s, 3H), 3.86(t, 2H, J=7.5 Hz), 4.02(t, 2H, J=7.5 Hz), 7.04(t, 1H, J=7.2 Hz), 7.32(t, 2H, J=7.5 Hz), 7.48(d, 1H, J=9.0 Hz), 7.60(m, 3H), 8.47(dd, 1H, J$_1$=2.4 Hz, J$_2$=9.0 Hz), 9.12(d, 1H, J=2.4 Hz). MS: m/z 462 (M+H)$^+$.

Compound 35: 1,3-Dipropyl-8-[6-(furfurylamino)-3-pyridyl]xanthine $^1$H NMR (DMSO, d$_6$): δ 0.88(m, 6H), 1.57(m, 2H), 1.73(m, 2H), 3.87(t, 2H, J=7.5 Hz), 3.99(t, 2H, J=7.5 Hz), 4.52(d, 2H, J=5.7 Hz), 6.27(d, 1H, J=3.0 Hz), 6.38(m, 1H), 6.3(d, 1H, J=9.0 Hz), 7.56(m, 2H), 8.03(dd, 1H, J$_1$=2.4 Hz, J$_2$=9.0 Hz), 8.73(d, 1H, J=2.4 Hz). MS: m/z 409 (M+H)$^+$.

Compound 36: 1,3-Dipropyl-8-[6-[2-(4-methoxyphenyl)ethylamino]-3-pyridyl]xanthine $^1$H NMR (DMSO, d$_6$): δ 0.88(m, 6H), 1.56(m, 2H), 1.72(m, 2H), 2.77(t, 2H, J=7.5 Hz), 3.47(q, 2H, t=7.5 Hz), 3.71(s, 3H), 3.85(t, 2H, J=7.2 Hz), 3.99(t, 2H, J=7.2 Hz), 6.55(d, 1H, J=9.0 Hz), 6.85(d, 2H, J=8.4 Hz), 7.16(d, 2H, J=8.4 Hz), 8.00(dd, 1H, J$_1$=2.4 Hz, J$_2$=9.0 Hz), 8.73(d, 1H, J=2.4 Hz). MS: m/z 463 (M+H)$^+$.

Compound 37: 1,3-Dipropyl-8-16-(2-methoxybenzylamino)-3-pyridyl]xanthine $^1$H NMR (DMSO, d$_6$): δ 0.86(m, 6H), 1.56(m, 2H), 1.71(m, 2H), 3.82(s, 3H), 3.87(t, 2H, J=7.2 Hz), 3.98(t, 2H, J=7.2 Hz), 4.48(d, 2H, J=6.0 Hz), 6.62(d, 1H, J=9.0 Hz), 6.87(t, 1H, J=7.2 Hz), 6.98(d, 1H, J=7.5 Hz), 7.20(m, 2H0, 7.46(t, 1H, J=6.0 Hz); 8(dd, 1H, J$_1$=2.4 Hz, J$_2$=9.0 Hz), 8.70(d, 1H, J=2.4 Hz). MS: m/z 449 (M+H)$^+$.

Compound 38: 1,3-Dipropyl-8-[6-(propylamino)-3-pyridyl]xanthine $^1$H NMR (DMSO, d$_6$): δ 0.88(m, 9H), 1.53(m, 4H), 1.72(m, 2H), 3.24(q, 2H, J=6.3 Hz), 3.85(t, 2H, J=7.5 Hz), 3.98(t, 2H, J=7.5 Hz), 6.53(d, 1H, J=8.7 Hz), 7.13(t, 1H, J=5.7 Hz), 7.99(dd, 1H, J$_1$=2.4 Hz, J$_2$=8.7 Hz), 8.70(d, 1H, J=2.4 Hz). MS: m/z 371 (M+H)$^+$.

Compound 39: 1,3-Dipropyl-8-[6-(cyclopentylamino)-3-pyridyl]xanthine $^1$H NMR (DMSO, d$_6$): δ 0.88(m, 6H), 1.40-1.75(m, 10H), 1.72(m, 2H), 3.84(t, 2H, J=7.2 Hz), 3.99(t, 2H, J=7.2 Hz), 4.17(m, 1H), 6.52(d, 1H, J=8.7 Hz), 7.10(d, 1H, J=6.6 Hz), 7.99(dd, 1H, J$_1$=2.4 Hz, J$_2$=8.7 Hz), 8.70(d, 1H, J=2.4 Hz). MS: m/z 397 (M+H)$^+$.

Compound 40: 1,3-Dipropyl-8-[6-(cyclohexylamino)-3-pyridyl]xanthine $^1$H NMR (DMSO, d$_6$): δ 0.88(m, 6H), 1.13-1.91(m, 14H), 1.72(m, 2H), 3.76(m, 1H), 3.84(t, 2H, J=7.5 Hz), 3.98(t, 2H, J=7.5 Hz), 6.52(d, 1H, J=9.0 Hz), 7.00(d, 1H, J=7.8 Hz), 7.97(dd, 1H, J$_1$=2.4 Hz, J$_2$=9.0 Hz), 8.69(d, 1H, J=2.4 Hz). MS: m/z 411 (M+H)$^+$.

Compound 41: 1,3-Dipropyl-7-ethyl-8-(6-chloro-3-pyridyl)xanthine $^1$H NMR (DMSO, d$_6$): δ 0.88(m, 6H), 1.33(t, 3 h, J=7.2 Hz), 1.59(m, 2H), 1.73(m, 2H), 3.87(t, 2H, J=7.5 Hz), 3.99(t, 2H, J=7.5 Hz), 7.74(d, 1H, J=8.4 Hz), 8.19(dd, 1H, J$_3$=2.4 Hz, J$_2$=8.4 Hz), 8.74(d, 1H, J=2.4 Hz). MS: m/z 376 (M+H)$^+$.

Compound 42: 1,3-Dipropyl-7-(3-fluoropropyl-8-(6-chloro-3-pyridyl)xanthine $^1$H NMR (DMSO, d$_6$): δ 0.88(m, 6H), 1.56(m, 2H), 1.72(m, 2H), 2.09(m, 1H), 2.18(m, 1H), 3.89(t, 2H, J=7.5 Hz), 3.98(t, 2H, J=7.5 Hz), 4.29(t, 1H, J=5.4 Hz), 4.43(m, 3H), 7.75(dd, 1H, J1=0.6 Hz, J2=8.4 Hz), 8.19(dd, 1H, J$_1$=2.4 Hz, J$_2$=8.4 Hz), 8.74(dd, 1H, J=0.6 Hz, J$_2$=2.4 Hz). MS: m/z 408 (M+H)$^+$.

Compound 43: 1,3-Dipropyl-7-methyl-8-(6-chloro-3-pyridyl)xanthine $^1$H NMR (DMSO, d$_6$): δ 0.87(m, 6H), 1.56(m, 2H), 1.72(m, 2H), 3.86(t, 2H, J=7.5 Hz), 3.99(t, 2H, J=7.5 Hz), 4.01(s, 3H), 7.74(d, 1H, J=8.4 Hz), 8.26(dd, 1H, J=2.4 Hz, J$_2$=8.4 Hz), 8.82(d, 1H, J=2.4 Hz). MS: m/z 362 (M+H)$^+$.

Compound 44: 1,3-Dipropyl-7(2-bromoethyl)-8-(6-chloro-3-pyridyl)xanthine $^1$H NMR (DMSO, d$_6$): δ 0.88(m, 6H), 1.59(m, 2H), 1.72(m, 2H), 3.85(m, 4H), 3.99(t, 2H, J=7.5 Hz), 4.66(t, 2H, J=6.0 Hz), 7.76(d, 1H, J=8.11 Hz), 8.21(dd, 1H, J$_1$=2.7 Hz, J2=8.1 Hz), 8.76(d, 1H, J=2.7 Hz). MS: m/z 456 (M+H)$^+$.

Compound 45: 1,3-Dipropyl-8-[6-(2-thiophenemethylamino)-3-pyridyl]xanthine $^1$H NMR (DMSO, d$_6$): δ 0.88(m, 6H), 1.56(m, 2H), 1.72(m, 2H), 3.85(t, 2H, J=7.5 Hz), 3.99(t, 2H, J=7.5 Hz), 4.70(d, 2H, J=6.0 Hz), 6.60(d, 1H, J=8.7 Hz), 6.94-7.03(m, 2H), 7.35(dd, 1H, J$_1$=1.5 Hz, J$_2$=5.1 Hz), 7.70 (t, 1H, J=6.0 Hz), 8.04(dd, 1H, J$_1$=2.4 Hz, J$_2$=8.7 Hz), 8.75(d, 1H, J=2.4 Hz). MS: m/z 425 (M+H)$^+$.

Compound 46: 1,3-Dipropyl-8-[6-[(N-(4-methoxyphenylcarbamoyl)methylamino]-3-pyridyl]xanthine $^1$H NMR (DMSO, d$_6$): δ 0.89(m, 6H), 1.56(m, 2H), 1.73(m, 2H), 3.43(s, 3H), 3.73(s, 3H), 3.87(t, 2H, J=7.2 Hz), 4.02(t, 2H, J=7.2 Hz), 6.89(dd, 2H, J=6.9 Hz), 7.48(m, 3H), 8.47(dd, 1H, J$_1$=2.4 Hz, J$_2$=9.0 Hz), 9.11(d, 1H, J=2.4 Hz). MS: m/z 492 (M+H)$^+$.

Compound 47: 1,3-Dipropyl-8-[6-[N-nicotinoylmethylamino]-3-pyridyl]xanthine $^1$H NMR (DMSO, d$_6$): δ 0.87(m, 6H), 1.57(m, 2H), 1.73(m, 2H), 3.49(s, 3H), 3.86(t, 2H, J=7.2 Hz), 3.99(t, 2H, J=7.2 Hz), 7.35(dd, 1H, J$_1$=7.8 Hz, J$_2$=7.8 Hz), 7.41(d, 1H, J=8.4 Hz), 7.71(dt, 1H, J$_1$=1.5 Hz, J$_2$=8.4 Hz,), 8.32(dd, 1H, J$_1$=2.4 Hz, J$_2$=8.4 Hz), 8.46(d, 1H, J=2.1), 8.54(dd, 1H, J$_1$=2.1 Hz, J$_2$=4.8 Hz), 8.98(d, 1H, J=2.4 Hz). MS: m/z 448 (M+H)$^+$.

Compound 48: 1,3-Dipropyl-8-[6-[(N-(4-fluorophenylcarbamoyl)methylamino]-3-pyridyl]xanthine $^1$H NMR (DMSO, d$_6$): δ 0.88(m, 6H), 1.57(m, 2H), 1.75(m, 2H), 3.44(s, 3H), 3.88(t, 2H, J=7.5 Hz), 4.03(t, 2H, J=7.5 Hz), 7.15(t, 2H, J=8.7 Hz), 7.49(d, 1H, J=9.0 Hz), 7.62(m, 2H), 8.47(dd, 1H, J$_1$=2.4 Hz, J$_2$=9.0 Hz), 9.12(d, 1H, J=2.4 Hz). MS: m/z 480 (M+H)$^+$.

Compound 49: 1,3-Dipropyl-8-[6-[N-isonicotinoyl-methylamino]-3-pyridyl)xanthine $^1$H NMR (DMSO, d$_6$): δ 0.88(m, 6H), 1.57(m, 2H), 1.75(m, 2H), 3.47(s, 3H), 3.85(t, 2H, J=7.5 Hz), 3.99(t, 2H, J=7.5 Hz), 7.26(d, 2H, J=5.4 Hz), 7.46(d, 1H, J=8.7 Hz), 8.34(dd, 1H, J$_1$=2.4 Hz, J$_2$=8.7 Hz), 8.54(d, 2H, J=5.4 Hz), 8.96(d, 1H, J=2.4 Hz). MS: m/z 448 (M+H)$^+$.

Compound 50: 1,3-Dipropyl-8-[6-[N-methoxycarbonylmethylamino]-3-pyridyl)xanthine MS: m/z 401 (M+H)$^+$.

Compound 51: 1,3-Dipropyl-8-[6-[N-phenylcarbamoyl, N-(2 phenylcarbamoyloxyethyl)amino]-3-pyridyl)xanthine $^1$H NMR (DMSO, d$_6$): δ 0.88(m, 6H), 1.57(m, 2H), 1.75(m, 2H), 3.87(t, 2H, J=7.5 Hz), 4.03(t, 2H, J=7.5 Hz), 4.34(m, 4H), 6.92-7.57(m, 11H), 8.44(dd, 1H, J=2.4 Hz, J$_2$=8.7 Hz), 9.12(d, 1H, J=2.4 Hz), 9.58(s (br), 1H). MS: m/z 611 (M+H)$^+$.

Compound 52: 1,3-Dipropyl-8-{6-[4-(N-phenylcarbamoyl)]piperazino-3-pyridyl}xanthine $^1$H NMR (DMSO, d$_6$): δ 0.88(m, 6H), 1.56(m, 2H), 1.73(m, 2H), 3.57(m, 4H), 3.67(m, 4H), 3.86(t, 2H, J=7.2 Hz), 4.01(t, 2H, J=7.2 Hz), 6.93(t, 1H, J=7.8 Hz), 6.99(d, 1H, J=9.0 Hz), 7.23(t, 2H, J=7.8 Hz), 7.46(d, 2H, J=7.8 Hz), 8.19(dd, 1H, J$_1$=2.4 Hz, J$_2$=9.0 Hz), 8.61(s, 1H), 8.85(d, 1H, J=2.4 Hz). MS: m/z 517 (M+H)$^+$. Compound 53: 1,3-Dipropyl-8-{6-[4-(N-isonicotinoyl)]piperazino-3-pyridyl}xanthine $^1$H NMR (DMSO, d$_6$): δ 0.88(m, 6H), 1.56(m, 2H), 1.73(m, 2H), 3.38(m, 2H), 3.64(m, 2H), 3.75(m, 4H), 3.86(t, 2H, J=7.2 Hz), 4.00(t, 2H, J=7.2 Hz), 6.96(d, 1H, J=9.0 Hz), 7.44(d, 2H, J=5.1 Hz), 8.19(dd, 1H, J$_1$=2.4 Hz, J$_2$=9.0 Hz), 8.69(d, 2H, J=5.1 Hz), 8.84(d, 1H, J=2.4 Hz). MS: m/z 503 (M+H)$^+$.

Compound 54: 1-propyl-3-(4-methoxyphenyl)ethyl-8-(6-chloro-3-pyridyl)xanthine $^1$H NMR (DMSO, d$_6$): δ 0.84(t, 3H, J=7.2 Hz), 1.53(m, 2H), 2.93(t, 2H, J=7.2 Hz) 3.67(s, 3H), 3.83(t, 2H, J=7.2 Hz), 4.20(t, 2H, J=7.2 Hz), 6.81(d, 2H, J=8.1 Hz), 7.12(d, 2H, J=8.1 Hz), 7.68(d, 1H, J=8.4 Hz), 8.44(dd, 1H, J1=2.4 Hz, J$_2$=8.4 Hz), 8.98(d, 1H, J=2.4 Hz MS: m/z 440 (M+H)$^+$.

Compound 55: 1-Propyl-3-(methoxyphenylethyl)-8-(6-piperazino-3-pyridyl)xanthine $^1$H NMR (DMSO, d$_6$): δ 0.84(m, 3H), 1.52(m, 2H), 3.38(m, 2H), 2.77(m, 4H), 2.94(t, 2H, J=7.5 Hz), 3.51(m, 4H), 3.69(s, 1H), 3.83(t, 2H, J=7.5 Hz), 4.20(t, 2H, J=7.5 Hz), 6.83(d, 2H, J=8.4 Hz), 6.89(d, 1H, J=9.0 Hz), 7.14(d, 2H, J=8.4 Hz), 8.14(dd, 1H, J$_1$=2.4 Hz, J$_2$=9.0 Hz), 8.82(d, 1H, J=2.4 Hz). MS: m/z 490 (M+H)$^+$.

Compound 56: 1,3-Dipropyl-8-[6-(4-pyridylamino)-3-pyridyl]xanthine $^1$H NMR (DMSO, d$_6$): δ 0.87(m, 6H), 1.56(m, 2H), 1.74(m, 2H), 3.87(t, 2H, J=7.5 Hz), 4.03(t, 2H, J=7.5 Hz), 6.30(d, 2H, J=7.8 Hz), 7.94(d, 1H, J=8.7 Hz), 8.53(d, 1H, J=7.8 Hz), 8.60(dd, 1H, J$_1$=2.4 Hz, J$_2$=8.7 Hz), 9.17(d, 1H, J=2.4 Hz). MS: m/z 407 (M+2)$^+$.

Compound 57: 1,3-Dipropyl-8-{6-[4-(N-nicotinoyl)]piperazino-3-pyridyl}xanthine $^1$H NMR (DMSO, d$_6$): δ 0.88(m, 6H), 1.56(m, 2H), 1.74(m, 2H), 3.46-3.83(m, 8H), 3.88(t, 2H, J=7.5 Hz), 4.00(t, 2H, J=7.5 Hz), 6.96(d, 1H, J=9.0 Hz), 7.50(dd, 1H, J$_1$=7.8 Hz, J$_2$=7.8 Hz), 7.89(d, J=7.5 Hz), 8.19 (dd, 1H, J$_1$=2.4 Hz, J$_2$=9.0 Hz), 8.66(m, 2H), 8.84(d, 1H, J=2.4 Hz). MS: m/z 503 (M+H)$^+$.

Compound 58: 1,3-Dipropyl-8-[6-(hexahydro-1,4-diazaepin-1-yl)-3-pyridyl]xanthine $^1$H NMR (DMSO, d$_6$): δ 0.87(m, 6H), 1.56(m, 2H), 1.74(m, 4H), 2.66(t, 2H, J=5.4 Hz), 2.86(t, 2H, J=5.4 Hz), 3.68(m, 4H), 3.85(t, 2H, J=7.5 Hz), 3.99(t, 2H, J=7.5 Hz), 6.72(d, 1H, J=9.0 Hz), 8.10(dd, 1H, J$_1$=2.4 Hz, J$_2$=9.0 Hz), 8.77(d, 1H, J=2.4 Hz). MS: m/z 412 (M+H)$^+$.

Compound 59: 1,3-Diethyl-8-(6-chloro-3-pyridyl)xanthine $^1$H NMR (DMSO, d$_6$): δ 1.14(t, 3H, J=6.9 Hz), 1.26(t, 3H, J=6.9 Hz), 3.94(q, 2H, J=6.9 Hz), 4.09(q, 2H, J=6.9 Hz), 7.68(d, 1H, J=8.4 Hz), 8.46(dd, 1H, J$_1$=2.4 Hz, J$_2$=8.4 Hz), 9.07(d, 1H, J=2.4 Hz). MS: m/z 320 (M+H)$^+$.

Compound 60: 1,3-Diethyl-8-(6-piperazino-3-pyridyl)xanthine

MS: m/z 370 (M+H)$^+$.

Compound 61: 1,3-Diethyl-8-[6-[(N-phenylcarbamoyl)methylamino]-3-pyridyl)xanthine MS: m/z 434 (M+H)$^+$.

Compound 62: 1,3-Diethyl-8-[6-[N-nicotinoylethylamino]-3-pyridyl)xanthine

MS: m/z 434 (M+H)$^+$.

Compound 63: 1,3-Diethyl-8-(6-methylamino-3-pyridyl)xanthine

MS: m/z 315 (M+H)$^+$.

Compound 64: 1,3-Diethyl-8-[6-[N-nicotinoylmethylamino]-3-pyridyl)xanthine

MS: m/z 420 (M+H)$^+$.

Compound 65: 1,3-Diethyl-8-[6-[N-nicotinoylcyclopropylamino]-3-pyridyl)xanthine

MS: m/z 446 (M+H)$^+$.

Compound 66: 1,3-Dicyclopropylmethyl-8-(6-methylaminopyridin-3-yl)xanthine

MS: m/z 367 (M+H)$^+$.

Compound 67: 1-Propargyl-3-methyl-8-(6-methylamino-3-pyridyl)xanthine

MS: m/z 311 (M+H)$^+$.

Compound 68: 8-[6-(2,5-diaza-bicyclo[2.2.2]oct-2-yl)-pyridin-3-yl}-1,3-dipropyl-3,7-dihydro-purine-2,6-dione MS: m/z 410 (M+H)$^+$.

Compound 69: 1,3-Dicylopropylmethyl-8-[6-(N-nicotinoylmethylamino]-3-pyridyl)xanthine MS: m/z 472 (M+H)$^+$.

Compound 70: 1,3-Dicylopropylmethyl-8-[6-[N-nicotinoylethylamino]-3-pyridyl)xanthine MS: m/z 486 (M+H)$^+$.

Compound 71: 1,3-Diallyl-8-(6-methylamino-3-pyridyl)xanthine

MS: m/z 339 (M+H)$^+$.

Compound 72: 1-Clopropylmethyl-3-ethyl-8-(6-methylaminopyridin-3-yl)xanthine

MS: m/z 342 (M+H)$^+$.

Compound 73: 1,3-Diethyl-8-[6-(2-pyridylmethylamino)-3-pyridyl]xanthine

MS: m/z 392 (M+H)$^+$.

Compound 74: 1,3-Diethyl-8-[6-(3-pyridylmethylamino)-3-pyridyl]xanthine

MS: m/z 392 (M+H)$^+$.

Compound 75: 1,3-Diethyl-8-[6-(3-methoxybenzylamino)-3-pyridyl]xanthine

MS: m/z 421 (M+H)$^+$.

Compound 76: 1,3-Dipropyl-8-[6-[2-(3-pyridyl)-ethylamino]-3-pyridyl]xanthine

MS: m/z 434 (M+H)$^+$.

Compound 77: 1,3-Diethyl-8-[6-[2-(3-pyridyl)-ethylamino]-3-pyridyl]xanthine

MS: m/z 406 (M+H)$^+$.

Compound 78: 1,3-Dipropyl-8-[6-[2-(2-pyridyl)-ethylamino]-3-pyridyl]xanthine

MS: m/z 434 (M+H)$^+$.

Compound 79: 1,3-Diethyl-8-[6-[2-(2-pyridyl)-ethylamino]-3-pyridyl]xanthine

MS: m/z 406 (M+H)$^+$.

Compound 80: 1,3-Diethyl-8-(6-pyrrolidinylpyrid-3-yl)xanthine

MS: m/z 355 (M+H)$^+$.

Compound 81: 1,3-Diethyl-8-[6-[2-(1-pyrrolidinyl)-ethylamino]-3-pyridyl]xanthine MS: m/z 398 (M+H)$^+$.

Compound 82: 1,3-Dipropyl-8-(6-(2-methoxyethyl)amino-3-pyridyl)xanthine

MS: m/z 387 (M+H)$^+$.

Compound 83: 1,3-Dipropyl-8-(6-(2-acetylaminoethyl)amino-3-pyridyl)xanthine

MS: m/z 414 (M+H)$^+$.

Compound 84: 1,3-Diethyl-8-(6-bromo-3-pyridyl)xanthine

MS: m/z 364 (M+H)$^+$.

Compound 85: 1,3-Dipropyl-8-{6-[4-(2-pyridyl)-piperazino]-3-pyridyl}xanthine

MS: m/z 475 (M+H)$^+$.

Compound 86: 1,3-Dithyl-8-{6-[4-(2-pyridyl)-piperazino]-3-pyridyl}xanthine

MS: m/z 447 (M+H)$^+$.

Compound 87: 1,3-Diethyl-8-[6-(trans-2,5-dimethylpiperazino)-3-pyridyl]xanthine

MS: m/z 398 (M+H)$^+$.

Compound 88: 1,3-Dipropyl-8-{6-[4-(2-pyrimidinyl)-piperazino]-3-pyridyl}xanthine MS: In/z 476 (M+H)$^+$.

Compound 89: 1,3-Diethyl-8-{6-[4-(2-pyrimidinyl)-piperazino]-3-pyridyl}xanthine

MS: m/z 448 (M+H)$^+$.

Compound 90: 1,3-Diethyl-8-(6-(2-methoxyethyl)amino-3-pyridyl)xanthine

MS: m/z 359 (M+H)$^+$.

Compound 91: 1-Propargyl, 3-methyl-8-(6-Bromo-3-pyridyl)xanthine

MS: m/z 360 (M+H)$^+$.

Compound 92: 1,3-Diethyl-8-[6-[N-nicotinoyl, N-(2-methoxyethyl)amino]-3-pyridyl]xanthine MS: m/z 464 (M+H)$^+$.

Compound 93: 1-Propargyl, 3-methyl-8-(6-(2-methoxyethyl)-3-pyridyl)xanthine

MS: m/z 355 (M+H)$^+$.

Compound 94: 1,3-Diethyl-8-[6-[N-isonicotinoyl, N-(2-methoxyethyl)amino]-3-pyridyl)xanthine MS: m/z 464 (M+H)$^+$.

Compound 95: 1-(5-(1,3-Diethyl-2,3,6,7-tetrahydro-2,6-dioxo-1H-purin-8-yl)pyridin-2-yl)-1-(2-methoxyethyl)-3-(pyridine-4-yl)urea MS: m/z 479 (M+H)$^+$.

Compound 96: 1,3-Dimethyl-8-(6-bromo-3-pyridyl)xanthine

MS: m/z 460 (M+H)$^+$.

Compound 97: 1,3-Dimethyl-8-(6-methylamino-3-pyridyl)xanthine

MS: m/z 287 (M+H)$^+$.

Compound 98: 1,3-Dimethyl-8-[6-[N-nicotinoylmethylamino]-3-pyridyl)xanthine

MS: m/z 392 (M+H)$^+$.

Compound 99: 1,3-Dipropyl-8-[6-[N-nicotinoyl, N-(2-methoxyethyl)amino]-3-pyridyl)xanthine MS: m/z 492 (M+H)$^+$.

Compound 100: 1-Propargyl, 3-methyl-8-[6-[N-nicotinoyl, N-(2-methoxyethyl)amino]-3-pyridyl)xanthine MS: m/z 359 (M+H)$^+$.

Compound 101: 1-Propargyl, 3-methyl-8-[6-[N-nicotinoylmethylamino]-3-pyridyl)xanthine MS: m/z 416 (M+H)$^+$.

Compound 102: 1,3-Dipropyl-8-(2,6-dichloro-3-pyridyl)xanthine

MS: m/z 382 (M+H)$^+$.

Compound 103: 1,3-Dipropyl-8-(2,6-dimethylamino-3-pyridyl)xanthine

MS: m/z 372 (M+H)$^+$.

Compound 104: 1,3-Dipropyl-8-(2,6-di(2-methoxyethyl)-3-pyridyl)xanthine

MS: m/z 460 (M+H)$^+$.

Compound 105: 1,3-Dipropyl-8-[2,6-di[N-nicotinoylmethylamino]-3-pyridyl)xanthine MS: m/z 582 (M+H)$^+$.

Compound 106: 1,3-Dipropyl-8-12,6-di[N-nicotinoyl, N-methoxyethyl]-3-pyridyl)xanthine MS: m/z 670 (M+H)$^+$.

Compound 107: 1,3-Diethyl-8-[6-[N-(2-pyrazinecarbonyl)methylamino]-3-pyridyl)xanthine MS: m/z 421 (M+H)$^+$.

Compound 108: 1,3-Diethyl-8-[6-[N-(isoxazole-5-carbonyl)methylamino]-3-pyridyl)xanthine MS: m/z 410 (M+H)$^+$.

Compound 109: 1,3-Dipropyl-8-[6-[N-(2-pyrazinecarbonyl)methylamino]-3-pyridyl)xanthine MS: m/z 449 (M+H)$^+$.

Compound 110: 1,3-Dipropyl-8-[6-[N-(isoxazole-5-carbonyl)methylamino]-3-pyridyl)xanthine MS: m/z 438 (M+H)$^+$.

Compound 111: 1,3-Dipropyl-8-[6-[N-(5-methylisoxazol-3-yl-3-carbonyl)methylamino]-3-pyridyl)xanthine MS: m/z 452 (M+H)$^+$.

Compound 112: 1,3-Dipropyl-8-[6-[N-(2-chloro-6-methoxypyridinyl-4-carbonyl), N-methylamino]-3-pyridyl)xanthine MS: m/z 512 (M+H)$^+$.

Compound 113: 1,3-Dipropyl-8-[6-[N-(Isonicotinoyl N-oxide), N-methylamino]-3-pyridyl)xanthine MS: m/z 464 (M+H)$^+$.

Compound 114: 1-propyl-3-(4-methoxyphenyl)ethyl-8-(6-methylamino-3-pyridyl)xanthine MS: m/z 435 (M+H)$^+$.

Compound 115: 1,3-Diethyl-8-[6-(N-(Isonicotinoyl N-oxide), N-methylamino]-3-pyridyl)xanthine MS: m/z 436 (M+H)$^+$.

Compound 116: 1,3-Diallyl-8-(6-chloro-3-pyridyl)xanthine

MS: m/z 344 (M+H)$^+$.

Compound 117: 1-propyl-3-(4-methoxyphenyl)ethyl-8-[6-(N-nicotinoylmethylamino)-3-pyridyl)xanthine MS: m/z 540 (M+H)$^+$.

Compound 118: 1-propyl-3-(4-methoxyphenyl)ethyl-8-[6-(N-(6-chloronicotinoyl)methylamino)-3-pyridyl]xanthine MS: m/z 574 (M+H)$^+$.

Compound 119: 1,3-diallyl-8-[6-(N-nicotinoylmethylamino)-3-pyridyl]xanthine

MS: m/z 444 (M+H)$^+$.

Compound 120: 1,3-diallyl-8-[6-(N-(6-chloronicotinoyl)methylamino)-3-pyridyl]xanthine MS: m/z 478 (M+H)+.

Compound 121: 1,3-dipropyll-8-16-(N-[6-(trifluoromethyl)nicotinoyl]methylamino)-3-pyridyl]xanthine MS: m/z 516 (M+H)+.

Compound 122: 1,3-diethyl-8-[6-(2-hydroxy-5-methyl)benzaldehydehydrazono]-3-pyridyl]xanthine MS: m/z 434 (M+H)+.

Compound 123: 1-Cyclopropyl-3-propyl-8-[6-(N-[6-(trifluoromethyl)nicotinoyl]methylamino)-3-pyridyl]xanthine MS is m/z 446.

Compound 124: 1,3-diethyl-8-[6-(bromopyridine-3-carbaldehydehydrazono]-3-pyridyl]xanthine MS: m/z 483 (M+H)+.

Compound 125: 1-Cyclopropyl-3-ethyl-8-(6-methylamino-3-pyridyl)xanthine

MS: m/z 327 (M+H)+.

Compound 126: 1-Cyclopropyl-3-propyl-8-(6-methylamino-3-pyridyl)xanthine

MS: m/z 341 (M+H)+.

Compound 127: 1-Propyl-3-cyclopropyl-8-(6-methylamino-3-pyridyl)xanthine

MS: m/z 341 (M+H)+.

Compound 128: 1-Cyclopropyl-3-propyl-8-(6-(2-methoxyethyl)amino-3-pyridyl)xanthine MS: m/z 385 (M+H)+.

Compound 129: 1-Cyclopropyl-3-propyl-8-(6-[N-nicotinoylmethylamino]-3-pyridyl)xanthine MS: m/z 446 (M+H)+.

Compound 130: 1,3-Diethyl-8-[6-(N-(6-chloronicotinoyl)methylamino)-3-pyridyl]xanthine MS: m/z 454 (M+H)+.

Compound 131: 1,3-Dipropyl-8-(2-chloro-6-methoxyethylamino-4-pyridyl)xanthine

MS: m/z 421 (M+H)+.

Compound 132: 1,3-Dipropyl-8-(2-chloro-6-methylamino-4-pyridyl)xanthine

MS: m/z 377 (M+H)+.

Compound 133: 1,3-Dipropyl-8-[2-[N-nicotinoyl,N-(2-methoxyethyl)amino]-6-chloro-4-pyridyl)xanthine MS: m/z 527 (M+H)+.

Compound 134: 1,3-Dipropyl-8-[2-[N-nicotinoyl,N-methylamino]-6-chloro-4-pyridyl)xanthine MS: m/z 482 (M+H)+.

Compound 135: 1-Cyclopropyl-3-propyl-8-[6-[N-(6-chloronicotinoyl)methylamino]-3-pyridyl)xanthine MS: m/z 480 (M+H)+.

Compound 136: 1-Ethyl-3-cyclopropyl-8-(6-methylamino-3-pyridyl)xanthine

MS: m/z 327 (M+H)+.

Compound 137: 1-Ethyl-3-cyclopropyl-8-(6-(2-methoxyethyl)amino-3-pyridyl)xanthine MS: m/z 371 (M+H)+.

Compound 138: 1,3-Diethyl-8-[6-hydrazino-3-pyridyl]xanthine

MS: m/z 316 (M+H)+.

Compound 139: 1,3-Diethyl-8-[6-(cyclopropylamino)-3-pyridyl]xanthine

MS: m/z 341 (M+H)+.

Compound 140: 1,3-Diethyl-8-[6-(cyclopropylmethylamino)-3-pyridyl]xanthine

MS: m/z 355 (M+H)+.

Compound 141: N'-[5-(1,3-diethyl-2,6-dioxo-2,3,6,7-tetrahydro-1H-purin-8-yl)-pyridin-2-yl]-hydrazide MS: m/z 421 (M+H)+.

Compound 142: N-[5-(1,3-diethyl-2,6-dioxo-2,3,6,7-tetrahydro-1H-purin-8-yl)-pyridin-2-yl —N'-(pyridine-3-carbonyl)-hydrazide MS: m/z 526 (M+H)+.

Compound 143: 1,3-Diethyl-8-[6-(ethylamino)-3-pyridyl]xanthine

MS: m/z 329 (M+H)+.

Compound 144: 1,3-Diethyl-8-[6-[N-nicotinoylcyclopropylmethylamino]-3-pyridyl]xanthine MS: m/z 460 (M+H)+.

Compound 145: 1-Cyclopropylmethyl-3-ethyl-8-[6-[N-(6-chloronicotinoyl)methylamino]-3-pyridyl)xanthine MS: m/z 480 (M+H)+.

What is claimed is:

1. A compound of formula I:

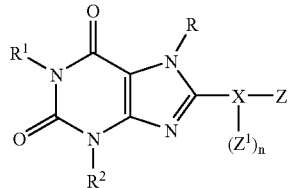

wherein:

R is hydrogen, $(C_1-C_5)$alkyl, halo$(C_1-C_8)$alkyl, $(C_3-C_5)$alkenyl, or $(C_3-C_5)$alkynyl;

$R^1$ and $R^2$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_4-C_{10})$heterocycle, $(C_4-C_{10})$heterocycle$(C_1-C_8)$alkyl-, $(C_6-C_{10})$aryl, $(C_6-C_{10}$ aryl$(C_1-C_8)$alkyl-, $(C_5-C_{10})$heteroaryl, or $(C_5$ $C_{10})$heteroaryl$(C_1-C_8)$alkyl-;

X is

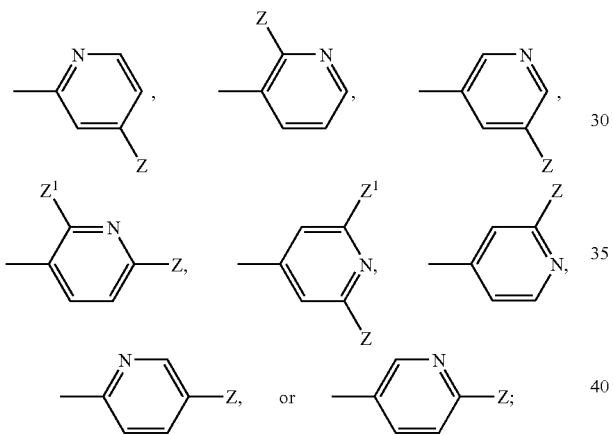

Z is $-OR^3$, $-SR^3$, $-S(O)_m-NR^4R^5$, $-NR^4R^5$, or $(C_4-C_{10})$heterocycle wherein the heterocycle is optionally substituted with 1, 2, 3, or 4 substituents independently selected from halo, cyano, nitro, $-OR^a$, $-SR^a$, $(C_1-C_8)$alkyl, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $-C(O)NR^bR^c$; provide that X-(Z')$_n$-Z is other than 6-(pyrid-2-yl)-pyrid-2yl;

each $Z^1$ is independently $(C_1-C_8)$alkyl, $(C_2-C_8)$alkenyl, $(C_2-C_8)$alkynyl, $-OR^6$, $-SR^6$, halo, $R^6O(C_1-C_8)$alkyl, $R^7R^8N(C_1-C_8)$alkyl, halo$(C_1-C_8)$alkyl, $-NR^7R^8$, $R^7R^8N(C_1-C_8)$alkyl, $-C(O)R^6$, $-COOR^6$, and $-C(O)NR^7R^8$;

$R^3$ is $(C_1-C_8)$alkyl, $(C_3-C_8)$alkenyl, $(C_3-C_8)$alkynyl, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, $-C(O)R^6$, or $-C(O)NR^7R^8$;

$R^4$ and $R^5$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_6-C_{18})$polycycloalkyl, $(C_6-C_{18})$polycycloalkyl$(C_1-C_8)$alkyl-, $(C_3-C_{10})$heterocycle, $(C_3-C_{10})$heterocycle$(C_1-C_8)$alkyl-, $-NR^7R^8$, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, $-C(O)R^6$, $-CO_2R^6$, $-C(O)NR^7R^8$, or $-S(O)_2-NR^7R^8$; or $R^4$ and $R^5$ together with the atoms to which they are attached form a saturated or partially unsaturated, mono-, bicyclic- or aromatic ring having 3, 4, 5, 6, 7, or 8, ring atoms and optionally comprising 1, 2, 3, or 4 heteroatoms selected from non-peroxide oxy ($-O-$), thio ($-S-$), sulfinyl ($-SO-$), sulfonyl ($-S(O)_2-$) and amine $-N(R^9)-$ in the ring, and wherein the ring is optionally substituted with 1, 2, 3, or 4 substituents independently selected from halo, cyano, nitro, $-OR^a$, $-SR^a$, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $-C(O)NR^bR^c$;

$X^1$ is $-OR^6$, $-C(O)R^6$, $-CO_2R^6$, or $-NR^7R^8$; and Y is oxy ($-O-$), thio ($-S-$), sulfinyl ($-SO-$), sulfonyl ($-S(O)_2-$) and amine $-N(R^9)-$;

wherein the alkyl, alkenyl, cycloalkyl, alkynyl, aryl, heterocycle or heteroaryl groups of $R^1$, $R^2$, $R^3$, $R^4$ and $R^5$ groups are optionally substituted with one or more substituents independently selected from halo, cyano, nitro, $-OR^a$, $-SR^a$, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $-C(O)NR^bR^c$;

wherein $R^6$ is hydrogen, $(C_1-C_8)$alkyl, $R^aO(C_1-C_8)$alkyl, $R^bR^cN(C_1-C_8)$alkyl, halo$(C_1-C_8)$alkyl, $(C_3-C_{10})$heterocycle, $(C_3-C_{10})$heterocycle$(C_1-C_8)$alkyl-, $(C_6-C_{10})$aryl, $(C_6-C_{10})$aryl$(C_1-C_8)$alkyl-, $(C_4-C_{10})$heteroaryl, $(C_4-C_{10})$heteroaryl$(C_1-C_8)$alkyl-; wherein the heterocycle, heteroaryl or aryl are optionally substituted with 1, 2, 3, or 4 substituents independently selected from halo, cyano, nitro, $-OR^a$, $-SR^a$, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $C(O)NR^bR^c$;

wherein $R^7$, $R^8$ and $R^9$ are independently hydrogen, $(C_1-C_8)$alkyl, $R^aO(C_1-C_8)$alkyl, $R^bR^cN(C_1-C_8)$alkyl, halo$(C_1-C_8)$alkyl, $(C_3-C_{10})$heterocycle, $(C_6-C_{10})$aryl, $(C_6-C_{10})$aryl$(C_1-C_8)$alkyl-, $(C_4-C_{10})$heteroaryl; $-COOR^a$, $-C(O)R^a$, or $-C(O)NR^bR^c$ wherein the heterocycle, heteroaryl or aryl are optionally substituted with 1, 2, 3, or 4 substituents independently selected from halo, cyano, nitro, $-OR^a$, $-SR^a$, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $-C(O)NR^bR^c$; or $R^7$ and $R^8$ together with the atoms to which they are attached form a saturated or partially unsaturated, mono-, bicyclic- or aromatic ring having 3, 4, 5, 6, 7, or 8, ring atoms optionally ring having from 4 to eight ring atoms and optionally comprising 1, 2, 3, or 4 heteroatoms selected from non-peroxide oxy ($-O-$), thio ($-S-$), sulfinyl ($-SO-$), sulfonyl ($-S(O)_2-$) or amine $-N(R^b)-$ in the ring;

$R^a$ is hydrogen, or $(C_1-C_6)$alkyl; $R^b$ and $R^c$ are each independently hydrogen, $(C_1-C_6)$alkyl, $(C_1-C_6)$alkoxy, $(C_3-C_8)$cycloalkyl, $(C_1-C_6)$alkylthio, $(C_6-C_{10})$aryl, $(C_6-C_{10})$aryl$(C_1-C_6)$alkyl-, heteroaryl, or heteroaryl$(C_1-C_6)$alkyl-; or $R^b$ and $R^c$ together with the nitrogen to which they are attached, form a pyrrolidyl, piperidyl, piperazinyl, azepinyl, diazepinyl, morpholinyl, or thiomorpholinyl ring; and where n is 0, 1, 2, 3, 4, 5, 6, 7, or 8; m is 1, or 2; and q is 1, 2, 3, or 4; or a pharmaceutically acceptable salt thereof.

2. The compound of claim 1, wherein R is hydrogen, methyl, ethyl, allyl, propargyl, i-propyl, n-propyl, n-butyl, i-butyl or halo($C_1$-$C_4$)alkyl.

3. The compound of claim 1, wherein R is hydrogen, methyl, ethyl, —$CH_2$—$CH_2$—Cl, —$CH_2$—$CH_2$—Br, or —$CH_2$—$CH_2$—$CH_2$—F.

4. The compound of claim 1, wherein R is hydrogen.

5. The compound of claim 1, wherein $R^1$ is hydrogen, ($C_1$-$C_4$)alkyl, ($C_3$-$C_4$)alkenyl, ($C_3$-$C_4$)alkynyl, phenyl, or phenyl($C_1$-$C_4$)alkyl.

6. The compound of claim 1, wherein $R^1$ is ($C_3$-$C_6$)cycloalkyl and ($C_3$-$C_6$)cycloalkyl($C_1$-$C_4$)alkyl-.

7. The compound of claim 1, wherein $R^1$ is cyclopropyl or cyclopropylmethyl.

8. The compound of claim 1, wherein $R^1$ is hydrogen, methyl, ethyl, allyl, propargyl, i-propyl, n-propyl, n-butyl, i-butyl, phenyl, phenethyl, benzyl, or (methoxyphenyl)ethyl.

9. The compound of claim 1, wherein $R^1$ is ethyl, n-propyl or allyl.

10. The compound of claim 1, wherein $R^2$ is hydrogen, ($C_1$-$C_4$)alkyl, ($C_3$-$C_4$)alkenyl, ($C_3$-$C_4$)alkynyl, phenyl, phenyl($C_1$-$C_4$)alkyl, or (methoxyphenyl)ethyl.

11. The compound of claim 1, wherein $R^2$ is ($C_3$-$C_6$)cycloalkyl or ($C_3$-$C_6$)cycloalkyl($C_1$-$C_4$)alkyl-.

12. The compound of claim 1, wherein $R^2$ is cyclopropyl or cyclopropylmethyl.

13. The compound of claim 1, wherein $R^2$ is hydrogen, methyl, ethyl, allyl, propargyl, i-propyl, n-propyl, n-butyl, i-butyl, phenyl, phenethyl, or benzyl.

14. The compound of claim 1, wherein $R^2$ is ethyl, n-propyl or allyl.

15. The compound of claim 1, wherein Z is —O($C_1$-$C_4$)alkyl, —O($C_6$-$C_{10}$)aryl, —O($C_6$-$C_{10}$)aryl($C_1$-$C_4$)alkyl, —$NR^4R^5$, F, Cl, Br, or I.

16. The compound of claim 1, wherein $R^4$ is hydrogen, ($C_1$-$C_6$)alkyl, ($C_3$-$C_6$)cycloalkyl, ($C_3$-$C_6$)cycloalkyl($C_1$-$C_4$)alkyl-, ($C_3$-$C_6$)heterocycle, ($C_6$-$C_{10}$)aryl, ($C_6$-$C_{10}$)aryl($C_1$-$C_4$)alkyl-, ($C_5$-$C_6$)heteroaryl, or ($C_5$-$C_6$)heteroaryl($C_1$-$C_4$)alkyl-, —$S(O_2)NH_2$, —$C(O)R^6$, —$CO_2R^6$, or —$C(O)NR^6R^7$.

17. The compound of claim 1, wherein $R^4$ is hydrogen, ($C_1$-$C_4$)alkyl, hydroxy($C_2$-$C_4$)alkyl, ($C_3$-$C_6$)cycloalkyl, ($C_6$-$C_{10}$)aryl, ($C_7$-$C_{10}$)aralkyl, ($C_5$-$C_6$)heteroaryl, —($CH_2$—$CH_2$—O)$_q$—($CH_2$—$CH_2$)—$OR^a$, —($CH_2$—$CH_2$—O)$_q$—($CH_2$—$CH_2$)—$COOR^a$, —($CH_2$—$CH_2$—O)$_q$—($CH_2$—$CH_2$)—$NR^aR^b$, —$NR^7R^8$, —$C(O)R^6$, —$CO_2R^6$, or —$C(O)NR^7R^8$.

18. The compound of claim 1, wherein $R^4$ is hydrogen, methyl, ethyl, propyl, pentyl, hydroxyethyl, hydroxypropyl, ethoxyethyl, diethoxyethyl, methylbenzyl, aminomethylbenzyl, methoxybenzyl, methoxyphenethyl, furylmethyl, cyclopropyl, cyclopropylmethyl, cyclopentyl, cyclohexyl, thiophenyl, —$C(O)R^6$, —$CO_2R^6$, or —$C(O)NHR^7$.

19. The compound of claim 1, wherein $R^4$ is methyl, ethyl, cyclopropyl, cyclopropylmethyl, —$C(O)R^6$, —$CO_2R^6$, or —$C(O)NHR^7$.

20. The compound of claim 1, wherein $R^5$ is hydrogen, ($C_1$-$C_6$)alkyl, ($C_3$-$C_6$)cycloalkyl, ($C_3$-$C_6$)cycloalkyl($C_1$-$C_4$)alkyl-, ($C_3$-$C_6$)heterocycle, ($C_6$-$C_{10}$)aryl, ($C_6$-$C_{10}$)aryl ($C_1$-$C_4$)alkyl-, ($C_5$-$C_6$)heteroaryl, ($C_5$-$C_6$)heteroaryl($C_1$-$C_4$)alkyl-, —$S(O_2)NH_2$, —$C(O)R^6$, —$CO_2R^6$, or —$C(O)NR^6R^7$.

21. The compound of claim 1, wherein $R^5$ is hydrogen, ($C_6$-$C_4$)alkyl, hydroxy($C_2$-$C_4$)alkyl, ($C_3$-$C_6$)cycloalkyl, ($C_6$-$C_{10}$)aryl, ($C_7$-$C_{10}$)aralkyl, ($C_5$-$C_6$)heteroaryl, —($CH_2$—$CH_2$—O)$_q$—($CH_2$—$CH_2$)—$OR^a$, —($CH_2$—$CH_2$—O)$_q$—($CH_2$—$CH_2$)—$COOR^a$, —($CH_2$—$CH_2$—O)$_q$—($CH_2$—$CH_2$)—$NR^aR^b$, —$NR^7R^8$, —$C(O)R^6$, —$CO_2R^6$, or —$C(O)NR^7R^8$.

22. The compound of claim 1, wherein $R^5$ is hydrogen, methyl, ethyl, propyl, pentyl, hydroxyethyl, hydroxypropyl, ethoxyethyl, diethoxyethyl, methylbenzyl, aminomethylbenzyl, methoxybenzyl, methoxyphenethyl, furylmethyl, cyclopentyl, cyclohexyl, thiophenyl, —$C(O)R^6$, —$CO_2R^6$, or —$C(O)NHR^7$.

23. The compound of claim 1, wherein $R^5$ is methyl, ethyl, cyclopropyl, cyclopropylmethyl, —$C(O)R^6$, —$CO_2R^6$, or —$C(O)NHR^7$.

24. The compound of claim 1, wherein $R^4$ and $R^5$ taken together with the nitrogen to which they are attached, is a pyrrolidyl, piperidyl, piperazinyl, azepinyl, diazepinyl, morpholinyl, or thiomorpholinyl ring, each optionally substituted with 1, 2, 3, or 4 substituents independently selected from halo, cyano, nitro, —$OR^a$, —$SR^a$, ($C_6$-$C_{10}$)aryl, —O($C_6$-$C_{10}$)aryl, hydroxy($C_1$-$C_8$)alkyl, $R^bR^cN$($C_1$-$C_8$)alkyl, halo($C_1$-$C_8$)alkyl, —$NR^bR^c$, —$C(O)R^a$, —$COOR^a$, and —$C(O)NR^bR^c$.

25. The compound of claim 1, wherein $R^6$ is ($C_1$-$C_6$)alkyl, ($C_3$-$C_6$)cycloalkyl, ($C_3$-$C_6$)cycloalky($C_1$-$C_4$)alkyl-, ($C_3$-$C_6$)heterocycle, ($C_6$-$C_{10}$)aryl, ($C_6$-$C_{10}$)aryl($C_1$-$C_4$)alkyl-, ($C_5$-$C_6$)heteroaryl, or ($C_5$-$C_6$)heteroaryl($C_1$-$C_4$)-alkyl-, each optionally substituted with 1, 2, or 3 substituents independently selected from the group consisting of halo, cyano, nitro, ($C_1$-$C_8$)alkyl, —$OR^a$, —$SR^a$, ($C_6$-$C_{10}$)aryl, —O($C_6$-$C_{10}$)aryl, hydroxy($C_1$-$C_8$)alkyl, $R^bR^cN$($C_1$-$C_8$)alkyl, halo($C_1$-$C_8$)alkyl, —$NR^bR^c$, —$C(O)R^a$, —$COOR^a$, and —$C(O)NR^bR^c$.

26. The compound of claim 1, wherein $R^6$ is ($C_6$-$C_{10}$)aryl, ($C_5$-$C_6$)heteroaryl, each optionally substituted with 1, 2, or 3 substituents independently selected from halo, cyano, nitro, ($C_1$-$C_8$)alkyl, halo($C_1$-$C_8$)alkyl, —$COOR^a$, and —$C(O)NR^bR^c$.

27. The compound of claim 1, wherein $R^6$ is pyridyl, optionally substituted with F, Cl, Br, I, $CF_3$, cyano, nitro, —$COOR^a$, or —$CONHR^a$.

28. The compound of claim 1, wherein:
R is hydrogen, methyl, or ethyl;
$R^1$ and $R^2$ are independently methyl, ethyl, allyl, propargyl, i-propyl, n-propyl, cyclopropyl, cyclopropylmethyl, or n-butyl; and
X is 3-pyridyl substituted in the 6 position with Z, wherein Z is ($C_4$-$C_{10}$)heterocycle or —$NR^4R^5$, wherein $R^4$ is methyl, ethyl, cyclopropyl, cyclopropylmethyl and $R^5$ is —$C(O)R^6$, wherein $R^6$ is heteroaryl optionally substituted with 1, 2 or 3 substituents independently selected from halo, cyano, nitro, halo($C_1$-$C_8$)alkyl, —$C(O)R^a$, —$COOR^a$, and —$C(O)NR^bR^c$, and wherein $R^a$, $R^b$ and $R^c$ are independently hydrogen, methyl, ethyl, propyl, isopropyl, or cyclopropyl.

29. The compound of claim 1, wherein $R^1$ and $R^2$ are independently hydrogen, ($C_1$-$C_4$)alkyl, ($C_3$-$C_4$)alkenyl, ($C_3$-$C_4$)alkynyl, phenyl, or phenyl($C_1$-$C_4$)alkyl.

30. The compound of claim 1, wherein R is hydrogen, methyl, ethyl, allyl, propargyl, i-propyl, n-propyl, n-butyl, i-butyl or halo($C_1$-$C_4$)alkyl; and $R^1$ and $R^2$ are independently hydrogen, methyl, ethyl, allyl, propargyl, i-propyl, n-propyl, cyclopropyl, cyclopropylmethyl, n-butyl, i-butyl, phenyl, phenethyl, or benzyl.

31. The compound of claim 1, wherein R is hydrogen, methyl, ethyl, —$CH_2$—$CH_2$—Cl, —$CH_2$—$CH_2$—Br, or —$CH_2$—$CH_2$—F; and $R^1$ and $R^2$ are independently hydrogen, methyl, ethyl, allyl, propargyl, i-propyl, n-propyl, cyclopropyl, cyclopropylmethyl, or (methoxyphenyl)ethyl.

32. The compound of claim 1, wherein —X(Z¹)ₙ-Z has the formula

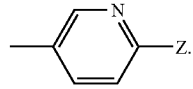

33. The compound of claim 1, wherein Z is —O(C₁-C₄)alkyl, —OC(O)NR⁷R⁸, (C₁-C₄)alkyl, —NR⁴R⁵, F, Cl, Br, or I, wherein R⁴ and R⁵ are independently hydrogen, (C₁-C₆)alkyl, (C₃-C₆)cycloalkyl, (C₃-C₆)heterocycle, (C₆-C₁₀)aryl, (C₇-C₁₂)aralkyl, (C₅-C₆)heteroaryl, or (C₅-C₆)heteroaryl(C₁-C₄)alkyl, —S(O₂)NH₂, —C(O)R⁶, —CO₂R⁶, or —C(O)NR⁶R⁷.

34. The compound of claim 1, wherein Z is —NR⁴R⁵.

35. The compound of claim 1, wherein R⁴ and R⁵ together with the nitrogen to which they are attached, form a pyrrolidyl, piperidyl, piperazinyl, azepinyl, diazepinyl, morpholinyl, or thiomorpholinyl ring, wherein the ring is optionally substituted with 1, 2, 3, or 4 substituents independently selected from halo, cyano, nitro, —OR^a, —SR^a, (C₆-C₁₀)aryl, —O(C₆-C₁₀)aryl, hydroxy(C₁-C₈)alkyl, R^bR^cN(C₁-C₈)alkyl, halo(C₁-C₈)alkyl, —NR^bR^c, —C(O)R^a, —COOR^a, and —C(O)NR^bR^c.

36. The compound of claim 1, wherein R⁴ and R⁵ are independently hydrogen, (C₁-C₄)alkyl, hydroxy(C₂-C₄)alkyl, (C₃-C₆)cycloalkyl, (C₆-C₁₀)aryl, (C₇-C₁₀)aralkyl, (C₅-C₆)heteroaryl, —(CH₂—CH₂—O)_q—(CH₂—CH₂)—OR^a, —(CH₂—CH₂—O)_q—(CH₂—CH₂)—COOR^a, —(CH₂—CH₂—O)_q—(CH₂—CH₂)—NR^aR^b, —NR⁷R⁸, —C(O)R⁶, —CO₂R⁶, or —C(O)NR⁷R⁸.

37. The compound of claim 1, wherein R⁴ and R⁵ are independently hydrogen, methyl, ethyl, propyl, pentyl, hydroxyethyl, hydroxypropyl, ethoxyethyl, diethoxyethyl, methylbenzyl, aminomethylbenzyl, methoxybenzyl, methoxyphenethyl, furylmethyl, cyclopentyl, cyclohexyl, thiophenyl, —C(O)R⁶, —CO₂R⁶, or —C(O)NHR⁷.

38. The compound of claim 1, wherein R⁶ is methyl, methoxy, or pyridyl, and R⁷ is phenyl, fluorophenyl, or methoxyphenyl.

39. The compound of claim 1, wherein:
R is hydrogen, methyl, or ethyl;
R¹ and R² are independently methyl, ethyl, allyl, propargyl, i-propyl, n-propyl, cyclopropyl, cyclopropylmethyl, n-butyl, i-butyl; and
Z is (C₄-C₁₀)heterocycle wherein the heterocycle is optionally substituted with 1, 2, 3, or 4 substituents independently selected from halo, cyano, nitro, —OR^a, —SR^a, (C₆-C₁₀)aryl, —O(C₆-C₁₀)aryl, hydroxy(C₁-C₈)alkyl, R^bR^cN(C₁-C₈)alkyl, halo(C₁-C₈)alkyl, —NR^bR^c, —C(O)R^a, —COOR^a, and —C(O)NR^bR^c.

40. The compound of claim 1, wherein Z is selected from the group consisting of:

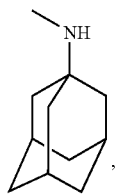, 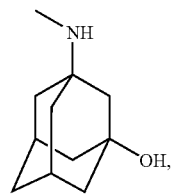, 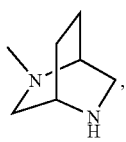,

-continued

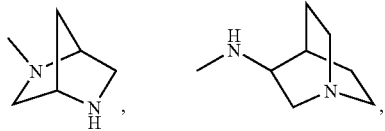

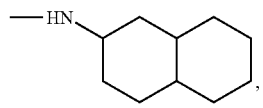

, 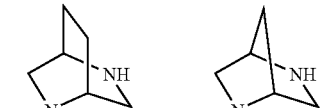

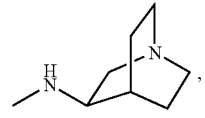, 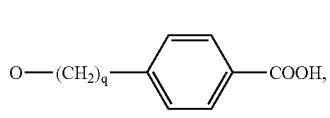

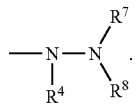.

41. The compound of claim 1, wherein —X(Z¹)ₙ-Z is selected from the group consisting of:

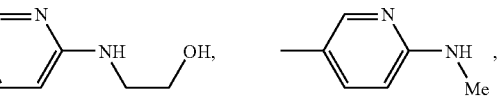

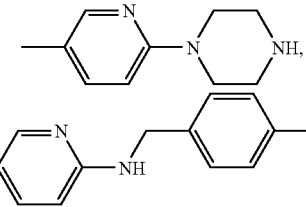

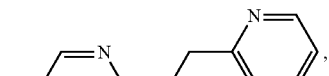

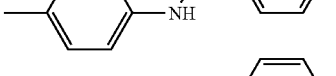

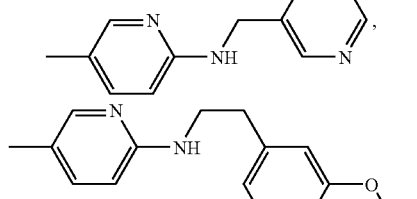

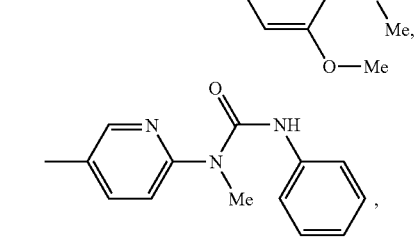

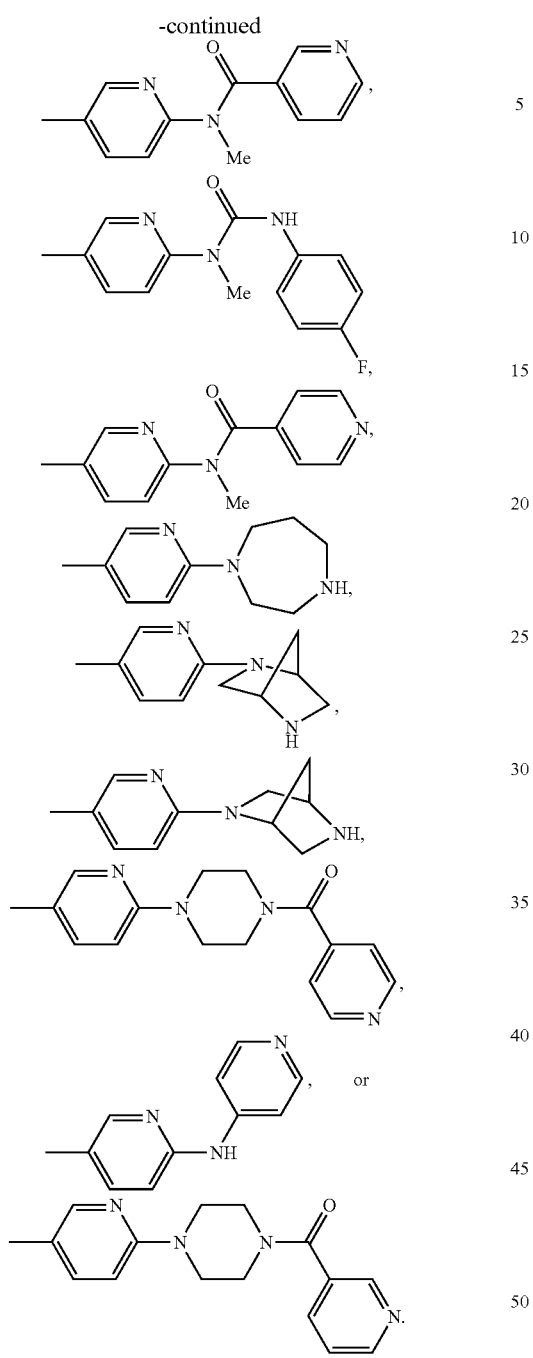
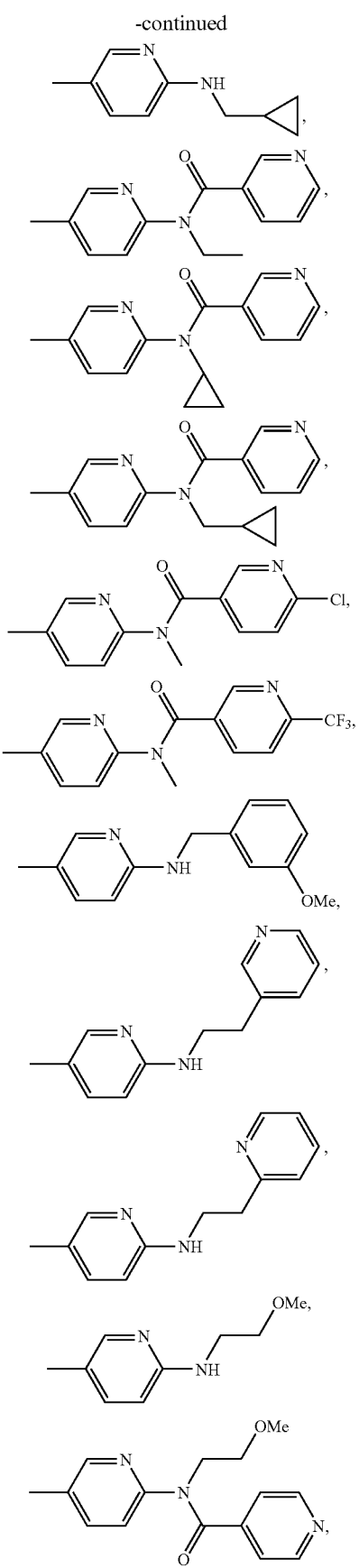
wherein Me is methyl.
42. The compound of claim 1, wherein $R^1$ and $R^2$ are n-propyl; R is hydrogen and n is zero.
43. The compound of claim 1, wherein —X($Z^1$)$_n$-Z is selected from the group consisting of:
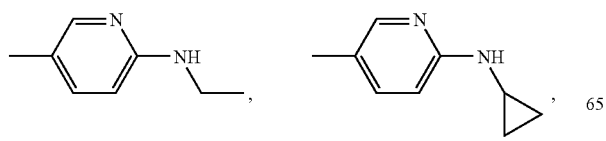

-continued

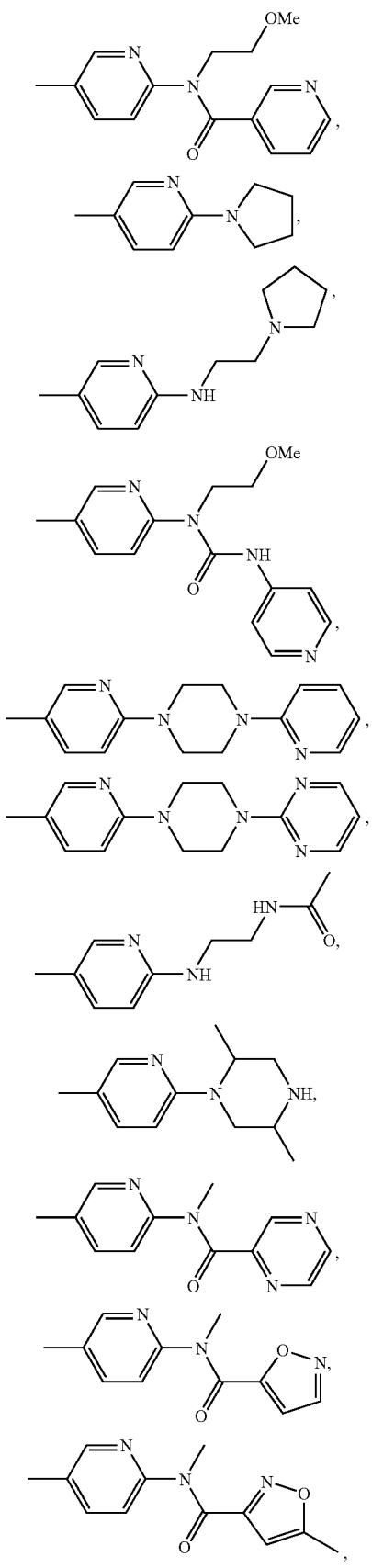

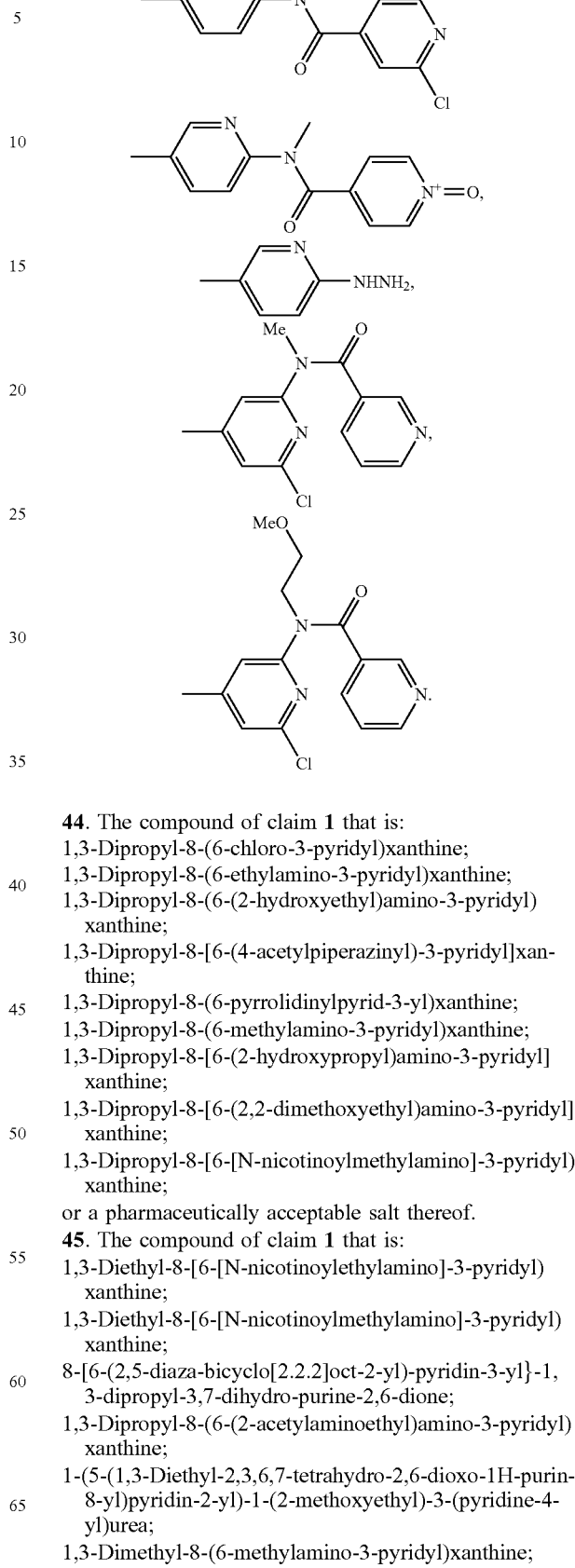

44. The compound of claim 1 that is:
1,3-Dipropyl-8-(6-chloro-3-pyridyl)xanthine;
1,3-Dipropyl-8-(6-ethylamino-3-pyridyl)xanthine;
1,3-Dipropyl-8-(6-(2-hydroxyethyl)amino-3-pyridyl) xanthine;
1,3-Dipropyl-8-[6-(4-acetylpiperazinyl)-3-pyridyl]xanthine;
1,3-Dipropyl-8-(6-pyrrolidinylpyrid-3-yl)xanthine;
1,3-Dipropyl-8-(6-methylamino-3-pyridyl)xanthine;
1,3-Dipropyl-8-[6-(2-hydroxypropyl)amino-3-pyridyl] xanthine;
1,3-Dipropyl-8-[6-(2,2-dimethoxyethyl)amino-3-pyridyl] xanthine;
1,3-Dipropyl-8-[6-[N-nicotinoylmethylamino]-3-pyridyl) xanthine;
or a pharmaceutically acceptable salt thereof.

45. The compound of claim 1 that is:
1,3-Diethyl-8-[6-[N-nicotinoylethylamino]-3-pyridyl) xanthine;
1,3-Diethyl-8-[6-[N-nicotinoylmethylamino]-3-pyridyl) xanthine;
8-[6-(2,5-diaza-bicyclo[2.2.2]oct-2-yl)-pyridin-3-yl}-1, 3-dipropyl-3,7-dihydro-purine-2,6-dione;
1,3-Dipropyl-8-(6-(2-acetylaminoethyl)amino-3-pyridyl) xanthine;
1-(5-(1,3-Diethyl-2,3,6,7-tetrahydro-2,6-dioxo-1H-purin-8-yl)pyridin-2-yl)-1-(2-methoxyethyl)-3-(pyridine-4-yl)urea;
1,3-Dimethyl-8-(6-methylamino-3-pyridyl)xanthine;

1-Propargyl, 3-methyl-8-[6-[N-nicotinoylmethylamino]-3-pyridyl)xanthine;
1,3-Diethyl-8-[6-[N-(isoxazole-5-carbonyl)methylamino]-3-pyridyl)xanthine;
1,3-Dipropyl-8-[6-[N-(2-pyrazinecarbonyl)methylamino]-3-pyridyl)xanthine;
1,3-Dipropyl-8-[6-[N-(isoxazole-5-carbonyl)methylamino]-3-pyridyl)xanthine;
1-Cyclopropyl-3-propyl-8-[6-[N-nicotinoylmethylamino]-3-pyridyl)xanthine; and
1,3-Diethyl-8-[6-[N-nicotinoylcyclopropylmethylamino]-3-pyridyl)xanthine;
or a pharmaceutically acceptable salt thereof.

46. A compound of claim 1 selected from the group consisting of:
1,3-Dipropyl-8-{6-[4-methyl(perhydro-1,4-diazaepin-1-yl)]-3 pyridyl}xanthine;
1,3-Dipropyl-8-[6-(1-hydroxy-2-propyl)amino-3-pyridyl]xanthine;
1,3-Dipropyl-8-(6-morpholino-3-pyridyl)xanthine;
1,3-Dipropyl-8-(6-dimethylamino-3-pyridyl)xanthine;
1,3-Dipropyl-8-(6-piperazino-3-pyridyl)xanthine;
1,3-Dipropyl-8-[6-(4-aminomethylbenzylamino)-3-pyridyl]xanthine;
1,3-Dipropyl-8-(6-cyclopropylamino-3-pyridyl]xanthine;
1,3-Dipropyl-8-[6-[N-isonicotinoylmethylamino]-3-pyridyl)xanthine; and
1,3-Dipropyl-8-[6-(hexahydro-1,4-diazaepin-1-yl)-3-pyridyl]xanthine;
or a pharmaceutically acceptable salt thereof.

47. A compound of claim 1 selected from the group consisting of:
1,3-Dicylopropylmethyl-8-[6-[N-nicotinoylmethylamino]-3-pyridyl)xanthine;
1,3-Dicylopropylmethyl-8-[6-[N-nicotinoylethylamino]-3-pyridyl)xanthine;
1,3-Diethyl-8-[6-(2-pyridylmethylamino)-3-pyridyl]xanthine;
1,3-Diethyl-8-[6-(3-pyridylmethylamino)-3-pyridyl]xanthine;
1,3-Diethyl-8-[6-(3-methoxybenzylamino)-3-pyridyl]xanthine;
1,3-Dipropyl-8-[6-[2-(2-pyridyl)-ethylamino]-3-pyridyl]xanthine;
1,3-Diethyl-8-[6-[2-(1-pyrrolidinyl)-ethylamino]-3-pyridyl]xanthine;
1,3-Dipropyl-8-[6-[N-(5-methylisoxazol-3-yl-3-carbonyl)methylamino]-3-pyridyl)xanthine; and
1,3-Diethyl-8-[6 (N-(6-chloronicotinoyl)methylamino)-3-pyridyl]xanthine;
or a pharmaceutically acceptable salt thereof.

48. A compound of claim 1 selected from the group consisting of:
1-Propyl-3-propargyl-8-(6-chloro-3-pyridyl)xanthine;
1,3-Dipropyl-8-(6-ethylamino-3-pyridyl)xanthine;
1,3-Dipropyl-8-(6-(2-hydroxyethyl)amino-3-pyridyl)xanthine;
1,3-Dipropyl-8-[6-(4-acetylpiperazinyl)-3-pyridyl]xanthine;
1,3-Dipropyl-8-[6-(benzylamino)-3-pyridyl]xanthine;
1,3-Dipropyl-8-[6-(1-piperidinyl)-3-pyridyl]xanthine;
1,3-Dipropyl-8-(6-pyrrolidinylpyrid-3-yl)xanthine;
1,3-Dipropyl-8-{6-[4-methyl(perhydro-1,4-diazaepin-1-yl)]-3 pyridyl}xanthine;
1,3-Dipropyl-8-(6-methylamino-3-pyridyl)xanthine;
1,3-Dipropyl-8-[6-(4-methoxybenzylamino)-3-pyridyl]xanthine;
1,3-Dipropyl-8-[6-(3-methylpiperidino)-3-pyridyl]xanthine;
1,3-Dipropyl-8-[6-(2-hydroxypropyl)amino-3-pyridyl]xanthine;
1,3-Dipropyl-8-[6-(2,2-dimethoxyethyl)amino-3-pyridyl]xanthine;
1,3-Dipropyl-8-[6-(1-hydroxy-2-propyl)amino-3-pyridyl]xanthine;
1,3-Dipropyl-8-(6-morpholino-3-pyridyl)xanthine;
1,3-Dipropyl-8-(6-dimethylamino-3-pyridyl)xanthine;
1,3-Dipropyl-8-(6-piperazino-3-pyridyl)xanthine;
1,3-Dipropyl-8-[6-(2-hydroxy-2-phenylethyl)amino-3-pyridyl]xanthine;
1,3-Dipropyl-8-[6-(4-aminomethylbenzylamino)-3-pyridyl]xanthine;
1,3-Dipropyl-8-(6-phenylamino-3-pyridyl]xanthine;
1,3-Dipropyl-8-(6-cyclopropylamino-3-pyridyl]xanthine;
1,3-Dipropyl-8-[6-(6-pyridylmethylamino)-3-pyridyl]xanthine;
1,3-Dipropyl-8-(6-(4-methylpiperazino)-3-pyridyl)xanthine;
1,3-Dipropyl-8-[6-(3-pyridylmethylamino)-3-pyridyl]xanthine;
1,3-Dipropyl-8-[6-(2-methylbenzylamino)-3-pyridyl]xanthine;
1,3-Dipropyl-8-[6-[2-(3,4-dimethoxyphenyl)ethylamino]-3-pyridyl]xanthine;
1,3-Dipropyl-8-[6-[(N-propylcarbamoyl), methylamino]-3-pyridyl)xanthine;
1,3-Dipropyl-8-[6-(3-pentylamino)-3-pyridyl]xanthine;
1,3-Dipropyl-8-[6-(2,2-diphenylethylamino)-3-pyridyl]xanthine;
1,3-Dipropyl-8-[6-[2-(1-ethylpyrrolidin-2-yl)methylamino)]-3-pyridyl]xanthine;
1,3-Dipropyl-8-[6-(3-methoxybenzylamino)-3-pyridyl]xanthine;
1,3-Dipropyl-8-[6-[(N-phenylcarbamoyl)methylamino]-3-pyridyl)xanthine;
1,3-Dipropyl-8-[6-(furfurylamino)-3-pyridyl]xanthine;
1,3-Dipropyl-8-[6-[2-(4-methoxyphenyl)ethylamino]-3-pyridyl]xanthine;
1,3-Dipropyl-8-[6-(2-methoxybenzylamino)-3-pyridyl]xanthine;
1,3-Dipropyl-8-[6-(propylamino)-3-pyridyl]xanthine;
1,3-Dipropyl-8-[6-(cyclopentylamino)-3-pyridyl]xanthine;
1,3-Dipropyl-8-[6-(cyclohexylamino)-3-pyridyl]xanthine;
1,3-Dipropyl-7-ethyl-8-(6-chloro-3-pyridyl)xanthine;
1,3-Dipropyl-7-(3-fluoropropyl-8-(6-chloro-3-pyridyl)xanthine;
1,3-Dipropyl-7-methyl-8-(6-chloro-3-pyridyl)xanthine;
1,3-Dipropyl-7(2-bromoethyl)-8-(6-chloro-3-pyridyl)xanthine;
1,3-Dipropyl-8-[6-(2-thiophenemethylamino)-3-pyridyl]xanthine;
1,3-Dipropyl-8-[6-[(N-(4-methoxyphenylcarbamoyl)methylamino]-3-pyridyl)xanthine;
1,3-Dipropyl-8-[6-[N-nicotinoylmethylamino]-3-pyridyl)xanthine;
1,3-Dipropyl-8-[6-[(N-(4-fluorophenylcarbamoyl)methylamino]-3-pyridyl)xanthine;
1,3-Dipropyl-8-[6-[N-isonicotinoylmethylamino]-3-pyridyl)xanthine;
1,3-Dipropyl-8-[6-[N-methoxycarbonylmethylamino]-3-pyridyl)xanthine;

1,3-Dipropyl-8-[6-[N-phenylcarbamoyl, N-(2 phenylcarbamoyloxyethyl)amino]-3-pyridyl)xanthine;
1,3-Dipropyl-8-{6-[4-(N-phenylcarbamoyl)]piperazino-3-pyridyl}xanthine;
1,3-Dipropyl-8-{6-[4-(N-isonicotinoyl)]piperazino-3-pyridyl}xanthine;
1-propyl-3-(4-methoxyphenyl)ethyl-8-(6-chloro-3-pyridyl)xanthine;
1-Propyl-3-(methoxyphenylethyl)-8-(6-piperazino-3-pyridyl)xanthine;
1,3-Dipropyl-8-[6-(4-pyridylamino)-3-pyridyl]xanthine;
1,3-Dipropyl-8-{6-[4-(N-nicotinoyl)]piperazino-3-pyridyl}xanthine;
1,3-Dipropyl-8-[6-(hexahydro-1,4-diazaepin-1-yl)-3-pyridyl]xanthine;
1,3-Diethyl-8-(6-chloro-3-pyridyl)xanthine;
1,3-Diethyl-8-(6-piperazino-3-pyridyl)xanthine;
1,3-Diethyl-8-[6-[(N-phenylcarbamoyl)methylamino]-3-pyridyl)xanthine;
1,3-Diethyl-8-[6-[N-nicotinoylethylamino]-3-pyridyl)xanthine;
1,3-Diethyl-8-(6-methylamino-3-pyridyl)xanthine;
1,3-Diethyl-8-[6-[N-nicotinoylmethylamino]-3-pyridyl)xanthine;
1,3-Diethyl-8-[6-[N-nicotinoylcyclopropylamino]-3-pyridyl)xanthine;
1,3-Dicyclopropylmethyl-8-(6-methylaminopyridin-3-yl)xanthine;
1-Propargyl-3-methyl-8-(6-methylamino-3-pyridyl)xanthine;
8-[6-(2,5-diaza-bicyclo[2.2.2]oct-2-yl)-pyridin-3-yl}-1,3-dipropyl-3,7-dihydro-purine-2,6-dione;
1,3-Dicylopropylmethyl-8-[6-[N-nicotinoylmethylamino]-3-pyridyl)xanthine;
1,3-Dicylopropylmethyl-8-[6-[N-nicotinoylethylamino]-3-pyridyl)xanthine;
1,3-Diallyl-8-(6-methylamino-3-pyridyl)xanthine;
1-Clopropylmethyl-3-ethyl-8-(6-methylaminopyridin-3-yl)xanthine;
1,3-Diethyl-8-[6-(2-pyridylmethylamino)-3-pyridyl]xanthine;
1,3-Diethyl-8-[6-(3-pyridylmethylamino)-3-pyridyl]xanthine;
1,3-Diethyl-8-[6-(3-methoxybenzylamino)-3-pyridyl]xanthine;
1,3-Dipropyl-8-[6-[2-(3-pyridyl)-ethylamino]-3-pyridyl]xanthine;
1,3-Diethyl-8-[6-[2-(3-pyridyl)-ethylamino]-3-pyridyl]xanthine;
1,3-Dipropyl-8-[6-[2-(2-pyridyl)-ethylamino]-3-pyridyl]xanthine;
1,3-Diethyl-8-[6-[2-(2-pyridyl)-ethylamino]-3-pyridyl]xanthine;
1,3-Diethyl-8-(6-pyrrolidinylpyrid-3-yl)xanthine;
1,3-Diethyl-8-[6-[2-(1-pyrrolidinyl)-ethylamino]-3-pyridyl]xanthine;
1,3-Dipropyl-8-(6-(2-methoxyethyl)amino-3-pyridyl)xanthine;
1,3-Dipropyl-8-(6-(2-acetylaminoethyl)amino-3-pyridyl)xanthine;
1,3-Diethyl-8-(6-bromo-3-pyridyl)xanthine;
1,3-Dipropyl-8-{6-[4-(2-pyridyl)-piperazino]-3-pyridyl}xanthine;
1,3-Dithyl-8-{6-[4-(2-pyridyl)-piperazino]-3-pyridyl}xanthine;
1,3-Diethyl-8-[6-(trans-2,5-dimethylpiperazino)-3-pyridyl]xanthine;
1,3-Dipropyl-8-{6-[4-(2-pyrimidinyl)-piperazino]-3-pyridyl}xanthine;
1,3-Diethyl-8-{6-[4-(2-pyrimidinyl)-piperazino]-3-pyridyl}xanthine;
1,3-Diethyl-8-(6-(2-methoxyethyl)amino-3-pyridyl)xanthine;
1-Propargyl, 3-methyl-8-(6-Bromo-3-pyridyl)xanthine;
1,3-Diethyl-8-[6-[N-nicotinoyl, N-(2-methoxyethyl)amino]-3-pyridyl)xanthine;
1-Propargyl, 3-methyl-8-(6-(2-methoxyethyl)-3-pyridyl)xanthine;
1,3-Diethyl-8-[6-[N-isonicotinoyl, N-(2-methoxyethyl)amino]-3-pyridyl)xanthine;
1-(5-(1,3-Diethyl-2,3,6,7-tetrahydro-2,6-dioxo-1H-purin-8-yl)pyridin-2-yl)-1-(2-methoxyethyl)-3-(pyridine-4-yl)urea;
1,3-Dimethyl-8-(6-bromo-3-pyridyl)xanthine;
1,3-Dimethyl-8-(6-methylamino-3-pyridyl)xanthine;
1,3-Dimethyl-8-[6-[N-nicotinoylmethylamino]-3-pyridyl)xanthine;
1,3-Dipropyl-8-[6-[N-nicotinoyl, N-(2-methoxyethyl)amino]-3-pyridyl)xanthine;
1-Propargyl, 3-methyl-8-[6-[N-nicotinoyl, N-(2-methoxyethyl)amino]-3-pyridyl)xanthine;
1-Propargyl, 3-methyl-8-[6-[N-nicotinoylmethylamino]-3-pyridyl)xanthine;
1,3-Dipropyl-8-(2,6-dichloro-3-pyridyl)xanthine;
1,3-Dipropyl-8-(2,6-dimethylamino-3-pyridyl)xanthine;
1,3-Dipropyl-8-(2,6-di(2-methoxyethyl)-3-pyridyl)xanthine;
1,3-Dipropyl-8-[2,6-di[N-nicotinoylmethylamino]-3-pyridyl)xanthine;
1,3-Dipropyl-8-[2,6-di[N-nicotinoyl, N-methoxyethyl]-3-pyridyl)xanthine;
1,3-Diethyl-8-[6-[N-(2-pyrazinecarbonyl)methylamino]-3-pyridyl)xanthine;
1,3-Diethyl-8-[6-[N-(isoxazole-5-carbonyl)methylamino]-3-pyridyl)xanthine;
1,3-Dipropyl-8-[6-[N-(2-pyrazinecarbonyl)methylamino]-3-pyridyl)xanthine;
1,3-Dipropyl-8-[6-[N-(isoxazole-5-carbonyl)methylamino]-3-pyridyl)xanthine;
1,3-Dipropyl-8-[6-[N-(5-methylisoxazol-3-yl-3-carbonyl)methylamino]-3-pyridyl)xanthine;
1,3-Dipropyl-8-[6-[N-(2-chloro-6-methoxypyridinyl-4-carbonyl), N-methylamino]-3-pyridyl)xanthine;
1,3-Dipropyl-8-[6-[N-(Isonicotinoyl N-oxide), N-methylamino]-3-pyridyl)xanthine;
1-propyl-3-(4-methoxyphenyl)ethyl-8-(6-methylamino-3-pyridyl)xanthine;
1,3-Diethyl-8-[6-[N-(Isonicotinoyl N-oxide), N-methylamino]-3-pyridyl)xanthine;
1,3-Diallyl-8-(6-chloro-3-pyridyl)xanthine;
1-propyl-3-(4-methoxyphenyl)ethyl-8-[6-(N-nicotinoylmethylamino)-3-pyridyl]xanthine;
1-propyl-3-(4-methoxyphenyl)ethyl-8-[6-(N-(6-chloronicotinoyl)methylamino)-3-pyridyl]xanthine;
1,3-diallyl-8-[6-(N-nicotinoylmethylamino)-3-pyridyl]xanthine;
1,3-diallyl-8-[6-(N-(6-chloronicotinoyl)methylamino)-3-pyridyl]xanthine;
1,3-dipropyll-8-[6-(N-[6-(trifluoromethyl)nicotinoyl]methylamino)-3-pyridyl]xanthine;
1,3-diethyl-8-[6-(2-hydroxy-5-methyl)benzaldehydehydrazono]-3-pyridyl]xanthine;
1,3-diethyl-8-[6-(bromopyridine-3-carbaldehydehydrazono]-3-pyridyl]xanthine;

1-Cyclopropyl-3-ethyl-8-(6-methylamino-3-pyridyl)xanthine;
1-Cyclopropyl-3-propyl-8-(6-methylamino-3-pyridyl)xanthine;
1-Propyl-3-cyclopropyl-8-(6-methylamino-3-pyridyl)xanthine;
1-Cyclopropyl-3-propyl-8-(6-(2-methoxyethyl)amino-3-pyridyl)xanthine;
1-Cyclopropyl-3-propyl-8-[6-[N-nicotinoylmethylamino]-3-pyridyl)xanthine;
1,3-Diethyl-8-[6-(N-(6-chloronicotinoyl)methylamino)-3-pyridyl]xanthine;
1,3-Dipropyl-8-(2-chloro-6-methoxyethylamino-4-pyridyl)xanthine;
1,3-Dipropyl-8-(2-chloro-6-methoxyethylamino-4-pyridyl)xanthine;
1,3-Dipropyl-8-[2-[N-nicotinoyl, N-(2-methoxyethyl)amino]-6-chloro-4-pyridyl)xanthine;
1,3-Dipropyl-8-[2-[N-nicotinoyl, N-methylamino]-6-chloro-4-pyridyl)xanthine;
1-Cyclopropyl-3-propyl-8-[6-[N-(6-chloronicotinoyl)methylamino]-3-pyridyl)xanthine;
1-Ethyl-3-cyclopropyl-8-(6-methylamino-3-pyridyl)xanthine;
1-Ethyl-3-cyclopropyl-8-(6-(2-methoxyethyl)amino-3-pyridyl)xanthine;
1,3-Diethyl-8-[6-hydrazino-3-pyridyl]xanthine;
1,3-Diethyl-8-[6-(cyclopropylamino)-3-pyridyl]xanthine;
1,3-Diethyl-8-[6-(cyclopropylmethyl)amino)-3-pyridyl]xanthine;
1,3-Diethyl-8-[6-(ethylamino)-3-pyridyl]xanthine;
1,3-Diethyl-8-[6-[N-nicotinoyl-N-(cyclopropylmethyl)amino]-3-pyridyl)xanthine; and
1-Cyclopropylmethyl-3-ethyl-8-[6-[N-(6-chloronicotinoyl)methylamino]-3-pyridyl)xanthine;

or a pharmaceutical acceptable salt thereof, optionally in the form of a single stereoisomer or mixture of stereoisomers thereof.

49. A pharmaceutical composition comprising:
(a) a therapeutically effective amount of a compound of claim 1; and
(b) a pharmaceutically acceptable excipient.

50. A pharmaceutical composition comprising:
(a) a therapeutically effective amount of a compound of claim 48; and
(b) a pharmaceutically acceptable excipient.

51. A method for treating asthma comprising administering an effective amount of a compound of claim 1 to a mammal in need of such treatment.

52. A method for improving insulin sensitivity, comprising administering an effective amount of a compound of claim 1 or a pharmaceutically acceptable salt thereof to a mammal in need of such treatment.

53. A compound of formula I:

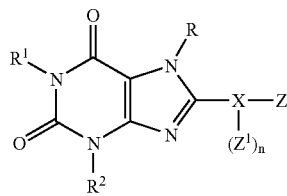

wherein:
R is hydrogen, $(C_1-C_5)$alkyl, halo$(C_1-C_8)$alkyl, $(C_3-C_5)$alkenyl, or $(C_3-C_5)$alkynyl;

$R^1$ and $R^2$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_4-C_{10})$heterocycle, $(C_4-C_{10})$heterocycle$(C_1-C_8)$alkyl-, $(C_6-C_{10})$aryl, $(C_6-C_{10}$ aryl$(C_1-C_8)$alkyl-, $(C_5-C_{10})$heteroaryl, or $(C_5\ C_{10})$heteroaryl$(C_1-C_8)$alkyl-;

X is 2-pyridinyl, 3-pyridinyl, or 4-pyridinyl, each optionally substituted with 1, 2, or 3 substituents independently selected from the group consisting of halo, cyano, nitro, $(C_1-C_8)$alkyl, $-OR^a$, $-SR^a$, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $-C(O)NR^bR^c$;

Z is $-OR^3$, $-SR^3$, $-S(O)_m-NR^4R^5$, $-NR^4R^5$, or $(C_4-C_{10})$heterocycle wherein the heterocycle is optionally substituted with 1, 2, 3, or 4 substituents independently selected from halo, cyano, nitro, $-OR^a$, $-SR^a$, $(C_1-C_8)$alkyl, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $C(O)R^a$, $-COOR^a$, and $-C(O)NR^bR^c$;

provide that X-$(Z')_n$-Z is other than 6-(pyrid-2-yl)-pyrid-2yl;

each $Z^1$ is independently $(C_1-C_8)$alkyl, $(C_2-C_8)$alkenyl, $(C_2-C_8)$alkynyl, $-OR^6$, $-SR^6$, halo, $R^6O(C_1-C_8)$alkyl, $R^7R^8N(C_1-C_8)$alkyl, halo$(C_1-C_8)$alkyl, $-NR^7R^8$, $R^7R^8N(C_1-C_8)$alkyl, $-C(O)R^6$, $-COOR^6$, and $-C(O)NR^7R^8$;

$R^3$ is $(C_1-C_8)$alkyl, $(C_3-C_8)$alkenyl, $(C_3-C_8)$alkynyl, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, $-C(O)R^6$, or $-C(O)NR^7R^8$;

$R^4$ and $R^5$ are independently hydrogen, $(C_1-C_8)$alkyl, $(C_3-C_8)$alkenyl, $(C_3-C_8)$alkynyl, $(C_1-C_8)$alkoxy, $(C_3-C_8)$cycloalkyl, $(C_3-C_8)$cycloalkyl$(C_1-C_8)$alkyl-, $(C_6-C_{18})$polycycloalkyl, $(C_6-C_{18})$polycycloalkyl$(C_1-C_8)$alkyl-, $(C_3-C_{10})$heterocycle, $(C_3-C_{10})$heterocycle$(C_1-C_8)$alkyl-, $-NR^7R^8$, $(C_6-C_{10})$aryl, $(C_6-C_{10})$aryl$(C_1-C_8)$alkyl-, $(C_5-C_{10})$heteroaryl, $(C_5-C_{10})$heteroaryl$(C_1-C_8)$alkyl-, $-C(O)R^6$, $-CO_2R^6$, $-C(O)NR^7R^8$, or $-S(O)_2-NR^7R^8$; or $R^4$ and $R^5$ together with the atoms to which they are attached form a saturated or partially unsaturated, mono-, bicyclic- or aromatic ring having 3, 4, 5, 6, 7, or 8, ring atoms and optionally comprising 1, 2, 3, or 4 heteroatoms selected from non-peroxide oxy ($-O-$), thio ($-S-$), sulfinyl ($-SO-$), sulfonyl ($-S(O)_2-$) and amine $-N(R^9)-$ in the ring, and wherein the ring is optionally substituted with 1, 2, 3, or 4 substituents independently selected from halo, cyano, nitro, $-OR^a$, $-SR^a$, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $-C(O)NR^bR^c$;

$X^1$ is $-OR^6$, $-C(O)R^6$, $-CO_2R^6$, or $-NR^7R^8$; and Y is oxy ($-O-$), thio ($-S-$), sulfinyl ($-SO-$), sulfonyl ($-S(O)_2-$) and amine $-N(R^9)-$;

wherein the alkyl, alkenyl, cycloalkyl, alkynyl, aryl, heterocycle or heteroaryl groups of $R^1$, $R^2$, $R^3$, $R^4$ and $R^5$ groups are optionally substituted with one or more substituents independently selected from halo, cyano, nitro, $-OR^a$, $-SR^a$, $(C_6-C_{10})$aryl, $-O(C_6-C_{10})$aryl, hydroxy$(C_1-C_8)$alkyl, $R^bR^cN(C_1-C_8)$alkyl, halo$(C_1-C_8)$alkyl, $-NR^bR^c$, $-C(O)R^a$, $-COOR^a$, and $-C(O)NR^bR^c$;

wherein $R^6$ is hydrogen, $(C_1-C_8)$alkyl, $R^aO(C_1-C_8)$alkyl, $R^bR^cN(C_1-C_8)$alkyl, halo$(C_1-C_8)$alkyl, $(C_3-C_{10})$heterocycle, $(C_3-C_{10})$heterocycle$(C_1-C_8)$alkyl-, $(C_6-C_{10})$aryl, $(C_6-C_{10})$aryl$(C_1-C_8)$alkyl-, $(C_4-C_{10})$heteroaryl, $(C_4-$ $C_{10}$)heteroaryl($C_1$-$C_9$)alkyl-; wherein the heterocycle, heteroaryl or aryl are optionally substituted with 1, 2, 3, or 4 substituents independently selected from halo, cyano, nitro, —OR$^a$, —SR$^a$, ($C_6$-$C_{10}$)aryl, —O($C_6$-$C_{10}$)aryl, hydroxy($C_1$-$C_8$)alkyl, R$^b$R$^c$N($C_1$-$C_8$)alkyl, halo($C_1$-$C_8$)alkyl, —NR$^b$R$^c$, —C(O)R$^a$, —COOR$^a$, and C(O)NR$^b$R$^c$;

wherein R$^7$, R$^8$ and R$^9$ are independently hydrogen, ($C_1$-$C_8$)alkyl, R$^a$O($C_1$-$C_8$)alkyl, R$^b$R$^c$N($C_1$-$C_8$)alkyl, halo($C_1$-$C_8$)alkyl, ($C_3$-$C_{10}$)heterocycle, ($C_6$-$C_{10}$)aryl, ($C_6$-$C_{10}$)aryl($C_1$-$C_8$)alkyl-, ($C_4$-$C_{10}$)heteroaryl; —COOR$^a$, —C(O)R$^a$, or —C(O)NR$^b$R$^c$ wherein the heterocycle, heteroaryl or aryl are optionally substituted with 1, 2, 3, or 4 substituents independently selected from halo, cyano, nitro, —OR$^a$, —SR$^a$, ($C_6$-$C_{10}$)aryl, —O($C_6$-$C_{10}$)aryl, hydroxy($C_1$-$C_8$)alkyl, R$^b$R$^c$N($C_1$-$C_8$)alkyl, halo($C_1$-$C_8$)alkyl, —NR$^b$R$^c$, —C(O)R$^a$, —COOR$^a$, and —C(O)NR$^b$R$^c$; or R$^7$ and R$^8$ together with the atoms to which they are attached form a saturated or partially unsaturated, mono-, bicyclic- or aromatic ring having 3, 4, 5, 6, 7, or 8, ring atoms optionally ring having from 4 to eight ring atoms and optionally comprising 1, 2, 3, or 4 heteroatoms selected from non-peroxide oxy (—O—), thio (—S—), sulfinyl (—SO—), sulfonyl (—S(O)$_2$—) or amine —N(R$^b$)— in the ring;

R$^a$ is hydrogen, or ($C_1$-$C_6$)alkyl; R$^b$ and R$^c$ are each independently hydrogen, ($C_1$-$C_6$)alkyl, ($C_1$-$C_6$)alkoxy, ($C_3$-$C_8$)cycloalkyl, ($C_1$-$C_6$)alkylthio, ($C_6$-$C_{10}$)aryl, ($C_6$-$C_{10}$)aryl($C_1$-$C_6$)alkyl-, heteroaryl, or heteroaryl ($C_1$-$C_6$)alkyl-; or R$^b$ and R$^c$ together with the nitrogen to which they are attached, form a pyrrolidyl, piperidyl, piperazinyl, azepinyl, diazepinyl, morpholinyl, or thiomorpholinyl ring; and where n is 0, 1, 2, 3, 4, 5, 6, 7, or 8; m is 1, or 2; and q is 1, 2, 3, or 4; or a pharmaceutically acceptable salt thereof.

54. The compound of claim 53, wherein wherein —X($Z^1$)$_n$-Z is:

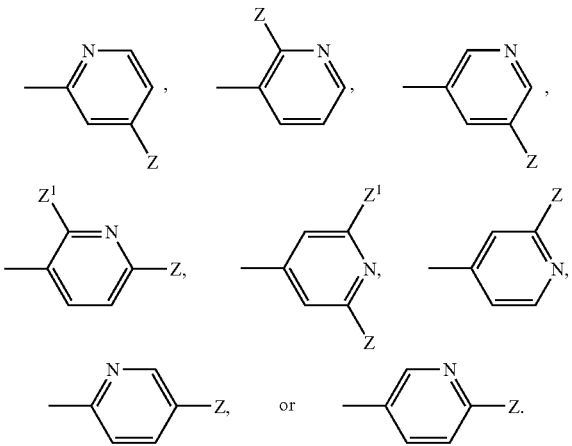

55. The compound of claim 54, wherein X wherein —X($Z^1$)$_n$-Z has the formula

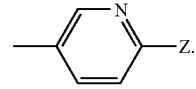

* * * * *

UNITED STATES PATENT AND TRADEMARK OFFICE
CERTIFICATE OF CORRECTION

| | | |
|---|---|---|
| PATENT NO. | : 7,342,006 B2 | Page 1 of 1 |
| APPLICATION NO. | : 10/923592 | |
| DATED | : March 11, 2008 | |
| INVENTOR(S) | : Guoquan Wang, Jayson M. Rieger and Robert D. Thompson | |

It is certified that error appears in the above-identified patent and that said Letters Patent is hereby corrected as shown below:

Title page, item [75] attorney should read --Kelly Hollowell-- instead of "Kelly Hallowell" as reflected on the original registration certificate.

Signed and Sealed this

Tenth Day of June, 2008

JON W. DUDAS
*Director of the United States Patent and Trademark Office*